US009150891B2

(12) United States Patent
Sakaguchi et al.

(10) Patent No.: US 9,150,891 B2
(45) Date of Patent: Oct. 6, 2015

(54) METHOD FOR TRANSFORMING STRAMENOPILES

(75) Inventors: Keishi Sakaguchi, Fukuoka (JP); Takanori Matsuda, Fukuoka (JP); Takumi Kobayashi, Fukuoka (JP); Makoto Ito, Fukuoka (JP); Naoki Nagano, Miyazaki (JP); Masahiro Hayashi, Miyazaki (JP); Daisuke Honda, Kobe (JP); Yosuke Taoka, Chiyoda-ku (JP); Yuji Okita, Chiyoda-ku (JP); Hitoshi Izumida, Chiyoda-ku (JP); Shinichi Sugimoto, Chiyoda-ku (JP)

(73) Assignees: KYUSHU UNIVERSITY, NATIONAL UNIVERSITY CORPORATION, Fukuoka (JP); UNIVERSITY OF MIYAZAKI, Miyazaki (JP); KONAN GAKUEN, Hyogo (JP); NIPPON SUISAN KAISHA, LTD., Tokyo (JP)

( * ) Notice: Subject to any disclaimer, the term of this patent is extended or adjusted under 35 U.S.C. 154(b) by 47 days.

(21) Appl. No.: 13/497,894

(22) PCT Filed: Sep. 24, 2010

(86) PCT No.: PCT/JP2010/066599
§ 371 (c)(1),
(2), (4) Date: Jul. 23, 2012

(87) PCT Pub. No.: WO2011/037207
PCT Pub. Date: Mar. 31, 2011

(65) Prior Publication Data
US 2012/0322116 A1  Dec. 20, 2012

(30) Foreign Application Priority Data

Sep. 24, 2009 (JP) ................................. 2009-219820

(51) Int. Cl.
| | |
|---|---|
| *C12P 7/64* | (2006.01) |
| *C12P 21/06* | (2006.01) |
| *C12N 1/00* | (2006.01) |
| *C12N 1/10* | (2006.01) |
| *C12N 15/00* | (2006.01) |
| *C11C 3/00* | (2006.01) |
| *C12N 9/02* | (2006.01) |
| *C12N 15/79* | (2006.01) |
| *C12N 15/82* | (2006.01) |

(52) U.S. Cl.
CPC ................. *C12P 7/6409* (2013.01); *C11C 3/00* (2013.01); *C12N 9/0083* (2013.01); *C12N 15/79* (2013.01); *C12N 15/8201* (2013.01); *C12N 15/8247* (2013.01); *C12P 7/6427* (2013.01)

(58) Field of Classification Search
CPC .... C12P 7/6472; C12P 7/6427; C12P 7/6409; C12P 7/649; C12N 15/8247; C12N 15/52; C12N 9/1029; C12N 15/79; C12N 1/12; C12N 15/63; C12N 15/64; C07K 14/405
See application file for complete search history.

(56) References Cited

U.S. PATENT DOCUMENTS

| | | | |
|---|---|---|---|
| 2002/0156254 A1* | 10/2002 | Qiu et al. ...................... 536/23.1 |
| 2003/0166207 A1 | 9/2003 | Roessler et al. |
| 2006/0275904 A1 | 12/2006 | Ono et al. |
| 2006/0286650 A1 | 12/2006 | Ono et al. |
| 2008/0022422 A1 | 1/2008 | Weaver et al. |
| 2008/0072351 A1 | 3/2008 | Meesapyodsuk et al. |
| 2008/0155705 A1 | 6/2008 | Zank et al. |

FOREIGN PATENT DOCUMENTS

| | | |
|---|---|---|
| JP | 2005-503125 A | 2/2005 |
| JP | 2006-304686 A | 11/2006 |
| JP | 2007-527716 A | 10/2007 |
| JP | 2006-304685 A | 11/2009 |
| WO | 2008/006202 A1 | 1/2008 |
| WO | 2008/144473 A2 | 11/2008 |

OTHER PUBLICATIONS

Yokoyama et al. Taxonomic rearrangement of the genus Ulkenia sensu lato based on morphology, chemotaxonomical characteristics, and 18S rRNA gene phylogeny (*Thraustochytriaceae, Labyrinthulomycetesz*): emendation for Ulkenia and erection of *Botryochytrium, Parietichytrium, and Sicyoidpchytrium* gen. Nov., Mycoscience (2007), 48: 329-341.*

Naoki Nagano et al.; "Developement of discrimination method for biosynthesis pathway of polyunsaturated fatty acid in Labyrinthulida"; Dept. Biol. Pro. Env. Sci. Fac. Agric., Miyazaki Univ., 2Grad. Sch. of Biores. Bioenviron. Sci. Kyushu Univ., 3Nippon Suisan Kaisha Ltd, 4Dept. Biol. Fac. of Sci. and Eng., Konan Univ., 5Bio-Arch., Kyushu Univ., 2009, vol. 2009, p. 35.

Takumi Kobayashi et al.; "Isolation of the gene which is related to biosynthesis of polyunsaturated fatty acid from Labryinthulida and its functional analysis"; 1Dept. Biosci., Biotech., Grad. Sch. Biores, Bioenviron. Sci., Kyushu Univ., 2Grad. Sch., Fac. of Agric., Kyushu Univ., 3Bio-Arc., Kyushu Univ., 2008, vol. 2008, p. 22.

(Continued)

*Primary Examiner* — Iqbal H Chowdhury
(74) *Attorney, Agent, or Firm* — Westerman, Hattori, Daniels & Adrian, LLP

(57) ABSTRACT

Disclosed is a transformation method whereby an ability to produce a useful substance of a stramenopile can be improved. The method for transforming a stramenopile comprises transferring a foreign gene into the stramenopile which is a microorganism belonging to the class *Labyrinthula*, more specifically, to a genus *Labyrinthula, Altornia, Aplanochytrium, Schizochytrium, Aurantiochytrium, Thraustochytrium, Ulkenia*, etc. Said foreign gene, which is a gene relating to tolerance against an antibiotic, a colorimetric protein and/or a fatty acid desaturase (Δ5 desaturase gene, Δ12 desaturase gene and/or ω3 desaturase gene), is transferred by using the electroporation or gene-gun technique.

5 Claims, 57 Drawing Sheets

(56) References Cited

OTHER PUBLICATIONS

Tsunehiro Aki et al.; "Development of transformation system of oleaginous microorganism, Labyrinthulida"; Abstracts of the Annual Meeting of the Society for Biotechnology, Japan, Dept. Mol. Biotech., Grad. Sch. Adv. Sci. Mat., Hiroshima Univ., 2005, vol. 2005, p. 199.

Hiroaki Iwasaka et al.; "Modification of lipid composition by genetic engineering in oleaginous microorganisms, Labyrunthulida"; Abstracts of the Annual Meeting of the Scoiety for Biotechnology, Japan Dept. Mol. Biotech., Grad. Sch. Adv. Sci. Mat., Hiroshima Univ., 2008, vol. 60, p. 136.

Takumi Kobayashi et al.; "Expression of a delta-5 desaturase gene results in the alternation of fatty acid composition of *Aurantiochytrium* sp. mh0186"; 1Dept. Biosci. Biotech., Grad. Sch. of Biores,. Bioenviron. Sci., Kyushu Univ., Grad. Sch. Bioresource &Bioenviron. Sci. Kyushu Univ., 2Fac. of Agric. Kyushu Univ., 3Fac. of Agric., Saga Univ., 4Nippon Suisan Kaisha Ltd., 5Fac of Agric., Miyazaki Univ., 6Fac . of Sci. and Enf., Konan Univ., 7Bio-Arch., Kyushu Univ. Sep. 25, 2009, p. 2P-200.

* cited by examiner

G418 – 0.5 mg/ml~

Hygromycin – 1.0 mg/ml~

Blasticidin – 75 µg/ml~

G418 – 1 mg/ml~ / Hygromycin – 0.3 mg/ml~ / Blasticidin – 0.6 mg/ml~
Zeocin – 70 µg/ml~

G418 – 0.175 mg/ml~

Hygromycin – 0.8 mg/ml~

Zeocin – 8 µg/ml~

G418 – 0.6 mg/ml~ / Hygromycin – 32 µg/ml~
Blastisidian and Zeocin require higher concentrations G418 – 1 mg/ml~, Hygromycin – 2 mg/ml~, Blasticidin – 0.4 mg/ml~

G418 – 1.5 mg/ml~, Hygromycin – 6 mg/ml~, Blasticidin – 1.4 mg/ml~ Zeocin require higher concentrations

G418 – 0.5 mg/ml~, Hygromycin – 2.0 mg/ml~, Blasticidin – 0.5 mg/ml~
Blasticidin also inhibits at 1.42mg/ml or higher

G418 – 1.0 mg/ml~, Hygromycin – 1.0 mg/ml~

(A) *Aurantiochytrium* sp.mh0186 (Neo$^r$)

(C) *T. aureum* (Neo$^r$)

(B) *Aurantiochytrium* sp.mh0186 (gfp)

(D) *T. aureum* (gfp)

FIG. 28

(A) NEOMYCIN-RESISTANT GENE (B) Δ12 DESATURASE GENE (a)

(b)

(c)

a b

M.  OneSTEP Ladder 1kb.
1.  Schizochytrium aggregatum ATCC28209
2.  Shizochytrium sp. SEK210
3.  Shizochytrium sp. SEK345
4.  Ulkenia sp. ATCC 28207
5.  Botryochytrium radiatum SEK353
6.  Parietichytrium sarkarianum SEK364

FIG. 55

| COMPARISON WITH WILED TYPE | | T.aureum Sdic w3 | T.aureum mock | FA |
|---|---|---|---|---|
| 1.25 | 124.8% | 0.30 | 0.24 | C14:0 |
| 1.16 | 115.5% | 0.59 | 0.51 | C15:0 |
| 1.15 | 114.7% | 16.83 | 14.67 | C16:0 |
| 0.94 | 93.9% | 0.40 | 0.42 | C17:0 |
| 0.84 | 84.3% | 4.07 | 4.83 | C18:0 |
| 0.68 | 67.9% | 2.07 | 3.05 | C18:1n-9 |
| 0.96 | 96.0% | 1.60 | 1.67 | C18:1n-7 |
| 0.93 | 92.7% | 1.63 | 1.76 | C18:2n-6(LA) |
| 0.94 | 93.8% | 0.02 | 0.03 | C19:0 |
| 1.01 | 100.6% | 0.17 | 0.17 | C18:3n-6(GLA) |
| 0.95 | 94.7% | 0.50 | 0.53 | C19:2 |
| 0.74 | 74.2% | 0.54 | 0.70 | C20:3n-6(DGLA) |
| 0.10 | 9.8% | 0.71 | 7.16 | C20:4n-6(AA) |
| 8.30 | 829.6% | 0.28 | 0.03 | C20:4n-3(ETA) |
| 1.81 | 180.8% | 11.32 | 6.26 | C20:5n3(EPA) |
| 0.26 | 26.4% | 0.52 | 1.96 | C22:4n-6(DTA) |
| 0.14 | 14.2% | 1.36 | 9.57 | C22:5n-6(DPA) |
| 1.79 | 178.6% | 2.23 | 1.25 | C22:5n-3(DPA) |
| 1.22 | 122.5% | 54.28 | 44.32 | C22:6n-3(DHA) |

SEQUENCE LISTING

```
<160> NUMBER OF SEQ ID NOS: 125

<210> SEQ ID NO 1
<211> LENGTH: 19
<212> TYPE: DNA
<213> ORGANISM: Artificial Sequence
<220> FEATURE:
<223> OTHER INFORMATION: Chemically synthesized primer
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (11)..(11)
<223> OTHER INFORMATION: n is inosine.
<220> FEATURE:
<221> NAME/KEY: misc_feature
<222> LOCATION: (14)..(14)
<223> OTHER INFORMATION: n is a, c, g, or t

<400> SEQUENCE: 1
thgaygcncc nggncaymg                                                    19

<210> SEQ ID NO 2
<211> LENGTH: 980
<212> TYPE: DNA
<213> ORGANISM: Unknown
<220> FEATURE:
<223> OTHER INFORMATION: RACE product believed to be partial sequence of
      T. aureum-derived EF-1alpha gene

<400> SEQUENCE: 2
tcgtcgactc gtcgaccggc ggttcgaggc cggcatcgcc aaggacggcc agaccgcga      60 gcacgccctt ctggccttca ccctcggcat ccagcagatc atcgtcgccg tcaacaagat    120
ggacgacaag tcgaccatgt acagcgaggc ccgcttcacg gagatcgtca ccgaggtgtc    180
cggcttcctc ggcaaggtcg gcttcaagcc caagaagatc accttcgtgc ccatctcggg    240
ctgggctggc gacaacatga tcgagaagtc caccaacatg ccctggtaca agggggccta    300
ccttctggag gccctcgacc agatcaagcc gcccaagcgc ccggtcgaca gcccctccg    360 cctgcccctc caggatgtgt acaagattgg cggcatcggc acggtccccg tcggccgcgt    420
cgagaccggc atcatcaagc ccggcatgac cgcctacttt gcccccaccg gcatctccac    480
cgaagtcaag tccgtcgaga tgcaccacga gtccatcccg gaggcctccc ccggtgacaa    540
cgtcggcttc aacatcaaga acgtgtcggt caaggtacat tcgccgcggc aacgttgccg    600
gcggatgcca agtaacgacc cgccccgcgg cgccgtactc gttcgaggcc caggtcatcg    660
tcatgggcca ccccggtgag atccgcgccg gctatgcgcc cgtgctcgac tgccacactg    720
cccacattgc ctgcaagttc gctgagctcc agaacaagat ggaccgccgc tcgggcaaga    780
ttctcgagga gaccccaag ttcatcaagt cgggtggact ctgccatggt caagatgtat    840
cccctccaag cgcatgtgcg tcgagtcctt caccgagtac ccgccgctcg gccgctttgc    900
cgtgcgcgac atgcgcgtca ccgtcgctgt cggcgtcatc aagtccgtca ccaagggcga    960
caaataaatt ctacgaaaga                                                980
```

<210> SEQ ID NO 3
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 3
gtgaaggcca gaagggcgtg                                              20

<210> SEQ ID NO 4
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 4
gccggtcgac gagtcgacg                                               19

<210> SEQ ID NO 5
<211> LENGTH: 496
<212> TYPE: DNA
<213> ORGANISM: Unknown
<220> FEATURE:
<223> OTHER INFORMATION: RACE product believed to be partial sequence of
      T. aureum-derived EF-1alpha gene

<400> SEQUENCE: 5
ctcactatag ggcaagcagt ggtatcaacg cagagtacgc gggagtagca agcagcggca    60
aaggaaggca agatgggcaa gaccaaggag catgtcaacc ttgtggtgat cggccatgtc   120
gacgccggca agtcgaccac caccggccac ttgatctaca gtgcggtgg catcgacaag    180 cgcacgatcg agaagttcga aaggaggcc gccgagctcg gcaagagctc gttcaagtac   240
gcctgggtgc tcgacaagct caaggccgag cgcgagcgcg tatcaccat cgacatcgcc   300 ctctggaagt cgagtcgcc ccgctttgac tttaccgtca tcgatgcccc cggccaccgc   360
gacttcatca gaacatgat taccggcacc agccaggccg acgtcgccat tctacgtcgt   420
cgactcgtcg accggcggtt cgaggccggc atcgccaagg acggccagac ccgcgagcac   480
gcccttctgg ccttca                                                 496

<210> SEQ ID NO 6
<211> LENGTH: 436
<212> TYPE: DNA
<213> ORGANISM: Unknown
<220> FEATURE:
<223> OTHER INFORMATION: RACE product believed to be partial sequence of
      T. aureum-derived EF-1alpha gene

<400> SEQUENCE: 6
ctcactatag ggcaagcagt ggtatcaacg cagagtacgc gggagtagca agcagcggca    60
aaggaaggca agatgggcaa gaccaaggag catgtcaacc ttgtggtgat cggccatgtc   120
gacgccggca agtcgaccac caccggccac ttgatctaca gtgcggtgg catcgacaag    180 cgcacgatcg agaagttcga aaggaggcc gccgagctcg gcaagagctc gttcaagtac   240
gcctgggtgc tcgacaagct caaggccgag cgcgagcgcg tatcaccat cgacatcgcc   300 ctctggaagt cgagtcgcc ccgctttgac tttaccgtca tcgatgcccc cggccaccgc   360
gacttcatca gaacatgat taccggcacc agccaggccg acgtcgccat tctacgtcgt   420

```
cgactcgtcg accggc                                                      436
```

<210> SEQ ID NO 7
<211> LENGTH: 1396
<212> TYPE: DNA
<213> ORGANISM: Thraustochytrium aureum

<400> SEQUENCE: 7

```
ctcactatag ggcaagcagt ggtatcaacg cagagtacgc gggagtagca agcagcggca       60
aaggaaggca agatgggcaa gaccaaggag catgtcaacc ttgtggtgat cggccatgtc      120
gacgccggca agtcgaccac caccggccac ttgatctaca agtgcggtgg catcgacaag      180
cgcacgatcg agaagttcga gaaggaggcc gccgagctcg gcaagagctc gttcaagtac      240
gcctgggtgc tcgacaagct caaggccgag cgcgagcgcg gtatcaccat cgacatcgcc      300
ctctggaagt tcgagtcgcc ccgctttgac tttaccgtca tcgatgcccc cggccaccgc      360
gacttcatca gaacatgat taccggcacc agccaggccg acgtcgccat tctacgtcgt      420
cgactcgtcg accggcggtt cgaggccggc atcgccaagg acggcagac ccgcgagcac       480
gcccttctgg ccttcaccct cggcatccag cagatcatcg tcgccgtcaa caagatggac      540
gacaagtcga ccatgtacag cgaggcccgc ttcacggaga tcgtcaccga ggtgtccggc      600
ttcctcggca aggtcggctt caagcccaag aagatcacct tcgtgcccat ctcgggctgg      660
gctggcgaca catgatcga agtccacc aacatgccct ggtacaaggg gccctacctt         720
ctggaggccc tcgaccagat caagccgccc aagcgcccgg tcgacaagcc cctccgcctg      780
cccctccagg atgtgtacaa gattggcggc atcggcacgg tccccgtcgg ccgcgtcgag      840
accggcatca tcaagcccgg catgaccgcc tactttgccc ccaccggcat ctccaccgaa      900
gtcaagtccg tcgagatgca ccacgagtcc atcccggagg cctcccccgg tgacaacgtc      960
ggcttcaaca tcaagaacgt gtcggtcaag gtacattcgc cgcggcaacg ttgccggcgg     1020
atgccaagta acgacccgcc ccgcggcgcc gtactcgttc gaggcccagg tcatcgtcat     1080
gggccacccc ggtgagatcc gcgccggcta tgcgcccgtg ctcgactgcc acactgccca     1140
cattgcctgc aagttcgctg agctccagaa caagatggac cgccgctcgg caagattct      1200
cgaggagacc cccaagttca tcaagtcggg tggactctgc catggtcaag atgtatcccc     1260
tccaagcgca tgtgcgtcga gtccttcacc gagtacccgc cgctcggccg ctttgccgtg     1320
cgcgacatgc gcgtcaccgt cgctgtcggc gtcatcaagt ccgtcaccaa gggcgacaaa     1380
taaattctac gaaaga                                                    1396
```

<210> SEQ ID NO 8
<211> LENGTH: 340
<212> TYPE: PRT
<213> ORGANISM: Thraustochytrium aureum

<400> SEQUENCE: 8

```
Met Gly Lys Thr Lys Glu His Val Asn Leu Val Val Ile Gly His Val
1               5                  10                  15

Asp Ala Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
        35                  40                  45

Leu Gly Lys Ser Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
```

```
                65                  70                  75                  80
Glu Ser Pro Arg Phe Asp Phe Thr Val Ile Asp Ala Pro Gly His Arg
                85                  90                  95
Asp Phe Ile Lys Asn Met Ile Thr Gly Thr Ser Gln Ala Asp Val Ala
                100                 105                 110
Ile Leu Arg Arg Arg Leu Val Asp Arg Phe Glu Ala Gly Ile Ala
                115                 120                 125
Lys Asp Gly Gln Thr Arg Glu His Ala Leu Leu Ala Phe Thr Leu Gly
            130                 135                 140
Ile Gln Gln Ile Ile Val Ala Val Asn Lys Met Asp Asp Lys Ser Thr
145                 150                 155                 160
Met Tyr Ser Glu Ala Arg Phe Thr Glu Ile Val Thr Glu Val Ser Gly
                165                 170                 175
Phe Leu Gly Lys Val Gly Phe Lys Pro Lys Lys Ile Thr Phe Val Pro
                180                 185                 190
Ile Ser Gly Trp Ala Gly Asp Asn Met Ile Glu Lys Ser Thr Asn Met
                195                 200                 205
Pro Trp Tyr Lys Gly Pro Tyr Leu Leu Glu Ala Leu Asp Gln Ile Lys
                210                 215                 220
Pro Pro Lys Arg Pro Val Asp Lys Pro Leu Arg Leu Pro Leu Gln Asp
225                 230                 235                 240
Val Tyr Lys Ile Gly Gly Ile Gly Thr Val Pro Val Gly Arg Val Glu
                245                 250                 255
Thr Gly Ile Ile Lys Pro Gly Met Thr Ala Tyr Phe Ala Pro Thr Gly
                260                 265                 270
Ile Ser Thr Glu Val Lys Ser Val Glu Met His His Glu Ser Ile Pro
                275                 280                 285
Glu Ala Ser Pro Gly Asp Asn Val Gly Phe Asn Ile Lys Asn Val Ser
            290                 295                 300
Val Lys Val His Ser Pro Arg Gln Arg Cys Arg Arg Met Pro Ser Asn
305                 310                 315                 320
Asp Pro Pro Arg Gly Ala Val Leu Val Arg Gly Pro Gly His Arg His
                325                 330                 335
Gly Pro Pro Arg
            340

<210> SEQ ID NO 9
<211> LENGTH: 1023
<212> TYPE: DNA
<213> ORGANISM: Thraustochytrium aureum

<400> SEQUENCE: 9
atgggcaaga ccaaggagca tgtcaacctt gtggtgatcg ccatgtcga cgccggcaag      60 tcgaccacca ccggccactt gatctacaag tgcggtggca tcgacaagcg cacgatcgag     120
aagttcgaga aggaggccgc cgagctcggc aagagctcgt tcaagtacgc ctgggtgctc     180
gacaagctca aggccgagcg cgagcgcggt atcaccatcg acatcgccct ctggaagttc     240
gagtcgcccc gctttgactt taccgtcatc gatgcccccg gccaccgcga cttcatcaag     300
aacatgatta ccggcaccag ccaggccgac gtcgccattc tacgtcgtcg actcgtcgac     360
cggcggttcg aggccggcat cgccaaggac ggccagaccc gcgagcacgc ccttctggcc     420
ttcaccctcg gcatccagca gatcatcgtc gccgtcaaca agatggacga caagtcgacc     480
atgtacagcg aggcccgctt cacggagatc gtcaccgagg tgtccggctt cctcggcaag     540
```

```
gtcggcttca agcccaagaa gatcaccttc gtgcccatct cgggctgggc tggcgacaac      600
atgatcgaga agtccaccaa catgcccctgg tacaagggc cctaccttct ggaggccctc      660
gaccagatca agccgcccaa gcgcccggtc gacaagcccc tccgcctgcc cctccaggat      720
gtgtacaaga ttggcggcat cggcacggtc cccgtcggcc gcgtcgagac cggcatcatc      780
aagcccggca tgaccgccta ctttgccccc accggcatct ccaccgaagt caagtccgtc      840
gagatgcacc acgagtccat cccggaggcc tccccggtg acaacgtcgg cttcaacatc       900
aagaacgtgt cggtcaaggt acattcgccg cggcaacgtt gccggcggat gccaagtaac      960
gacccgcccc gcggcgccgt actcgttcga ggcccaggtc atcgtcatgg ccaccccgg      1020 tga                                                                  1023
```

<210> SEQ ID NO 10
<211> LENGTH: 26
<212> TYPE: DNA
<213> ORGANISM: Artificial Sequence
<220> FEATURE:
<223> OTHER INFORMATION: Chemically synthesized primer

<400> SEQUENCE: 10

```
cctccttctc gaacttctcg atcgtg                                           26
```

<210> SEQ ID NO 11
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 11

```
catggtcaag atgtatcccc tccaa                                            25
```

<210> SEQ ID NO 12
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 12

```
tcaccaaggg cgacaaataa attct                                            25
```

<210> SEQ ID NO 13
<211> LENGTH: 615
<212> TYPE: DNA
<213> ORGANISM: Thraustochytrium aureum

<400> SEQUENCE: 13

```
ctagccttcc tttgccgctg cttgctactc ctgctactcc tgcttgctac tccgtgctgc       60
tccgcgttcc gtctctgccg cgccgtcaac gagcgcctcc acggatttat ccgcccaacg      120
cagctcacct tggccgccta tctaaccccg caaaccgcct cccagccaac cagtatgcac      180
cgccgtaagg cggatgcccg gaacacagcc ccgccgcgac ctaacaccaa cactaaccgc      240
ccgcgcccgc cgccaccttta cgcagccgca ccgcccgcc gcgccgcgct gctgggccgc      300
cctccgcccc gcggaccgcc ctgcgcactc gcggggggcta tcctggtagt cgcgcgctag    360
gaggtgctag gcggcccgc gcgtccaccg cgcccgcgac cccgccgaac agcctggagc      420
cctaaccctc ggtttggctt aaggaggacc gccgccaggc cccccgtgac gcgggcccc      480 ggggctctct gctgcggccg cgtctcgtcg cgctttccgt cacgacacag ggacccgag      540
```

```
gtgacgagga cgaatgcgcg aagctttcgc ccggatgagt ggcggcctga tgtgaggaac    600
ggcttttttt gaatt                                                     615

<210> SEQ ID NO 14
<211> LENGTH: 1414
<212> TYPE: DNA
<213> ORGANISM: Thraustochytrium aureum

<400> SEQUENCE: 14
gatccgcgcc ggctatgcgc ccgtgctcga ctgccacact gcccacattg cctgcaagtt     60
cgctgagctc cagaacaaga tggaccgccg ctcgggcaag attctcgagg agaccccccaa   120 gttcatcaag tcgggtggac tctgccatgg tcaagatgta tcccctccaa gcgcatgtgc   180
gtcgagtcct tcaccgagta cccgccgctc ggccgctttg ccgtgcgcga catgcgcgtc   240
accgtcgctg tcggcgtcat caagtccgtc accaagggcg acaaataaat tctacgaaag   300
atttttttcc tcaagaagcg ccctaaagtt gaccccctagc agcgacgact gtgtgtgccg   360
ttgtgagtcg agttgcgatg tcgtgcagcg cccgtcgcgt cccatgctcg cgcgcgactc   420
cgtctctgct tttcatctca agtcaagagt gggaagttcc cttgctttat ctcactattt   480
agaggtcgct cacggctgct ggttcctcgt cgcatgtagc acagcctcgt ccaatcgcag   540
cctgcaccac cccgctcgcc tgggaaaatg cgctcagcgg attcgcactg gcactcctct   600
cctcggacag gtgcgatgtg gaagcggtca catcctcggc cccctcggcc acgccagcat   660
ctgcgcaatc gctctcctcg ttctcagccg caaccgcagg caggccgacg tcgtttacct   720
cggaatccac cgagcatttc gagcccatcg cgctggcgtc cacctcgatc ataccttctc   780
catcgccgtc cgctgcggct tccgattctt ctgctgccgc aaccgcgacg tcggcccccg   840
tctcctccgt tctttccgat gccggcgcag tggccgcgcc ctctgctcga accggctcgt   900
gttcagcgtc agggcctgcg cttgagctcg ggcggctctt ccgagtgatc cggccccgcg   960
aggcaaggaa tcggcggctc tggagtgtcg gggcagccgc tctcactgcc ggtctttggc  1020
tggctgcctg tcctgcctcg cgttggcctt tgcttttgcc taggctttcg ccttggtgac  1080
ggcgtttgcc tgctgcggcg acttggcgcg gccgcgaat agcgcctcaa agtcctgctc    1140
gaggcgcccc agctctgact tgatttgcga ggtcccggtg gcatgagctc cgctgccctc  1200
gtccttacgg cccgtctttc gctccattgc ttgccgcgcg tgtacaccgg aagaaacttg  1260
atctcgttga ggttgccggg gcgaaacagg gacatctgtg cgccgtgctg cttgtctgag  1320
ggcgctgcgg gaccctgctt ggccaaccca gggcttggac ctgccccccc ccttcttccc  1380
ccaccgccgc gccaccccca tctccttccc gctt                               1414

<210> SEQ ID NO 15
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 15
atgcaratht tygtkaarac yyts                                            24

<210> SEQ ID NO 16
<211> LENGTH: 278
<212> TYPE: DNA
<213> ORGANISM: Thraustochytrium aureum
```

<400> SEQUENCE: 16

```
atgcagatct tcgtcaagac gctcacgggc aagaccatca cgctcgatgt ggagcctagc    60
gacaccatcg agaacgtgaa gagcaagatc caggacaagg agggcatccc gcccgaccag   120
cagcgcctca tctttgccgg caagcagctc gaggacggtc gcacactcag cgactacaac   180
atccagaagg agtccacgct ccacctagtc ctgcgcctgc gcggtggcaa ctaagctatc   240
tgtagtatgt gctatactcg aatcatgctg ccctgtac                           278
```

<210> SEQ ID NO 17
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 17

```
caggactagg tggagcgtgg a                                              21
```

<210> SEQ ID NO 18
<211> LENGTH: 26
<212> TYPE: DNA
<213> ORGANISM: Artificial Sequence
<220> FEATURE:
<223> OTHER INFORMATION: Chemically synthesized primer

<400> SEQUENCE: 18

```
actccttctg gatgttgtag tcgctg                                         26
```

<210> SEQ ID NO 19
<211> LENGTH: 260
<212> TYPE: DNA
<213> ORGANISM: Thraustochytrium aureum

<400> SEQUENCE: 19

```
accccaaac gacaagcaga acaagcaaca ccagcagcag caagcgaccc aagcaacact     60
agccaacatg cagatcttcg tcaagacgct cacgggcaag accatcacgc tcgatgtgga   120
gcctagcgac accatcgaga acgtgaagag caagatccag gacaaggagg gcatcccgcc   180
cgaccagcag cgcctcatct tgccggcaa gcagctcgag gacggtcgca cactcagcga   240
ctacaacatc cagaaggagt                                               260
```

<210> SEQ ID NO 20
<211> LENGTH: 76
<212> TYPE: PRT
<213> ORGANISM: Thraustochytrium aureum

<400> SEQUENCE: 20

```
Met Gln Ile Phe Val Lys Thr Leu Thr Gly Lys Thr Ile Thr Leu Glu
1               5                   10                  15
Val Glu Gly Ser Asp Asn Ile Glu Asn Val Lys Ala Lys Ile Gln Asp
            20                  25                  30
Lys Glu Gly Ile Pro Pro Asp Gln Gln Arg Leu Ile Phe Ala Gly Lys
        35                  40                  45
Gln Leu Glu Asp Gly Arg Thr Leu Ser Asp Tyr Asn Ile Gln Lys Glu
    50                  55                  60
Ser Thr Leu His Leu Val Leu Arg Leu Arg Gly Gly
65                  70                  75
```

<210> SEQ ID NO 21

<211> LENGTH: 228
<212> TYPE: DNA
<213> ORGANISM: Thraustochytrium aureum

<400> SEQUENCE: 21

```
atgcagatct tcgtcaagac gctcacgggc aagaccatca cgctcgatgt ggagcctagc    60
gacaccatcg agaacgtgaa gagcaagatc caggacaagg agggcatccc gcccgaccag   120
cagcgcctca tctttgccgg caagcagctc gaggacggtc gcacactcag cgactacaac   180
atccagaagg agtccacgct ccacctagtc ctgcgcctgc gcggtggc               228
```

<210> SEQ ID NO 22
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 22

```
cacgttctcg atggtgtcgc t                                             21
```

<210> SEQ ID NO 23
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 23

```
gatctgcatg ttggctagtg ttgct                                         25
```

<210> SEQ ID NO 24
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 24

```
ctatactcga atcatgctgc cctg                                          24
```

<210> SEQ ID NO 25
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 25

```
aactaagcta tctgtagtat gtgc                                          24
```

<210> SEQ ID NO 26
<211> LENGTH: 801
<212> TYPE: DNA
<213> ORGANISM: Thraustochytrium aureum

<400> SEQUENCE: 26

```
cgttagaacg cgtaatacga ctcactatag ggagagtcga ctgagcacaa ctctgctgcg    60
agcgggcctc gagagcgttt gcttcgagcc gcggagcaag ggggatggat cgctcatgcg   120
gtcgtgcggc cctcggtcac ccggtgggtc ctgcactgac gcatctgttc tgatcagaca   180
cacgaacgaa caaaccgagg agccgcagcg cctggtgcac ccgccgggcg ttggttggtg   240
tgctatttac tatgcctacc gagagagaga gcggagcgga tgcataggaa atcgggccac   300
```

-continued

```
gcgggagggc catgcgttcg ccccacacgc cacttatacc acgcccgctc tctctccggc    360
cggcaggcag cgcataacta taccgacgct ggcaggcttg gtagcaactg gcagggacaa    420
ctcgcgcgcg ggtcccggtc gttcgatgtg ccaacccgag agaatccagc cagcagggcg    480
gttggcctca tcgcccacct gctatggtgc agcgaaccaa ctcccgaagc ggccggttcc    540
gcgattccct cttctgaatt ctgaattctg aactgattcc ggaggagaac cctctggaag    600
cgcgggttgc ctctccagtt ctgccgaact agacagggga gtgagcatga tgagtgaccc    660
tgacgcgtga gctgagctgg ttgctggaat atagtcgctg aacgctgggc tgtgtcacgc    720
gtccacttcg ggcagacccc aaacgacaag cagaacaagc aacaccagca gcagcaagcg    780
acctaagcaa cactagccaa c                                              801
```

<210> SEQ ID NO 27
<211> LENGTH: 584
<212> TYPE: DNA
<213> ORGANISM: Thraustochytrium aureum

<400> SEQUENCE: 27

```
aactaagcta tctgtagtat gtgctatact cgaatcatgc tgccctgtac gtacctacct     60
atatctgatt gagcgtgctg cgtcgaccat agacgcggga acgcgggcca gcctaccacg    120
ttgccgccgc cggtatccac gggcacgcca aagcattggt cgataacgct ctgcccaggg    180
cttcctggcg aggacccgag gccaacatgc atgcatgtgc tatcagcggt catcatcgcc    240
ctcatcagcg cgcatcggcg agctcgcgca cgaacggcaa cgcccaact caactcactt    300 actcacacta tggtcttgcc gttggcggtt gcttagctaa tgcgtgacgt cactctgcct    360
ccaacatcgc gaggcagagt cgcgagcagt gcagaggcca cggcggacgc caacaaagcg    420
ccaaccagcg caacgcacca gcgggtctgt gggcgtagct cgagcgggcg tcttcaagag    480
ccgccgtgga gccgacgccc ctgcgaaggg ctcgagtgca agcggggccg ttgagccgcg    540
tggtaggaac aactgcagtc tccctatagt gagtcgtatt acgc                    584
```

<210> SEQ ID NO 28
<211> LENGTH: 795
<212> TYPE: DNA
<213> ORGANISM: Artificial Sequence
<220> FEATURE:
<223> OTHER INFORMATION: Synthesized Neomaycin resistance DNA

<400> SEQUENCE: 28

```
atgattgaac aggacggcct tcacgctggc tcgcccgctg cttgggtgga acggctgttc     60
ggctacgact gggctcagca gacgatcggc tgctcggacg cggccgtgtt ccgccttagc    120
gcgcagggcg ggccggtcct gtttgtcaag accgacctta gcgcgcccct caacgagctc    180
caggacgaag ctgcccgcct cagctggctt gccacgacgg gggttccgtg cgccgctgtg    240
ctcgacgtcg tcaccgaagc cggcgcgac tggctgctcc tcgggaagt gcccggccag    300 gacctcctca gcagccacct cgcgcccgct gagaaggtgt ccatcatggc cgacgccatg    360
cgccgcctgc acaccctcga ccccgccacc tgcccttcg accaccaggc gaagcacagg    420
atcgaacgcg cccgcacgcg gatggaggct ggcctcgtcg accaagacga cctcgacgag    480
gagcaccagg gcctcgcgcc ggcggaactg ttcgccaggc ttaaggctag gatgccggac    540
ggcgaggacc tcgtggtcac gcacggcgac gcctgcctcc ccaacatcat ggtcgagaac    600
ggccgcttct cgggctttat cgactgcggg cgcctgggcg tggcggaccg ctaccaagac    660
```

```
atcgcgctcg ccacgcggga catcgccgag gagcttggcg gcgagtgggc cgaccgcttt      720
ctcgtgctct acggcatcgc cgccccggac agccagagga ttgcgttcta ccgcctcctg      780
gacgagttct tttga                                                      795
```

```
<210> SEQ ID NO 29
<211> LENGTH: 264
<212> TYPE: PRT
<213> ORGANISM: Artificial Sequence
<220> FEATURE:
<223> OTHER INFORMATION: AA coding Neomycin resistance DNA

<400> SEQUENCE: 29
```

| | | | | | | | | | | | | | | | |
|---|---|---|---|---|---|---|---|---|---|---|---|---|---|---|---|
| Met | Ile | Glu | Gln | Asp | Gly | Leu | His | Ala | Gly | Ser | Pro | Ala | Ala | Trp | Val |
| 1 | | | | 5 | | | | | 10 | | | | | 15 | |
| Glu | Arg | Leu | Phe | Gly | Tyr | Asp | Trp | Ala | Gln | Gln | Thr | Ile | Gly | Cys | Ser |
| | | | 20 | | | | | 25 | | | | | 30 | | |
| Asp | Ala | Ala | Val | Phe | Arg | Leu | Ser | Ala | Gln | Gly | Arg | Pro | Val | Leu | Phe |
| | | 35 | | | | | 40 | | | | | 45 | | | |
| Val | Lys | Thr | Asp | Leu | Ser | Gly | Ala | Leu | Asn | Glu | Leu | Gln | Asp | Glu | Ala |
| | 50 | | | | | 55 | | | | | 60 | | | | |
| Ala | Arg | Leu | Ser | Trp | Leu | Ala | Thr | Thr | Gly | Val | Pro | Cys | Ala | Ala | Val |
| 65 | | | | | 70 | | | | | 75 | | | | | 80 |
| Leu | Asp | Val | Val | Thr | Glu | Ala | Gly | Arg | Asp | Trp | Leu | Leu | Leu | Gly | Glu |
| | | | | 85 | | | | | 90 | | | | | 95 | |
| Val | Pro | Gly | Gln | Asp | Leu | Leu | Ser | Ser | His | Leu | Ala | Pro | Ala | Glu | Lys |
| | | | 100 | | | | | 105 | | | | | 110 | | |
| Val | Ser | Ile | Met | Ala | Asp | Ala | Met | Arg | Arg | Leu | His | Thr | Leu | Asp | Pro |
| | | 115 | | | | | 120 | | | | | 125 | | | |
| Ala | Thr | Cys | Pro | Phe | Asp | His | Gln | Ala | Lys | His | Arg | Ile | Glu | Arg | Ala |
| | 130 | | | | | 135 | | | | | 140 | | | | |
| Arg | Thr | Arg | Met | Glu | Ala | Gly | Leu | Val | Asp | Gln | Asp | Leu | Asp | Glu |
| 145 | | | | | 150 | | | | | 155 | | | | | 160 |
| Glu | His | Gln | Gly | Leu | Ala | Pro | Ala | Glu | Leu | Phe | Ala | Arg | Leu | Lys | Ala |
| | | | 165 | | | | | 170 | | | | | 175 | | |
| Arg | Met | Pro | Asp | Gly | Glu | Asp | Leu | Val | Val | Thr | His | Gly | Asp | Ala | Cys |
| | | 180 | | | | | 185 | | | | | 190 | | | |
| Leu | Pro | Asn | Ile | Met | Val | Glu | Asn | Gly | Arg | Phe | Ser | Gly | Phe | Ile | Asp |
| | 195 | | | | | 200 | | | | | 205 | | | | |
| Cys | Gly | Arg | Leu | Gly | Val | Ala | Asp | Arg | Tyr | Gln | Asp | Ile | Ala | Leu | Ala |
| 210 | | | | | 215 | | | | | 220 | | | | | |
| Thr | Arg | Asp | Ile | Ala | Glu | Leu | Gly | Gly | Glu | Trp | Ala | Asp | Arg | Phe |
| 225 | | | | | 230 | | | | | 235 | | | | | 240 |
| Leu | Val | Leu | Tyr | Gly | Ile | Ala | Ala | Pro | Asp | Ser | Gln | Arg | Ile | Ala | Phe |
| | | | 245 | | | | | 250 | | | | | 255 | | |
| Tyr | Arg | Leu | Leu | Asp | Glu | Phe | Phe |
| | | 260 | | | | | |

```
<210> SEQ ID NO 30
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 30
cgaatattcc tggttgatcc tgccagtagt                                       30
```

<210> SEQ ID NO 31
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 31
gtaacggctt tttttgaatt gcaggttcac tacgcttgtt agaaac                46

<210> SEQ ID NO 32
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 32
ggtttccgta gtgaacctgc aattcaaaaa aagccgttac tcacat                46

<210> SEQ ID NO 33
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 33
cactgcagcg aaagacgggc cgtaaggacg                                  30

<210> SEQ ID NO 34
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 34
cagcggcaaa ggaaggctag atgattgaac aagatggatt gcacgc                46

<210> SEQ ID NO 35
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 35
catcggcaaa ggaaggctag atgattgaac aggacggcct tcacg                 45

<210> SEQ ID NO 36
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 36
gcgcatagcc ggcgcggatc tcaaaagaac tcgtccagga ggcggt                46

<210> SEQ ID NO 37
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 37

```
tcctggacga gttctttga gatccgcgcc ggctatgcgc ccgtgc          46
```

<210> SEQ ID NO 38
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 38

```
cactgcagcg aaagacgggc cgtaaggacg          30
```

<210> SEQ ID NO 39
<211> LENGTH: 4454
<212> TYPE: DNA
<213> ORGANISM: Artificial Sequence
<220> FEATURE:
<223> OTHER INFORMATION: Synthesized DNA

<400> SEQUENCE: 39

```
cgaatattcc tggttgatcc tgccagtagt catacgctta tctcaaagat taagccatgc     60
atgtctaagt ataaaggctt atactctgaa actgcgaacg gctcattata tcagttatag    120
tttctttgat agtgtttttt ctacatggat acttgtggca atctagaaa caatacatgc     180
gtacaggcct gactttgggg gagggctgca tttatttgac ttaagccaat acccctcggg    240
gttgttttgg tgattcagaa taactgagcg aatcgcatag ctttcgggcg gcgatgaatc    300
atttcaagtt tctgccccat cagctgtcga tggtagggta taggcctacc atggctgtca    360
cgggtgacgg agaattaggg ttcgattccg gagagggagc tgagagacg gctaccacat     420
ccaaggaagg cagcaggcgc gtaaattact caatgttgac tcgacgaagt agtgacgaga    480
attaacaatg cggagcgctc agcgttttgc aattggaatg agagcaatgt aaaagcctca    540
tcgaggatcc attggagggc aagtctggtg ccagcagccg cggtaattcc agctccaata    600
gcgtatacta aagttgttgc agttaaaaag ctcgtagttg aacctctggt agggccgacc    660
ttggcgcgcg gtgaatgccg cgtcgtttag aagcgtcgtg cccggccatc ctcccccggt    720
ctttgggct gggggtcgtt tactgtaaaa aaatagagt gttccaagca gggggtaata     780
tcccggtata tagtagtatg gaataatgag ataggacttt ggtactattt tgttggtttg    840
catgccaagg taatgattaa gagggacagt tgggggtatt cgtatttaga tgtcagaggt    900
gaaattcttg gattttcgaa agacgaacta ctgcgaaagc atttaccaag gatgttttca    960
ttaatcaaga acgaaagtta ggggatcgaa gatgattaga taccatcgta gtcttaaccg   1020
taaactatgc cgacttgcga ttgtccggcg tcgcttttag atgacctggg cagcagcaca   1080
tgagaaatca aagtctttgg gttccggggg gagtatggtc gcaaggctga aacttaaagg   1140
aattgacgga agggcaccac caggagtgga gcctgcggct taatttgact caacacggga   1200
aaacttacca ggtccggaca taggaaggat tgacagattg agagctcttt cttgattcta   1260
tgggtggtgg tgcatggccg ttcttagttg gtggagtgat ttgtctggtt aattccgtta   1320
acgaacgaga ccacagccta ctaaatagtg gccgttatgg cgacatagcg gtgaacttct   1380
tagagggaca tttcgggtat accggaagga agtttgtggc aataacaggt ctgtgatgcc   1440
cttagatgtt ctgggccgca cgcgcgctac actgatcggt tcaacgagta tttgtttttt   1500
tctcattttg ggaggggggca gagtccttgg ccggaaggtc tgggtaatct tttgaatgcc   1560
```

```
gatcgtgatg gggctagatt tttgcaatta ttaatctcca acgaggaatt cctagtagac    1620
gcaagtcatc agcttgcatc gattacgtcc ctgccctttg tacacaccgc ccgtcgcacc    1680
taccgattga acgatccggt gagaccttgg gattctgttg tggctgattc attttggctg    1740
cgatgggaga acttgagcaa accttatcgt ttagaggaag gtgaagtcgt aacaaggttt    1800
ccgtagtgaa cctgcaattc aaaaaaagcc gttactcaca tcaggccgcc actcatccgg    1860
gcgaaagctt cgcgcattcg tcctcgtcac ctcgggtccc ctgtgtcgtg acggaaagcg    1920
cgacgagacg cggccgcagc agagagcccc gggggcccgc gtcacggggg gcctggcggc    1980
ggtcctcctt aagccaaacc gagggttagg gctccaggct gttcggcggg gtcgcgggcg    2040
cggtggacgc gcgggccgc ctagcacctc ctagcgcgcg actaccagga tagcccccgc    2100
gagtgcgcag ggcggtccgc ggggcggagg gcggcccagc agcgcggcgc ggcgggcggg    2160
tgcggctgcg taaggtggcg gcgggcgcgg gcggttagtg ttggtgttag gtcgcggcgg    2220
ggctgtgttc cgggcatccg ccttacggcg gtgcatactg gttggctggg aggcggtttg    2280
cggggttaga taggcggcca aggtgagctg cgttgggcgg ataaatccgt ggaggcgctc    2340
gttgacggcg cggcagagac ggaacgcgga gcagcacgga gtagcaagca ggagtagcag    2400
gagtagcaag cagcggcaaa ggaaggctag atgattgaac aggacggcct tcacgctggc    2460
tcgcccgctg cttgggtgga acggctgttc ggctacgact gggctcagca gacgatcggc    2520
tgctcggacg cggccgtgtt ccgccttagc gcgcagggcc ggccggtcct gtttgtcaag    2580
accgacctta gcggcgccct caacgagctc caggacgaag ctgcccgcct cagctggctt    2640
gccacgacgg gggttccgtg cgccgctgtg ctcgacgtcg tcaccgaagc cggccgcgac    2700
tggctgctcc tcggggaagt gcccggccag gacctcctca gcagccacct cgcgcccgct    2760
gagaaggtgt ccatcatggc cgacgccatg cgccgcctgc acaccctcga ccccgccacc    2820 tgcccctttcg accaccaggc gaagcacagg atcgaacgcg cccgcacgcg gatggaggct    2880
ggcctcgtcg accaagacga cctcgacgag gagcaccagg gcctcgcgcc ggcggaactg    2940
ttcgccaggc ttaaggctag gatgccggac ggcgaggacc tcgtggtcac gcacggcgac    3000
gcctgcctcc ccaacatcat ggtcgagaac ggccgcttct cgggctttat cgactgcggg    3060
cgcctgggcg tggcggaccg ctaccaagac atcgcgctcg ccacgcggga catcgccgag    3120
gagcttggcg gcgagtgggc cgaccgcttt ctcgtgctct acggcatcgc cgccccggac    3180
agccagagga ttgcgttcta ccgcctcctg gacgagttct tttgagatcc gcgccggcta    3240
tgcgcccgtg ctcgactgcc acactgccca cattgcctgc aagttcgctg agctccagaa    3300
caagatggac cgccgctcgg gcaagattct cgaggagacc cccaagttca tcaagtcggg    3360
tggactctgc catggtcaag atgtatcccc tccaagcgca tgtgcgtcga gtccttcacc    3420
gagtacccgc cgctcggccg ctttgccgtg cgcgacatgc gcgtcaccgt cgctgtcggc    3480
gtcatcaagt ccgtcaccaa gggcgacaaa taaattctac gaaagatttt tttcctcaag    3540
aagcgcccta agttgacccc ctagcagcga cgactgtgtg tgccgttgtg agtcgagttg    3600
cgatgtcgtg cagcgcccgt cgcgtcccat gctcgcgcgc gactccgtct ctgcttttca    3660
tctcaagtca agagtgggaa gttccctttgc tttatctcac tatttagagg tcgctcacgg    3720
ctgctggttc ctcgtcgcat gtagcacagc ctcgtccaat cgcagcctgc accaccccgc    3780
tcgcctggga aaatgcgctc agcggattcg cactggcact cctctcctcg gacaggtgcg    3840
atgtggaagc ggtcacatcc tcggcgccct cggccacgcc agcatctgcg caatcgctct    3900
cctcgttctc agccgcaacc gcaggcaggc cgacgtcgtt tacctcggaa tccaccgagc    3960
```

```
atttcgagcc catcgcgctg gcgtccacct cgatcatacc ttctccatcg ccgtccgctg    4020
cggcttccga ttcttctgct gccgcaaccg cgacgtcggc ccccgtctcc tccgttcttt    4080
ccgatgccgg cgcagtggcc gcgccctctg ctcgaaccgg ctcgtgttca gcgtcagggc    4140
ctgcgcttga gctcgggcgg ctcttccgag tgatccggcc ccgcgaggca aggaatcggc    4200
ggctctggag tgtcggggca gccgctctca ctgccggtct ttggctggct gcctgtcctg    4260
cctcgcgttg gcctttgctt ttgcctaggc tttcgccttg gtgacggcgt ttgcctgctg    4320
cggcgacttg gcgcggccgc ggaatagcgc tcaaagtcc tgctcgaggc gccccagctc     4380
tgacttgatt tgcgaggtcc cggtggcatg agctccgctg ccctcgtcct tacggcccgt    4440
ctttcgctgc agtg                                                     4454
```

<210> SEQ ID NO 40
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 40
gccagtagtc atatgcttat ctcaaag                                         27

<210> SEQ ID NO 41
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 41
tcgtattacg cgttctaacg ccttgttacg acttcacctt cctct                     45

<210> SEQ ID NO 42
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 42
aaggtgaagt cgtaacaagg cgttagaacg cgtaatacga ctcact                    46

<210> SEQ ID NO 43
<211> LENGTH: 48
<212> TYPE: DNA
<213> ORGANISM: Artificial Sequence
<220> FEATURE:
<223> OTHER INFORMATION: Chemically synthesized primer

<400> SEQUENCE: 43
gtgcaatcca tcttgttcaa tcatgttggc tagtgttgct taggtcgc                  48

<210> SEQ ID NO 44
<211> LENGTH: 48
<212> TYPE: DNA
<213> ORGANISM: Artificial Sequence
<220> FEATURE:
<223> OTHER INFORMATION: Chemically synthesized primer

<400> SEQUENCE: 44
gcgacctaag caacactagc caacatgatt gaacaagatg gattgcac                  48

<210> SEQ ID NO 45
<211> LENGTH: 49
<212> TYPE: DNA
<213> ORGANISM: Artificial Sequence
<220> FEATURE:
<223> OTHER INFORMATION: Chemically synthesized primer

<400> SEQUENCE: 45
gagtatagca catactacag atagctcaga agaactcgtc aagaaggcg                49

<210> SEQ ID NO 46
<211> LENGTH: 49
<212> TYPE: DNA
<213> ORGANISM: Artificial Sequence
<220> FEATURE:
<223> OTHER INFORMATION: Chemically synthesized primer

<400> SEQUENCE: 46
gccttcttga cgagttcttc tgagctatct gtagtatgtg ctatactcg                49

<210> SEQ ID NO 47
<211> LENGTH: 28
<212> TYPE: DNA
<213> ORGANISM: Artificial Sequence
<220> FEATURE:
<223> OTHER INFORMATION: Chemically synthesized primer

<400> SEQUENCE: 47
cggggtaccg cgtaatacga ctcactat                                       28

<210> SEQ ID NO 48
<211> LENGTH: 29
<212> TYPE: DNA
<213> ORGANISM: Artificial Sequence
<220> FEATURE:
<223> OTHER INFORMATION: Chemically synthesized primer

<400> SEQUENCE: 48
tcggtacccg ttagaacgcg taatacgac                                      29

<210> SEQ ID NO 49
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 49
tcggtaccac cgcgtaatac gactcactat agggagactg cagtt                    45

<210> SEQ ID NO 50
<211> LENGTH: 32
<212> TYPE: DNA
<213> ORGANISM: Artificial Sequence
<220> FEATURE:
<223> OTHER INFORMATION: Chemically synthesized primer

<400> SEQUENCE: 50
agaggaaggt gaagtcgtaa caaggcgtta ga                                  32

<210> SEQ ID NO 51
<211> LENGTH: 35
<212> TYPE: DNA
<213> ORGANISM: Artificial Sequence
<220> FEATURE:
<223> OTHER INFORMATION: Chemically synthesized primer

<400> SEQUENCE: 51
aacagctatg accatgatta cgaattcgag ctcgg                              35

<210> SEQ ID NO 52
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 52
cagcggcaaa ggaaggctag atgattgaac aggacggcct tcacgc                 46

<210> SEQ ID NO 53
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 53
gcgcatagcc ggcgcggatc tcaaaagaac tcgtccagga ggcggt                 46

<210> SEQ ID NO 54
<211> LENGTH: 41
<212> TYPE: DNA
<213> ORGANISM: Artificial Sequence
<220> FEATURE:
<223> OTHER INFORMATION: Chemically synthesized primer

<400> SEQUENCE: 54
acctaagcaa cactagccaa catggtgagc aagggcgagg a                      41

<210> SEQ ID NO 55
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 55
agcacatact acagatagct tagttttact tgtacagctc gtcca                  45

<210> SEQ ID NO 56
<211> LENGTH: 29
<212> TYPE: DNA
<213> ORGANISM: Artificial Sequence
<220> FEATURE:
<223> OTHER INFORMATION: Chemically synthesized primer
<220> FEATURE:
<221> NAME/KEY: misc_feature
<222> LOCATION: (3)..(3)
<223> OTHER INFORMATION: n is inosine.
<220> FEATURE:
<221> NAME/KEY: misc_feature
<222> LOCATION: (9)..(9)
<223> OTHER INFORMATION: n is inosine.
<220> FEATURE:
<221> NAME/KEY: misc_feature
<222> LOCATION: (15)..(15)
<223> OTHER INFORMATION: n is inosine.
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)

<223> OTHER INFORMATION: n is inosine.

<400> SEQUENCE: 56
ggntggmgna thwsncaymg nacncayca           29

<210> SEQ ID NO 57
<211> LENGTH: 20
<212> TYPE: DNA
<213> ORGANISM: Artificial Sequence
<220> FEATURE:
<223> OTHER INFORMATION: Chemically synthesized primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is inosine.

<400> SEQUENCE: 57
ccrtartcnc krtcnayngt                     20

<210> SEQ ID NO 58
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 58
agcgtctagc gcatcttcct c                   21

<210> SEQ ID NO 59
<211> LENGTH: 19
<212> TYPE: DNA
<213> ORGANISM: Artificial Sequence
<220> FEATURE:
<223> OTHER INFORMATION: Chemically synthesized primer

<400> SEQUENCE: 59
acgttcacgt ccgtgtgct                      19

<210> SEQ ID NO 60
<211> LENGTH: 35
<212> TYPE: DNA
<213> ORGANISM: Artificial Sequence
<220> FEATURE:
<223> OTHER INFORMATION: Chemically synthesized primer

<400> SEQUENCE: 60
ttaagcttca aaatgtctcg tggaggaaac ctctc    35

<210> SEQ ID NO 61
<211> LENGTH: 31
<212> TYPE: DNA
<213> ORGANISM: Artificial Sequence
<220> FEATURE:
<223> OTHER INFORMATION: Chemically synthesized primer

<400> SEQUENCE: 61
gtctagattt agtcgtgcgc cttgtagaac a        31

```
<210> SEQ ID NO 62
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 62
ggtttccgta gtgaacctgc aattcaaaaa aagccgttac tcacat                    46

<210> SEQ ID NO 63
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 63
cctaagcaac actagccaac atgggtcgtg gaggaaacct ctcca                     45

<210> SEQ ID NO 64
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 64
atactacaga tagcttagtt ttagtcgtgc gccttgtaga acaca                     45

<210> SEQ ID NO 65
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 65
tactggaaga accagcacag caagcaccac                                      30

<210> SEQ ID NO 66
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 66
gcggaactgc ggcgccgtgg ggaagaggtg                                      30

<210> SEQ ID NO 67
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 67
cgccgtgggg aagaggtggt gctcgatctg                                      30

<210> SEQ ID NO 68
<211> LENGTH: 23
<212> TYPE: DNA
<213> ORGANISM: Artificial Sequence
<220> FEATURE:
<223> OTHER INFORMATION: Chemically synthesized primer
```

-continued

```
<400> SEQUENCE: 68
tgtcctgctt cctggttggt ctc                                          23

<210> SEQ ID NO 69
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 69
tctggaccct gtttctgcac ccgc                                         24

<210> SEQ ID NO 70
<211> LENGTH: 21
<212> TYPE: DNA
<213> ORGANISM: Artificial Sequence
<220> FEATURE:
<223> OTHER INFORMATION: Chemically synthesized primer

<400> SEQUENCE: 70
accgcaaagt tggtgaagat g                                            21

<210> SEQ ID NO 71
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 71
caaagccaaa ggtggccatg tagagac                                      27

<210> SEQ ID NO 72
<211> LENGTH: 31
<212> TYPE: DNA
<213> ORGANISM: Artificial Sequence
<220> FEATURE:
<223> OTHER INFORMATION: Chemically synthesized primer

<400> SEQUENCE: 72
cgaattcatg ggacgcggcg gcgaaggtca g                                 31

<210> SEQ ID NO 73
<211> LENGTH: 31
<212> TYPE: DNA
<213> ORGANISM: Artificial Sequence
<220> FEATURE:
<223> OTHER INFORMATION: Chemically synthesized primer

<400> SEQUENCE: 73
gctcgagttg ggtcgggata aaataaatgg c                                 31

<210> SEQ ID NO 74
<211> LENGTH: 26
<212> TYPE: DNA
<213> ORGANISM: Artificial Sequence
<220> FEATURE:
<223> OTHER INFORMATION: Chemically synthesized primer

<400> SEQUENCE: 74
atgcaratht tygtkaarac yytsac                                       26

<210> SEQ ID NO 75
<211> LENGTH: 26
```

```
<212> TYPE: DNA
<213> ORGANISM: Artificial Sequence
<220> FEATURE:
<223> OTHER INFORMATION: Chemically synthesized primer

<400> SEQUENCE: 75
actccttctg gatgttgtag tcgctg                                              26

<210> SEQ ID NO 76
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 76
gacctaagca acactagcca acatgattga acaggacggc cttca                         45

<210> SEQ ID NO 77
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 77
tatagcacat actacagata gctcaaaaga actcgtccag gaggcg                        46

<210> SEQ ID NO 78
<211> LENGTH: 22
<212> TYPE: DNA
<213> ORGANISM: Artificial Sequence
<220> FEATURE:
<223> OTHER INFORMATION: Chemically synthesized primer

<400> SEQUENCE: 78
cgttagaacg cgtaatacga ct                                                  22

<210> SEQ ID NO 79
<211> LENGTH: 20
<212> TYPE: DNA
<213> ORGANISM: Artificial Sequence
<220> FEATURE:
<223> OTHER INFORMATION: Chemically synthesized primer

<400> SEQUENCE: 79
cggggtaccg cgtaatacga                                                     20

<210> SEQ ID NO 80
<211> LENGTH: 34
<212> TYPE: DNA
<213> ORGANISM: Artificial Sequence
<220> FEATURE:
<223> OTHER INFORMATION: Chemically synthesized primer

<400> SEQUENCE: 80
cagatctgga tccgcgaaat gaccgaccaa gcga                                     34

<210> SEQ ID NO 81
<211> LENGTH: 24
<212> TYPE: DNA
<213> ORGANISM: Artificial Sequence
<220> FEATURE:
<223> OTHER INFORMATION: Chemically synthesized primer

<400> SEQUENCE: 81
```

```
acgcaattaa tgtgagatct agct                                            24
```

<210> SEQ ID NO 82
<211> LENGTH: 342
<212> TYPE: DNA
<213> ORGANISM: Artificial Sequence
<220> FEATURE:
<223> OTHER INFORMATION: SV40 terminator

<400> SEQUENCE: 82

```
cagatctgga tccgcgaaat gaccgaccaa gcgacgccca acctgccatc acgagatttc    60
gattccaccg ccgccttcta tgaaaggttg ggcttcggaa tcgttttccg ggacgccggc   120
tggatgatcc tccagcgcgg ggatctcatg ctggagttct tcgcccaccc caacttgttt   180
attgcagctt ataatggtta caaataaagc aatagcatca caaatttcac aaataaagca   240
ttttttttcac tgcattctag ttgtggtttg tccaaactca tcaatgtatc ttatcatgtc   300
tgtataccgt cgacctctag ctagatctca cattaattgc gt                      342
```

<210> SEQ ID NO 83
<211> LENGTH: 618
<212> TYPE: DNA
<213> ORGANISM: Artificial
<220> FEATURE:
<223> OTHER INFORMATION: genomic DNA (T. Aureum 34304 ubiquitin
      promoter)

<400> SEQUENCE: 83

```
cccagatctg ccgcagcgcc tggtgcaccc gccgggcgtt gttggtgtgc tcttcttgcc    60
tccgagagag agagcggagc ggatgcatag gaaatcgggc cacgcgggag ggccatgcgt   120
tcgccccaca cgccactttc cacgcccgct ctctctccgg ccggcaggca gcgcataact   180
ctccgacgct ggcaggctgg tagcaactgg cagggacaac tcgcgcgcgg gtcccggtcg   240
ttcgatgtgc caacccgaga gaatccagcc agcagggcgg ttggcctcat cgcccacctg   300
ctatggtgca gcgaaccaac tcccgaagcg gccggttctg cgattccctc ttctgaattc   360
tgaattctga actgattccg gaggagaacc ctctggaagc gcgggttgcc tctccagttc   420
tgccgaacta gacaggggag tgagcagaga gtgaccctga cgcggagcga gctggttgct   480
ggaaaagtcg cgaacgctgg gctgtgtcac gcgtccactt cgggcagtcc ccaaacgaca   540
agcagaacaa gcaacaccag cagcagcaag cgacctaagc aacactagcc aacatggcca   600
agcctttgtc tcaagaag                                                  618
```

<210> SEQ ID NO 84
<211> LENGTH: 36
<212> TYPE: DNA
<213> ORGANISM: Artificial Sequence
<220> FEATURE:
<223> OTHER INFORMATION: Chemically synthesized primer

<400> SEQUENCE: 84

```
cccagatctg ccgcagcgcc tggtgcaccc gccggg                              36
```

<210> SEQ ID NO 85
<211> LENGTH: 58
<212> TYPE: DNA
<213> ORGANISM: Artificial Sequence
<220> FEATURE:
<223> OTHER INFORMATION: Chemically synthesized primer

<400> SEQUENCE: 85

```
cttcttgaga caaaggcttg gccatgttgg ctagtgttgc ttaggtcgct tgctgctg        58
```

<210> SEQ ID NO 86
<211> LENGTH: 432
<212> TYPE: DNA
<213> ORGANISM: Artificial Sequence
<220> FEATURE:
<223> OTHER INFORMATION: Blasticidin resistance gene (Blar)

<400> SEQUENCE: 86

```
agcgacctaa gcaacactag ccaacatggc caagcctttg tctcaagaag aatccaccct        60
cattgaaaga gcaacggcta caatcaacag catccccatc tctgaagact acagcgtcgc       120
cagcgcagct ctctctagcg acggccgcat cttcactggt gtcaatgtat atcattttac       180
tgggggacct tgtgcagaac tcgtggtgct gggcactgct gctgctgcgg cagctggcaa       240
cctgacttgt atcgtcgcga tcggaaatga gaacagtggc atcttgagcc cctgcggacg       300
gtgccgacag gtgcttctcg atctgcatcc tgggatcaaa gccatagtga aggacagtga       360
tggacagccg acggcagttg ggattcgtga attgctgccc tctggttatg tgtgggaggg       420
ctaagatctg gg                                                           432
```

<210> SEQ ID NO 87
<211> LENGTH: 54
<212> TYPE: DNA
<213> ORGANISM: Artificial Sequence
<220> FEATURE:
<223> OTHER INFORMATION: Chemically synthesized primer

<400> SEQUENCE: 87

```
agcgacctaa gcaacactag ccaacatggc caagcctttg tctcaagaag aatc              54
```

<210> SEQ ID NO 88
<211> LENGTH: 38
<212> TYPE: DNA
<213> ORGANISM: Artificial Sequence
<220> FEATURE:
<223> OTHER INFORMATION: Chemically synthesized primer

<400> SEQUENCE: 88

```
cccagatctt agccctccca cacataacca gagggcag                                38
```

<210> SEQ ID NO 89
<211> LENGTH: 1000
<212> TYPE: DNA
<213> ORGANISM: Artificial Sequence
<220> FEATURE:
<223> OTHER INFORMATION: fusion DNA (T. Aureum 34304 ubiquitin
      promoter/pTracer-CMV/Bsd/LacZ Blar)

<400> SEQUENCE: 89

```
cccagatctg ccgcagcgcc tggtgcaccc gccgggcgtt gttggtgtgc tcttcttgcc        60
tccgagagag agagcggagc ggatgcatag gaaatcgggc cacgcgggag ggccatgcgt       120
tcgccccaca cgccactttc cacgcccgct ctctctccgg ccggcaggca gcgcataact       180
ctccgacgct ggcaggctgg tagcaactgg cagggacaac tcgcgcgcgg gtcccggtcg       240
ttcgatgtgc caacccgaga gaatccagcc agcagggcgg ttggcctcat cgcccacctg       300
ctatggtgca gcgaaccaac tcccgaagcg gccggttctg cgattccctc ttctgaattc       360
tgaattctga actgattccg gaggagaacc tctggaagc gcgggttgcc tctccagttc       420
tgccgaacta gacaggggag tgagcagaga gtgaccctga cgcggagcga gctggttgct       480
```

| | |
|---|---|
| ggaaaagtcg cgaacgctgg gctgtgtcac gcgtccactt cgggcagtcc ccaaacgaca | 540 |
| agcagaacaa gcaacaccag cagcagcaag cgacctaagc aacactagcc aacatggcca | 600 |
| agcctttgtc tcaagaagaa tccaccctca ttgaaagagc aacggctaca atcaacagca | 660 |
| tccccatctc tgaagactac agcgtcgcca gcgcagctct ctctagcgac ggccgcatct | 720 |
| tcactggtgt caatgtatat cattttactg ggggaccttg tgcagaactc gtggtgctgg | 780 |
| gcactgctgc tgctgcggca gctggcaacc tgacttgtat cgtcgcgatc ggaaatgaga | 840 |
| acagggcat cttgagcccc tgcggacggt gccgacaggt gcttctcgat ctgcatcctg | 900 |
| ggatcaaagc catagtgaag acagtgatg acagccgac ggcagttggg attcgtgaat | 960 |
| tgctgccctc tggttatgtg tgggagggct aagatctggg | 1000 |

<210> SEQ ID NO 90
<211> LENGTH: 812
<212> TYPE: DNA
<213> ORGANISM: Artificial Sequence
<220> FEATURE:
<223> OTHER INFORMATION: ubiquitin promoter

<400> SEQUENCE: 90

| | |
|---|---|
| tcggtacccg ttagaacgcg taatacgact cactataggg agagtcgact gagcacaact | 60 |
| ctgctgcgag cgggcctcga gagcgtttgc ttcgagccgc ggagcaaggg ggatggatcg | 120 |
| ctcatgcggt cgtgcggccc tcggtcaccc ggtgggtcct gcactgacgc atctgttctg | 180 |
| atcagacaca cgaacgaaca aaccgaggag ccgcagcgcc tggtgcaccc gccgggcgtt | 240 |
| gttgtgtgct cttcttgcct ccgagagaga gagcggagcg gatgcatagg aaatcgggcc | 300 |
| acgcgggagg gccatgcgtt cgccccacac gccactttcc acgcccgctc tctctccggc | 360 |
| cggcaggcag cgcataactc tccgacgctg gcaggctggt agcaactggc agggacaact | 420 |
| cgcgcgcggg tcccggtcgt cgatgtgcc aacccgagag aatccagcca gcagggcggt | 480 |
| tggcctcatc gcccacctgc tatggtgcag cgaaccaact cccgaagcgg ccggttctgc | 540 |
| gattccctct tctgaattct gaattctgaa ctgattccgg aggagaaccc tctggaagcg | 600 |
| cgggttgcct ctccagttct gccgaactag acaggggagt gagcagagag tgaccctgac | 660 |
| gcggagcgag ctggttgctg gaaaagtcgc gaacgctggg ctgtgtcacg cgtccacttc | 720 |
| gggcagaccc caaacgacaa gcagaacaag caacaccagc agcagcaagc gacctaagca | 780 |
| acactagcca acatgactga ggataagacg aa | 812 |

<210> SEQ ID NO 91
<211> LENGTH: 29
<212> TYPE: DNA
<213> ORGANISM: Artificial Sequence
<220> FEATURE:
<223> OTHER INFORMATION: Chemically synthesized primer

<400> SEQUENCE: 91

| | |
|---|---|
| tcggtacccg ttagaacgcg taatacgac | 29 |

<210> SEQ ID NO 92
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 92

| | |
|---|---|
| ttcgtcttat cctcagtcat gttggctagt gttgcttagg tcgct | 45 |

<210> SEQ ID NO 93
<211> LENGTH: 1116
<212> TYPE: DNA
<213> ORGANISM: Artificial Sequence
<220> FEATURE:
<223> OTHER INFORMATION: cDNA (Saprolegnia diclina omega3 desaturase)

<400> SEQUENCE: 93

```
cctaagcaac actagccaac atgactgagg ataagacgaa ggtcgagttc ccgacgctca      60
cggagctcaa gcactcgatc ccgaacgcgt gctttgagtc gaacctcggc ctctcgctct     120
actacacggc ccgcgcgatc ttcaacgcgt cggcctcggc ggcgctgctc tacgcggcgc     180
gctcgacgcc gttcattgcc gataacgttc tgctccacgc gctcgtttgc gccacctaca     240
tctacgtgca gggcgtcatc ttctggggct tcttcacggt cggccacgac tgcggccact     300
cggccttctc gcgctaccac agcgtcaact ttatcatcgg ctgcatcatg cactctgcga     360
ttttgacgcc gttcgagagc tggcgcgtga cgcaccgcca ccaccacaag aacacgggca     420
acattgataa ggacgagatc ttttacccgc accggtcggt caaggacctc caggacgtgc     480
gccaatgggt ctacacgctc ggcggtgcgt ggtttgtcta cttgaaggtc gggtatgccc     540
cgcgcacgat gagccacttt gacccgtggg acccgctcct ccttcgccgc cgtcggccg      600
tcatcgtgtc gctcggcgtc tgggccgcct cttcgccgc gtacgcgtac ctcacatact     660
cgctcggctt tgccgtcatg ggcctctact actatgcgcc gctctttgtc tttgcttcgt     720
tcctcgtcat tacgaccttc ttgcaccaca cgacgaagc gacgccgtgg tacggcgact     780
cggagtggac gtacgtcaag ggcaacctct cgagcgtcga ccgctcgtac ggcgcgttcg     840
tggacaacct gagccaccac attggcacgc accaggtcca ccacttgttc ccgatcattc     900
cgcactacaa gctcaacgaa gccaccaagc actttgcggc gcgtacccg cacctcgtgc     960
gcaagaacga cgagcccatc atctcggcct tcttcaagac cgcgcacctc tttgtcaact    1020
acggcgctgt gcccgagacg gcgcagatct tcacgctcaa agagtcggcc gcggccgcca   1080
aggccaagtc ggactaaact aagctatctg tagtat                               1116
```

<210> SEQ ID NO 94
<211> LENGTH: 43
<212> TYPE: DNA
<213> ORGANISM: Artificial Sequence
<220> FEATURE:
<223> OTHER INFORMATION: Chemically synthesized primer

<400> SEQUENCE: 94

```
cctaagcaac actagccaac atgactgagg ataagacgaa ggt                        43
```

<210> SEQ ID NO 95
<211> LENGTH: 40
<212> TYPE: DNA
<213> ORGANISM: Artificial Sequence
<220> FEATURE:
<223> OTHER INFORMATION: Chemically synthesized primer

<400> SEQUENCE: 95

```
atactacaga tagcttagtt ttagtccgac ttggccttgg                            40
```

<210> SEQ ID NO 96
<211> LENGTH: 614
<212> TYPE: DNA
<213> ORGANISM: Artificial Sequence
<220> FEATURE:

<223> OTHER INFORMATION: ubiquitin terminator

<400> SEQUENCE: 96

```
ccaaggccaa gtcggactaa actaagctat ctgtagtatg tgctatactc gaatcatgct      60
gccctgtacg tacctaccta tatctgattg agcgtgctgc gtcgaccata gacgcgggaa     120
cgcgggccag cctaccacgt tgccgccgcc ggtatccacg ggcacgccaa agcattggtc     180
gataacgctc tgcccagggc ttcctggcga ggacccgagg ccaacatgca tgcatgtgct     240
atcagcggtc atcatcgccc tcatcagcgc gcatcggcga gctcgcgcac gaacggcaag     300
cgcccaactc aactcactta ctcacactat ggtcttgccg ttggcggttg cttagctaat     360
gcgtgacgtc actctgcctc caacatcgcg aggcagagtc gcgagcagtg cagaggccac     420
ggcggacgcc aacaaagcgc caaccagcgc aacgcaccag cgggtctgtg ggcgtagctc     480
gagcgggcgt cttcaagagc cgccgtggag ccgacgcccc tgcgaagggc tcgagtgcaa     540
gcggggccgt tgagccgcgt ggtaggaaca actgcagtct ccctatagtg agtcgtatta     600
cgcggtggta ccga                                                       614
```

<210> SEQ ID NO 97
<211> LENGTH: 44
<212> TYPE: DNA
<213> ORGANISM: Artificial Sequence
<220> FEATURE:
<223> OTHER INFORMATION: Chemically synthesized primer

<400> SEQUENCE: 97

```
ccaaggccaa gtcggactaa aactaagcta tctgtagtat gtgc                      44
```

<210> SEQ ID NO 98
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 98

```
tcggtaccac cgcgtaatac gactcactat agggagactg cagtt                     45
```

<210> SEQ ID NO 99
<211> LENGTH: 2463
<212> TYPE: DNA
<213> ORGANISM: Artificial
<220> FEATURE:
<223> OTHER INFORMATION: fusion DNA (T. aureum ATCC 34304 ubiquitin
      promoter/Saprolegnia diclina omega3 desaturase/T. aureum
      ATCC 34304 ubiquitin terminator)

<400> SEQUENCE: 99

```
tcggtacccg ttagaacgcg taatacgact cactataggg agagtcgact gagcacaact      60
ctgctgcgag cgggcctcga gagcgtttgc ttcgagccgc ggagcaaggg ggatggatcg     120
ctcatgcggt cgtgcggccc tcggtcaccc ggtgggtcct gcactgacgc atctgttctg     180
atcagacaca cgaacgaaca aaccgaggag ccgcagcgcc tggtgcaccc gccgggcgtt     240
gttgtgtgct cttcttgcct ccgagagaga gagcggagcg gatgcatagg aaatcgggcc     300
acgcgggagg gccatgcgtt cgccccacac gccactttcc acgcccgctc tctctccggc     360
cggcaggcag cgcataactc tccgacgctg gcaggctggt agcaactggc agggacaact     420
cgcgcgcggg tcccggtcgt tcgatgtgcc aaccgagag  aatccagcca gcaggcggt     480
tggcctcatc gcccacctgc tatggtgcag cgaaccaact cccgaagcgg ccggttctgc     540
```

```
gattccctct tctgaattct gaattctgaa ctgattccgg aggagaaccc tctggaagcg    600
cgggttgcct ctccagttct gccgaactag acaggggagt gagcagagag tgaccctgac    660
gcggagcgag ctggttgctg aaaagtcgc gaacgctggg ctgtgtcacg cgtccacttc    720
gggcagaccc caaacgacaa gcagaacaag caacaccagc agcagcaagc gacctaagca    780
acactagcca acatgactga ggataagacg aaggtcgagt tcccgacgct cacggagctc    840
aagcactcga tcccgaacgc gtgctttgag tcgaacctcg gcctctcgct ctactacacg    900
gcccgcgcga tcttcaacgc gtcggcctcg gcggcgctgc tctacgcggc gcgctcgacg    960
ccgttcattg ccgataacgt tctgctccac gcgctcgttt gcgccaccta catctacgtg   1020
cagggcgtca tcttctgggg cttcttcacg gtcgccacg actgcggcca ctcggccttc   1080
tcgcgctacc acagcgtcaa ctttatcatc ggctgcatca tgcactctgc gattttgacg   1140
ccgttcgaga gctggcgcgt gacgcaccgc caccaccaca agaacacggg caacattgat   1200
aaggacgaga tcttttaccc gcaccggtcg gtcaaggacc tccaggacgt gcgccaatgg   1260
gtctacacgc tcggcggtgc gtggtttgtc tacttgaagg tcgggtatgc cccgcgcacg   1320
atgagccact ttgacccgtg ggacccgctc tccttcgcc gcgcgtcggc cgtcatcgtg   1380
tcgctcggcg tctgggccgc cttcttcgcc gcgtacgcgt acctcacata tcgctcggc   1440 tttgccgtca tgggcctcta ctactatgcg ccgctctttg tctttgcttc gttcctcgtc   1500
attacgacct tcttgcacca caacgacgaa gcgacgccgt ggtacggcga tcggagtgg   1560 acgtacgtca agggcaacct ctcgagcgtc gaccgctcgt acggcgcgtt cgtggacaac   1620
ctgagccacc acattggcac gcaccaggtc caccacttgt tcccgatcat tccgcactac   1680
aagctcaacg aagccaccaa gcactttgcg gccgcgtacc cgcacctcgt gcgcaagaac   1740
gacgagccca tcatctcggc cttcttcaag accgcgcacc tctttgtcaa ctacggcgct   1800
gtgcccgaga cggcgcagat cttcacgctc aaagagtcgg ccgcggccgc caaggccaag   1860
tcggactaaa ctaagctatc tgtagtatgt gctatactcg aatcatgctg ccctgtacgt   1920
acctacctat atctgattga gcgtgctgcg tcgaccatag acgcgggaac gcgggccagc   1980
ctaccacgtt gccgccgccg gtatccacgg gcacgccaaa gcattggtcg ataacgctct   2040
gcccagggct tcctggcgag gacccgaggc caacatgcat gcatgtgcta tcagcggtca   2100
tcatcgccct catcagcgcg catcggcgag ctcgcgcacg aacggcaagc gcccaactca   2160
actcacttac tcacactatg gtcttgccgt tggcggttgc ttagctaatg cgtgacgtca   2220
ctctgcctcc aacatcgcga ggcagagtcg cgagcagtgc agaggccacg gcggacgcca   2280
acaaagcgcc aaccagcgca acgcaccagc gggtctgtgg gcgtagctcg agcgggcgtc   2340
ttcaagagcc gccgtggagc cgacgcccct gcgaagggct cgagtgcaag cggggccgtt   2400
gagccgcgtg gtaggaacaa ctgcagtctc cctatagtga gtcgtattac gcggtggtac   2460
cga                                                                 2463
```

<210> SEQ ID NO 100
<211> LENGTH: 36
<212> TYPE: DNA
<213> ORGANISM: Artificial Sequence
<220> FEATURE:
<223> OTHER INFORMATION: Chemically synthesized primer

<400> SEQUENCE: 100
cccggtaccg ccgcagcgcc tggtgcaccc gccggg                              36

<210> SEQ ID NO 101
<211> LENGTH: 3777
<212> TYPE: DNA
<213> ORGANISM: Artificial Sequence
<220> FEATURE:
<223> OTHER INFORMATION: fusion DNA (ubiquitin promoter/omega3 desaturase/ubiquitin terminator/ubiquitin promoter/Blar/SV40 terminator)

<400> SEQUENCE: 101

```
tcggtacccg ttagaacgcg taatacgact cactataggg agagtcgact gagcacaact      60
ctgctgcgag cgggcctcga gagcgtttgc ttcgagccgc ggagcaaggg ggatggatcg     120
ctcatgcggt cgtgcggccc tcggtcaccc ggtgggtcct gcactgacgc atctgttctg     180
atcagacaca cgaacgaaca aaccgaggag ccgcagcgcc tggtgcaccc gccgggcgtt     240
gttgtgtgct cttcttgcct ccgagagaga gagcggagcg gatgcatagg aaatcgggcc     300
acgcgggagg gccatgcgtt cgccccacac gccactttcc acgcccgctc tctctccggc     360
cggcaggcag cgcataactc tccgacgctg gcaggctggt agcaactggc agggacaact     420
cgcgcgcggg tcccggtcgt tcgatgtgcc aacccgagag aatccagcca gcagggcggt     480
tggcctcatc gcccacctgc tatggtgcag cgaaccaact cccgaagcgg ccggttctgc     540
gattccctct tctgaattct gaattctgaa ctgattccgg aggagaaccc tctggaagcg     600
cgggttgcct ctccagttct gccgaactag acaggggagt gagcagagag tgaccctgac     660
gcggagcgag ctggttgctg aaaagtcgc  gaacgctggg ctgtgtcacg cgtccacttc     720
gggcagaccc caaacgacaa gcagaacaag caacaccagc agcagcaagc gacctaagca     780
acactagcca acatgactga ggataagacg aaggtcgagt tcccgacgct cacggagctc     840
aagcactcga tcccgaacgc gtgctttgag tcgaacctcg gcctctcgct ctactacacg     900
gcccgcgcga tcttcaacgc gtcggcctcg gcggcgctgc tctacgcggc gcgctcgacg     960
ccgttcattg ccgataacgt tctgctccac gcgctcgttt gcgccaccta catctacgtg    1020
cagggcgtca tcttctgggg cttcttcacg gtcggccacg actgcggcca ctcggccttc    1080
tcgcgctacc acagcgtcaa cttttatcatc ggctgcatca tgcactctgc gattttgacg    1140
ccgttcgaga gctggcgcgt gacgcaccgc caccaccaca agaacacggg caacattgat    1200
aaggacgaga tcttttaccc gcaccggtcg gtcaaggacc tccaggacgt gcgccaatgg    1260
gtctacacgc tcggcggtgc gtggtttgtc tacttgaagg tcgggtatgc cccgcgcacg    1320
atgagccact ttgacccgtg ggacccgctc tccttcgcc  gcgcgtcggc cgtcatcgtg    1380
tcgctcggcg tctgggccgc cttcttcgcc gcgtacgcgt acctcacata tcgctcggc     1440
tttgccgtca tgggcctcta ctactatgcg ccgctctttg tctttgcttc gttcctcgtc    1500
attacgacct tcttgcacca caacgacgaa gcgacgccgt ggtacggcga tcggagtgg    1560
acgtacgtca agggcaacct ctcgagcgtc gaccgctcgt acggcgcgtt cgtggacaac    1620
ctgagccacc acattggcac gcaccaggtc caccacttgt tcccgatcat tccgcactac    1680
aagctcaacg aagccaccaa gcactttgcg gccgcgtacc cgcacctcgt gcgcaagaac    1740
gacgagccca tcatctcggc cttcttcaag accgcgcacc tctttgtcaa ctacggcgct    1800
gtgcccgaga cggcgcagat cttcacgctc aaagagtcgg ccgcggccgc caaggccaag    1860
tcggactaaa ctaagctatc tgtagtatgt gctatactcg aatcatgctg ccctgtacgt    1920
acctacctat atctgattga gcgtgctgcg tcgaccatag acgcgggaac gcgggccagc    1980
ctaccacgtt gccgccgccg gtatccacgg gcacgccaaa gcattggtcg ataacgctct    2040
```

```
gcccagggct tcctggcgag gacccgaggc caacatgcat gcatgtgcta tcagcggtca      2100
tcatcgccct catcagcgcg catcggcgag ctcgcgcacg aacggcaagc gcccaactca      2160
actcacttac tcacactatg gtcttgccgt tggcggttgc ttagctaatg cgtgacgtca      2220
ctctgcctcc aacatcgcga ggcagagtcg cgagcagtgc agaggccacg gcggacgcca      2280
acaaagcgcc aaccagcgca acgcaccagc gggtctgtgg gcgtagctcg agcgggcgtc      2340
ttcaagagcc gccgtggagc cgacgcccct gcgaagggct cgagtgcaag cggggccgtt      2400
gagccgcgtg gtaggaacaa ctgcagtctc cctatagtga gtcgtattac gcggtggtac      2460
cgccgcagcg cctggtgcac ccgccgggcg ttgttgtgtg ctcttcttgc ctccgagaga      2520
gagagcggag cggatgcata ggaaatcggg ccacgcggga gggccatgcg ttcgcccac       2580 acgccacttt ccacgcccgc tctctctccg gccggcaggc agcgcataac tctccgacgc      2640
tggcaggctg gtagcaactg gcagggacaa ctcgcgcgcg ggtcccggtc gttcgatgtg      2700
ccaacccgag agaatccagc cagcagggcg gttggcctca tcgcccacct gctatggtgc      2760
agcgaaccaa ctcccgaagc ggccggttct gcgattccct cttctgaatt ctgaattctg      2820
aactgattcc ggaggagaac cctctggaag cgcgggttgc ctctccagtt ctgccgaact      2880
agacagggga gtgagcagag agtgaccctg acgcggagcg agctggttgc tggaaaagtc      2940
gcgaacgctg ggctgtgtca cgcgtccact tcgggcagtc cccaaacgac aagcagaaca      3000
agcaacacca gcagcagcaa gcgacctaag caacactagc caacatggcc aagcctttgt      3060
ctcaagaaga atccaccctc attgaaagag caacggctac aatcaacagc atccccatct      3120
ctgaagacta cagcgtcgcc agcgcagctc tctctagcga cggccgcatc ttcactggtg      3180
tcaatgtata tcattttact gggggacctt gtgcagaact cgtggtgctg ggcactgctg      3240
ctgctgcggc agctggcaac ctgacttgta tcgtcgcgat cggaaatgag aacagggggca     3300 tcttgagccc ctgcgacgg tgccgacagg tgcttctcga tctgcatcct gggatcaaag      3360
ccatagtgaa ggacagtgat ggacagccga cggcagttgg gattcgtgaa ttgctgccct      3420
ctggttatgt gtgggagggc taagatccgg gaaatgaccg accaagcgac gcccaacctg      3480
ccatcacgag atttcgattc caccgccgcc ttctatgaaa ggttgggctt cggaatcgtt      3540
ttccgggacg ccggctggat gatcctccag cgcggggatc tcatgctgga gttcttcgcc      3600 cacccccaact tgtttattgc agcttataat ggttacaaat aaagcaatag catcacaaat      3660
ttcacaaata aagcattttt tcactgcat tctagttgtg gtttgtccaa actcatcaat      3720
gtatcttatc atgtctgtat accgtcgacc tctagctaga tctcacatta attgcgt       3777
```

<210> SEQ ID NO 102
<211> LENGTH: 41
<212> TYPE: DNA
<213> ORGANISM: Artificial Sequence
<220> FEATURE:
<223> OTHER INFORMATION: Chemically synthesized primer

<400> SEQUENCE: 102

```
tcctcgccct tgctcaccat gttggctagt gttgcttagg t                          41
```

<210> SEQ ID NO 103
<211> LENGTH: 45
<212> TYPE: DNA
<213> ORGANISM: Artificial Sequence
<220> FEATURE:
<223> OTHER INFORMATION: Chemically synthesized primer

```
<400> SEQUENCE: 103
tggacgagct gtacaagtaa aactaagcta tctgtagtat gtgct         45

<210> SEQ ID NO 104
<211> LENGTH: 37
<212> TYPE: DNA
<213> ORGANISM: Artificial Sequence
<220> FEATURE:
<223> OTHER INFORMATION: Chemically synthesized primer

<400> SEQUENCE: 104
atctagaacc gcgtaatacg actcactata gggagac                  37

<210> SEQ ID NO 105
<211> LENGTH: 30
<212> TYPE: DNA
<213> ORGANISM: Artificial Sequence
<220> FEATURE:
<223> OTHER INFORMATION: Chemically synthesized primer

<400> SEQUENCE: 105
cgaatattcc tggttgatcc tgccagtagt                          30

<210> SEQ ID NO 106
<211> LENGTH: 46
<212> TYPE: DNA
<213> ORGANISM: Artificial Sequence
<220> FEATURE:
<223> OTHER INFORMATION: Chemically synthesized primer

<400> SEQUENCE: 106
gtaacggctt tttttgaatt gcaggttcac tacggaaacc ttgtta        46

<210> SEQ ID NO 107
<211> LENGTH: 47
<212> TYPE: DNA
<213> ORGANISM: Artificial Sequence
<220> FEATURE:
<223> OTHER INFORMATION: Chemically synthesized primer

<400> SEQUENCE: 107
aaggccgtcc tgttcaatca tctagccttc ctttgccgct gcttgct       47

<210> SEQ ID NO 108
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 108
aggtttcctc cacgacccat gttggctagt gttgcttagg tcgct         45

<210> SEQ ID NO 109
<211> LENGTH: 45
<212> TYPE: DNA
<213> ORGANISM: Artificial Sequence
<220> FEATURE:
<223> OTHER INFORMATION: Chemically synthesized primer

<400> SEQUENCE: 109
tctacaaggc gcacgactaa aactaagcta tctgtagtat gtgct         45

<210> SEQ ID NO 110
<211> LENGTH: 30
```

```
<212> TYPE: DNA
<213> ORGANISM: Artificial Sequence
<220> FEATURE:
<223> OTHER INFORMATION: Chemically synthesized primer

<400> SEQUENCE: 110
cgcggtgggc accggtgtct gggtcatcgc                                        30

<210> SEQ ID NO 111
<211> LENGTH: 29
<212> TYPE: DNA
<213> ORGANISM: Artificial Sequence
<220> FEATURE:
<223> OTHER INFORMATION: Chemically synthesized primer

<400> SEQUENCE: 111
acaccggtgc ccaccgcgcc ctgccagaa                                         29

<210> SEQ ID NO 112
<211> LENGTH: 437
<212> TYPE: PRT
<213> ORGANISM: Pinguiochrysis pyriformis

<400> SEQUENCE: 112

Met Gly Arg Gly Gly Asn Leu Ser Ser Thr Ala Ala Lys Ala Val Ser
1               5                   10                  15

Lys Arg Thr Ala Glu Thr Glu Arg Ser Met Lys Arg Met Glu His Leu
            20                  25                  30

Ser Asp Ala Glu Leu Arg Lys Ala Ala Thr Leu Arg Gly Leu Ala Asp
        35                  40                  45

Ala Gly Asp Arg Glu Glu Leu Leu Glu Thr Leu Ala Pro Phe Ala Ala
    50                  55                  60

Gly Val Leu Asp Lys Arg Thr Gln His Thr Met Pro Leu Lys Trp Pro
65                  70                  75                  80

Ala Pro Phe Thr Phe Gly Asp Ile Lys Lys Ala Ile Pro Arg His Cys
                85                  90                  95

Phe Gln Arg Ser Ala Val Lys Ser Phe Met His Leu Ser Val Asp Leu
            100                 105                 110

Ala Met Val Ala Ala Met Ala Tyr Gly Ala Ser Phe Ile Asp Gly Ser
        115                 120                 125

Glu Leu Ala Gly Trp Gln Lys Phe Leu Ala Trp Ser Thr Tyr Trp Phe
    130                 135                 140

Trp Gln Gly Ala Val Gly Thr Gly Val Met Val Ile Ala His Glu Cys
145                 150                 155                 160

Gly His Gln Ala Phe Ser Pro Ser Lys Phe Ile Asn Asp Ser Val Gly
                165                 170                 175

Trp Val Leu His Ser Ala Leu Leu Val Pro Tyr His Ser Trp Arg Ile
            180                 185                 190

Ser His Arg Asn His His Ser Asn Thr Gly Ser Cys Glu Asn Asp Glu
        195                 200                 205

Val Phe Cys Pro Ala Arg Arg Asp Asp Tyr Val Glu Pro His Gly Glu
    210                 215                 220

Leu Met Arg Asp Val Pro Leu Tyr Ser Val Trp Arg Ile Phe Leu Met
225                 230                 235                 240

Leu Thr Phe Gly Trp Met Pro Gly Tyr Leu Phe Met Asn Ala Thr Gly
                245                 250                 255

Pro His Lys Tyr Glu Gly Lys Thr Arg Asp His Phe Asn Pro Lys Ser
            260                 265                 270
```

```
Ala Leu Phe Ala Lys Glu Asp Tyr Phe Asp Ile Val Ser Ser Asp Cys
            275                 280                 285

Gly Phe Leu Ala Leu Ala Gly Leu Val Tyr Ala Gly Tyr Thr Phe
290                 295                 300

Gly Pro Met Ala Val Leu Lys Tyr Tyr Trp Met Pro Tyr Met Trp Val
305                 310                 315                 320

Asn His Trp Leu Val Leu Ile Thr Tyr Leu Gln His Thr Asp Val Asn
                325                 330                 335

Val Pro His Tyr Arg Gly Glu Glu Trp Asn Trp Leu Arg Gly Ala Gly
                340                 345                 350

Cys Thr Ile Asp Arg Ser Phe Thr Pro Val Leu Asn His Leu Phe His
                355                 360                 365

His Ile Thr Asp Thr His Val Cys His His Leu Phe His Thr Met Pro
370                 375                 380

Phe Tyr His Ala Glu Glu Ala Thr Lys His Ile Lys Lys Val Leu Gly
385                 390                 395                 400

Asp Tyr Tyr Met His Asp Asp Thr Phe Phe Pro Leu Ala Ala Tyr Arg
                405                 410                 415

Ala Met Ser Glu Cys Arg Phe Val Asp Asn Glu Gly Pro Val Val Phe
                420                 425                 430

Tyr Lys Ala His Asp
            435

<210> SEQ ID NO 113
<211> LENGTH: 393
<212> TYPE: PRT
<213> ORGANISM: Saprolegnia diclina

<400> SEQUENCE: 113

Met Cys Lys Gly Gln Ala Pro Ser Lys Ala Asp Val Phe His Ala Ala
1               5                   10                  15

Gly Tyr Arg Pro Val Ala Gly Thr Pro Glu Pro Leu Pro Leu Glu Pro
                20                  25                  30

Pro Thr Ile Thr Leu Lys Asp Leu Arg Ala Ala Ile Pro Ala His Cys
            35                  40                  45

Phe Glu Arg Ser Ala Ala Thr Ser Phe Tyr His Leu Ala Lys Asn Leu
50                  55                  60

Ala Ile Cys Ala Gly Val Phe Ala Val Gly Leu Lys Leu Ala Ala Ala
65                  70                  75                  80

Asp Leu Pro Leu Ala Ala Lys Leu Val Ala Trp Pro Ile Tyr Trp Phe
                85                  90                  95

Val Gln Gly Thr Tyr Phe Thr Gly Ile Trp Val Ile Ala His Glu Cys
                100                 105                 110

Gly His Gln Ala Phe Ser Ala Ser Glu Ile Leu Asn Asp Thr Val Gly
            115                 120                 125

Ile Ile Leu His Ser Leu Leu Phe Val Pro Tyr His Ser Trp Lys Ile
130                 135                 140

Thr His Arg Arg His His Ser Asn Thr Gly Ser Cys Glu Asn Asp Glu
145                 150                 155                 160

Val Phe Thr Pro Thr Pro Arg Ser Val Val Glu Ala Lys His Asp His
                165                 170                 175

Ser Leu Leu Glu Glu Ser Pro Leu Tyr Asn Leu Tyr Gly Ile Val Met
            180                 185                 190

Met Leu Leu Val Gly Trp Met Pro Gly Tyr Leu Phe Phe Asn Ala Thr
```

```
                195                 200                 205
Gly Pro Thr Lys Tyr Ala Gly Leu Ala Lys Ser His Phe Asn Pro Tyr
210                 215                 220

Ala Ala Phe Phe Leu Pro Lys Glu Arg Leu Ser Ile Trp Trp Ser Asp
225                 230                 235                 240

Leu Cys Phe Leu Ala Ala Leu Tyr Gly Phe Gly Tyr Gly Val Ser Val
                245                 250                 255

Phe Gly Leu Leu Asp Val Ala Arg His Tyr Ile Val Pro Tyr Leu Ile
                260                 265                 270

Cys Asn Ala Tyr Leu Val Leu Ile Thr Tyr Leu Gln His Thr Asp Thr
                275                 280                 285

Tyr Val Pro His Phe Arg Gly Asp Glu Trp Asn Trp Leu Arg Gly Ala
                290                 295                 300

Leu Cys Thr Val Asp Arg Ser Phe Gly Ala Trp Ile Asp Ser Ala Ile
305                 310                 315                 320

His His Ile Ala Asp Thr His Val Thr His His Ile Phe Ser Lys Thr
                325                 330                 335

Pro Phe Tyr His Ala Ile Glu Ala Thr Asp Ala Ile Thr Pro Leu Leu
                340                 345                 350

Gly Asp Lys Tyr Leu Ile Asp Pro Thr Pro Ile Pro Leu Ala Leu Trp
                355                 360                 365

Arg Ser Phe Thr His Cys Lys Tyr Val Glu Asp Gly Asn Val Val
370                 375                 380

Phe Tyr Lys Arg Lys Leu Glu Glu Lys
385                 390

<210> SEQ ID NO 114
<211> LENGTH: 396
<212> TYPE: PRT
<213> ORGANISM: Mucor circinelloides

<400> SEQUENCE: 114

Met Ala Thr Lys Arg Asn Val Thr Ser Asn Ala Pro Ala Ala Glu Asp
1               5                   10                  15

Ile Ser Ile Ser Asn Lys Ala Val Ile Asp Glu Ala Ile Glu Arg Asn
                20                  25                  30

Trp Glu Ile Pro Asn Phe Thr Ile Lys Glu Ile Arg Asp Ala Ile Pro
            35                  40                  45

Ala His Cys Phe Arg Arg Asp Thr Phe Arg Ser Phe Thr His Val Leu
        50                  55                  60

His Asp Ile Ile Ile Met Ser Ile Leu Ala Ile Gly Ala Ser Tyr Ile
65                  70                  75                  80

Asp Ser Ile Pro Asn Thr Tyr Ala Arg Ile Ala Leu Trp Pro Leu Tyr
                85                  90                  95

Trp Ile Ala Gln Gly Ile Val Gly Thr Gly Val Trp Val Ile Gly His
            100                 105                 110

Glu Cys Gly His Gln Ala Phe Ser Pro Ser Lys Thr Ile Asn Asn Ser
        115                 120                 125

Val Gly Tyr Val Leu His Thr Ala Leu Leu Val Pro Tyr His Ser Trp
    130                 135                 140

Arg Phe Ser His Ser Lys His His Lys Ala Thr Gly His Met Ser Lys
145                 150                 155                 160

Asp Gln Val Phe Val Pro Ser Thr Arg Lys Glu Tyr Gly Leu Pro Pro
                165                 170                 175
```

```
Arg Glu Gln Asp Pro Glu Val Asp Gly Pro His Asp Ala Leu Asp Glu
                180                 185                 190
Ala Pro Ile Val Val Leu Tyr Arg Met Phe Leu Gln Phe Thr Phe Gly
            195                 200                 205
Trp Pro Leu Tyr Leu Phe Thr Asn Val Ser Gly Gln Asp Tyr Pro Gly
    210                 215                 220
Trp Ala Ser His Phe Asn Pro Lys Cys Ala Ile Tyr Asp Glu Asn Gln
225                 230                 235                 240
Phe Trp Asp Val Met Ser Ser Thr Ala Val Leu Gly Met Ile Gly
                245                 250                 255
Phe Leu Ala Tyr Cys Gly Gln Val Phe Gly Ser Leu Ala Val Ile Lys
            260                 265                 270
Tyr Tyr Val Ile Pro Tyr Leu Asn Val Asn Phe Trp Leu Val Leu Ile
    275                 280                 285
Thr Tyr Leu Gln His Thr Asp Pro Lys Leu Pro His Tyr Arg Glu Asn
    290                 295                 300
Val Trp Asn Phe Gln Arg Gly Ala Ala Leu Thr Val Asp Arg Ser Tyr
305                 310                 315                 320
Gly Phe Leu Leu Asp Tyr Phe His His Ile Ser Asp Thr His Val
                325                 330                 335
Ala His His Phe Phe Ser Thr Met Pro His Tyr His Ala Glu Glu Ala
            340                 345                 350
Thr Val His Ile Lys Lys Ala Leu Gly Lys His Tyr His Cys Asp Asn
                355                 360                 365
Thr Pro Val Pro Ile Ala Leu Trp Lys Val Trp Lys Ser Cys Arg Phe
    370                 375                 380
Val Glu Asp Glu Gly Asp Val Val Phe Phe Lys Asn
385                 390                 395

<210> SEQ ID NO 115
<211> LENGTH: 389
<212> TYPE: PRT
<213> ORGANISM: Rhizopus oryzae

<400> SEQUENCE: 115

Met Ala Thr Lys Arg Asn Ile Ser Ser Asn Glu Pro Glu Asn Lys Pro
1               5                   10                  15
Val Ile Asp Glu Ala Val Ala Arg Asn Trp Glu Ile Pro Asp Phe Thr
            20                  25                  30
Ile Lys Glu Ile Arg Asp Ala Ile Pro Ser His Cys Phe Arg Arg Asp
        35                  40                  45
Thr Phe Arg Ser Phe Thr Tyr Val Ile His Asp Phe Ala Ile Ile Ala
    50                  55                  60
Val Leu Gly Tyr Leu Ala Thr Tyr Ile Asp Gln Val His Ser Ala Ala
65                  70                  75                  80
Leu Arg Leu Leu Leu Trp Ser Leu Tyr Trp Thr Ala Gln Gly Ile Val
                85                  90                  95
Gly Thr Gly Val Trp Val Val Gly His Glu Cys Gly His Gln Ala Phe
            100                 105                 110
Ser Pro Ser Lys Ala Val Asn Asn Ser Val Gly Phe Val Leu His Thr
        115                 120                 125
Leu Leu Leu Val Pro Tyr His Ser Trp Arg Phe Ser His Ser Lys His
    130                 135                 140
His Lys Ala Thr Gly His Met Ser Lys Asp Gln Val Phe Leu Pro Lys
145                 150                 155                 160
```

```
Thr Arg Glu Lys Val Gly Leu Pro Pro Arg Asp Lys Asp Pro Gln Ala
                165                 170                 175

Asp Gly Pro His Asp Val Leu Asp Glu Thr Pro Ile Val Val Leu Tyr
            180                 185                 190

Arg Met Phe Leu Met Phe Leu Phe Gly Trp Pro Leu Tyr Leu Phe Thr
        195                 200                 205

Asn Val Thr Gly Gln Asp Tyr Pro Gly Trp Ala Ser His Phe Asn Pro
    210                 215                 220

Ser Cys Asp Ile Tyr Glu Glu Gly Gln Tyr Trp Asp Val Val Ser Ser
225                 230                 235                 240

Ser Val Gly Val Val Gly Met Val Gly Leu Leu Gly Tyr Cys Gly Gln
                245                 250                 255

Ile Phe Gly Ser Leu Asn Met Ile Lys Tyr Tyr Val Ile Pro Tyr Leu
                260                 265                 270

Cys Val Asn Phe Trp Leu Val Leu Ile Thr Tyr Leu Gln His Thr Asp
                275                 280                 285

Pro Lys Leu Pro His Tyr Arg Glu Asn Val Trp Asn Phe Gln Arg Gly
            290                 295                 300

Ala Ala Leu Thr Val Asp Arg Ser Tyr Gly Ala Leu Ile Asn Tyr Phe
305                 310                 315                 320

His His His Ile Ser Asp Thr His Val Ala His His Phe Phe Ser Thr
                325                 330                 335

Met Pro His Tyr His Ala Glu Glu Ala Thr Val His Ile Lys Lys Ala
            340                 345                 350

Leu Gly Lys His Tyr His Cys Asp Asn Thr Pro Ile Pro Ile Ala Leu
        355                 360                 365

Trp Lys Val Trp Lys Ser Cys Arg Phe Val Glu Ser Glu Gly Asp Val
    370                 375                 380

Val Phe Tyr Lys Asn
385

<210> SEQ ID NO 116
<211> LENGTH: 400
<212> TYPE: PRT
<213> ORGANISM: Mortierella alpina

<400> SEQUENCE: 116

Met Ala Pro Pro Asn Thr Ile Asp Ala Gly Leu Thr Gln Arg His Ile
1               5                   10                  15

Ser Thr Ser Ala Ala Pro Thr Ser Ala Lys Pro Ala Phe Glu Arg Asn
                20                  25                  30

Tyr Gln Leu Pro Glu Phe Thr Ile Lys Glu Ile Arg Glu Cys Ile Pro
            35                  40                  45

Ala His Cys Phe Glu Arg Ser Gly Leu Arg Gly Leu Cys His Val Ala
        50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Ala Tyr
                85                  90                  95

Trp Ile Met Gln Gly Ile Val Cys Thr Gly Ile Trp Val Leu Ala His
                100                 105                 110

Glu Cys Gly His Gln Ser Phe Ser Thr Ser Lys Thr Leu Asn Asn Thr
            115                 120                 125

Val Gly Trp Ile Leu His Ser Met Leu Leu Val Pro Tyr His Ser Trp
```

130                 135                 140
Arg Ile Ser His Ser Lys His His Lys Ala Thr Gly His Met Thr Lys
145                 150                 155                 160

Asp Gln Val Phe Val Pro Lys Thr Arg Ser Gln Val Gly Leu Pro Pro
                165                 170                 175

Lys Glu Asn Val Ala Val Ala Val Gln Glu Asp Met Ser Val His
            180                 185                 190

Leu Asp Glu Glu Ala Pro Ile Val Thr Leu Phe Trp Met Val Ile Gln
        195                 200                 205

Phe Leu Phe Gly Trp Pro Ala Tyr Leu Ile Met Asn Ala Ser Gly Gln
    210                 215                 220

Asp Tyr Gly Arg Trp Thr Ser His Phe His Thr Tyr Ser Pro Ile Phe
225                 230                 235                 240

Glu Pro Arg Asn Phe Phe Asp Ile Ile Ile Ser Asp Leu Gly Val Leu
                245                 250                 255

Ala Ala Leu Gly Thr Leu Ile Tyr Ala Ser Met Gln Leu Ser Leu Leu
            260                 265                 270

Thr Val Thr Lys Tyr Tyr Ile Val Pro Tyr Leu Phe Val Asn Phe Trp
        275                 280                 285

Leu Val Leu Ile Thr Phe Leu Gln His Thr Asp Pro Lys Leu Pro His
    290                 295                 300

Tyr Arg Glu Gly Ala Trp Asn Phe Gln Arg Gly Ala Leu Cys Thr Val
305                 310                 315                 320

Asp Arg Ser Phe Gly Lys Phe Leu Asp His Met Phe His Gly Ile Val
                325                 330                 335

His Thr His Val Ala His His Leu Phe Ser Gln Met Pro Phe Tyr His
            340                 345                 350

Ala Glu Glu Ala Thr His His Leu Lys Lys Leu Leu Gly Glu Tyr Tyr
        355                 360                 365

Val Tyr Asp Pro Ser Pro Ile Val Val Ala Val Trp Arg Ser Phe Arg
    370                 375                 380

Glu Cys Arg Phe Val Glu Asp His Gly Asp Val Val Phe Phe Lys Lys
385                 390                 395                 400

<210> SEQ ID NO 117
<211> LENGTH: 408
<212> TYPE: PRT
<213> ORGANISM: Trypanosoma brucei

<400> SEQUENCE: 117

Met Leu Pro Lys Gln Gln Met Gly Gly Ser Val Cys Asn Ala Ser Ile
1               5                   10                  15

Glu Thr Val Asn Thr Glu Ala Thr Asp Pro Ser Glu Ala Lys Lys Ile
            20                  25                  30

Val Leu Asn Ala Gly Arg Ser Glu Lys Val Asn Val Tyr Val Pro Pro
        35                  40                  45

Ser Thr Leu Met Val Arg Asp Ile Gln Glu Gln Ile Pro Ala Glu Tyr
    50                  55                  60

Phe Gln Arg Ser Met Trp Arg Ser Phe Ser Tyr Leu Ser Arg Asp Met
65                  70                  75                  80

Phe Gln Leu Phe Leu Thr Phe Val Ile Met Tyr Asn Phe Val Leu Pro
                85                  90                  95

Met Leu Asp Ser Ser Leu Leu Asn Ala Val Pro Pro Val Ala Trp Leu
            100                 105                 110

Ser Arg Ala Ala Ala Trp Met Ile Tyr Trp Phe Val Gln Gly Leu Asn
            115                 120                 125

Gly Thr Ala Leu Trp Val Leu Ala His Glu Cys Gly His Gln Ala Phe
        130                 135                 140

Cys Asn Ser Arg Arg Val Asn Asn Ala Val Gly Met Ile Leu His Ser
145                 150                 155                 160

Ala Leu Leu Val Pro Tyr His Ser Trp Arg Leu Thr His Gly Thr His
                165                 170                 175

His Lys His Thr Asn His Leu Thr Lys Asp Leu Val Phe Val Pro Val
            180                 185                 190

Gln Arg Ser Ala Val Gly Glu Ala Val Glu Glu Ala Pro Ile Val Met
        195                 200                 205

Leu Trp Asn Met Ala Leu Met Phe Leu Phe Gly Trp Pro Met His Leu
210                 215                 220

Leu Val Asn Val Gly Gly Gln Lys Phe Asp Arg Phe Thr Ser His Phe
225                 230                 235                 240

Asp Pro Asn Ala Pro Phe Phe Arg Arg Ala Asp Tyr Asn Asn Val Met
                245                 250                 255

Val Ser Asn Met Gly Val Leu Leu Thr Leu Ser Ile Leu Gly Ala Cys
            260                 265                 270

Ser Trp Ser Phe Gly Phe Ala Val Val Arg Trp Tyr Leu Ile Pro
        275                 280                 285

Tyr Leu Trp Val Asn Phe Trp Leu Val Tyr Ile Thr Tyr Met Gln His
        290                 295                 300

Ser Asp Val Arg Leu Pro His Tyr Thr His Asp His Trp Thr Tyr Val
305                 310                 315                 320

Arg Gly Ala Val Ala Ala Val Asp Arg Asp Phe Gly Pro Leu Leu Asn
                325                 330                 335

Ser Trp Leu His His Ile Asn Asp Ser His Val Val His His Leu Phe
            340                 345                 350

Ser Gln Met Pro His Tyr Asn Ala Ile Glu Val Thr Arg Lys His Ile
        355                 360                 365

Arg Asp Ile Leu Gly Asp Leu Tyr Val Thr Asp Ala Lys Pro Leu Leu
370                 375                 380

Lys Ser Leu Val His Thr Trp Arg Glu Cys Arg Tyr Val Val Pro Ser
385                 390                 395                 400

Glu Gly Ile Cys Ile Thr Arg Ser
                405

<210> SEQ ID NO 118
<211> LENGTH: 439
<212> TYPE: PRT
<213> ORGANISM: Thraustochytrium aureum

<400> SEQUENCE: 118

Met Gly Arg Gly Gly Glu Gly Gln Val Asn Ser Val Gln Val Ala Gln
1               5                   10                  15

Gly Gly Ala Gly Thr Arg Lys Thr Ile Leu Ile Glu Gly Glu Val Tyr
            20                  25                  30

Asp Val Thr Asn Phe Arg His Pro Gly Gly Ser Ile Ile Lys Phe Leu
        35                  40                  45

Thr Thr Asp Gly Thr Glu Ala Val Asp Ala Thr Asn Ala Phe Arg Glu
    50                  55                  60

Phe His Cys Arg Ser Gly Lys Ala Glu Lys Tyr Leu Lys Ser Leu Pro
65                  70                  75                  80

```
Lys Leu Gly Ala Pro Ser Lys Met Lys Phe Asp Ala Lys Glu Gln Ala
                85                  90                  95

Arg Arg Asp Ala Ile Thr Arg Asp Tyr Val Lys Leu Arg Glu Glu Met
            100                 105                 110

Val Ala Glu Gly Leu Phe Lys Pro Ala Pro Leu His Ile Val Tyr Arg
        115                 120                 125

Phe Ala Glu Ile Ala Ala Leu Phe Ala Ala Ser Phe Tyr Leu Phe Ser
130                 135                 140

Met Arg Gly Asn Val Phe Ala Thr Leu Ala Ala Ile Ala Val Gly Gly
145                 150                 155                 160

Ile Ala Gln Gly Arg Cys Gly Trp Leu Met His Glu Cys Gly His Phe
                165                 170                 175

Ser Met Thr Gly Tyr Ile Pro Leu Asp Val Arg Leu Gln Glu Leu Val
            180                 185                 190

Tyr Gly Val Gly Cys Ser Met Ser Ala Ser Trp Trp Arg Val Gln His
        195                 200                 205

Ser Lys His His Ala Thr Pro Gln Lys Leu Lys His Asp Val Asp Leu
210                 215                 220

Asp Thr Leu Pro Leu Val Ala Phe Asn Glu Lys Ile Ala Ala Lys Val
225                 230                 235                 240

Arg Pro Gly Ser Phe Gln Ala Lys Trp Leu Ser Ala Gln Ala Tyr Ile
                245                 250                 255

Phe Ala Pro Val Ser Cys Phe Leu Val Gly Leu Phe Trp Thr Leu Phe
            260                 265                 270

Leu His Pro Arg His Met Leu Arg Thr Ser His Phe Ala Glu Met Ala
        275                 280                 285

Ala Val Ala Val Arg Val Val Gly Trp Ala Ala Leu Met His Ser Phe
290                 295                 300

Gly Tyr Ser Gly Ser Asp Ser Phe Gly Leu Tyr Met Ala Thr Phe Gly
305                 310                 315                 320

Phe Gly Cys Thr Tyr Ile Phe Thr Asn Phe Ala Val Ser His Thr His
                325                 330                 335

Leu Asp Val Thr Glu Pro Asp Glu Phe Leu His Trp Val Glu Tyr Ala
            340                 345                 350

Ala Leu His Thr Thr Asn Val Ser Asn Asp Ser Trp Phe Ile Thr Trp
        355                 360                 365

Trp Met Ser Tyr Leu Asn Phe Gln Ile Glu His His Leu Phe Pro Ser
370                 375                 380

Leu Pro Gln Leu Asn Ala Pro Arg Val Ala Pro Arg Val Arg Ala Leu
385                 390                 395                 400

Phe Glu Lys His Gly Met Ala Tyr Asp Glu Arg Pro Tyr Pro Thr Ala
                405                 410                 415

Leu Gly Asp Thr Phe Ala Asn Leu His Ala Val Gly Gln Asn Ala Gly
            420                 425                 430

Gln Ala Ala Ala Lys Ala Ala
        435

<210> SEQ ID NO 119
<211> LENGTH: 439
<212> TYPE: PRT
<213> ORGANISM: Thraustochytrium sp. ATCC21685

<400> SEQUENCE: 119

Met Gly Lys Gly Ser Glu Gly Arg Ser Ala Ala Arg Glu Met Thr Ala
```

-continued

```
1               5                   10                  15
Glu Ala Asn Gly Asp Lys Arg Lys Thr Ile Leu Ile Glu Gly Val Leu
                20                  25                  30
Tyr Asp Ala Thr Asn Phe Lys His Pro Gly Gly Ser Ile Ile Asn Phe
                35                  40                  45
Leu Thr Glu Gly Glu Ala Gly Val Asp Ala Thr Gln Ala Tyr Arg Glu
                50                  55                  60
Phe His Gln Arg Ser Gly Lys Ala Asp Lys Tyr Leu Lys Ser Leu Pro
65                  70                  75                  80
Lys Leu Asp Ala Ser Lys Val Glu Ser Arg Phe Ser Ala Lys Glu Gln
                85                  90                  95
Ala Arg Arg Asp Ala Met Thr Arg Asp Tyr Ala Ala Phe Arg Glu Glu
                100                 105                 110
Leu Val Ala Glu Gly Tyr Phe Asp Pro Ser Ile Pro His Met Ile Tyr
                115                 120                 125
Arg Val Val Glu Ile Val Ala Leu Phe Ala Leu Ser Phe Trp Leu Met
                130                 135                 140
Ser Lys Ala Ser Pro Thr Ser Leu Val Leu Gly Val Val Met Asn Gly
145                 150                 155                 160
Ile Ala Gln Gly Arg Cys Gly Trp Val Met His Glu Met Gly His Gly
                165                 170                 175
Ser Phe Thr Gly Val Ile Trp Leu Asp Asp Arg Met Cys Glu Phe Phe
                180                 185                 190
Tyr Gly Val Gly Cys Gly Met Ser Gly His Tyr Trp Lys Asn Gln His
                195                 200                 205
Ser Lys His His Ala Ala Pro Asn Arg Leu Glu His Asp Val Asp Leu
210                 215                 220
Asn Thr Leu Pro Leu Val Ala Phe Asn Glu Arg Val Val Arg Lys Val
225                 230                 235                 240
Lys Pro Gly Ser Leu Leu Ala Leu Trp Leu Arg Val Gln Ala Tyr Leu
                245                 250                 255
Phe Ala Pro Val Ser Cys Leu Leu Ile Gly Leu Gly Trp Thr Leu Tyr
                260                 265                 270
Leu His Pro Arg Tyr Met Leu Arg Thr Lys Arg His Met Glu Phe Val
                275                 280                 285
Trp Ile Phe Ala Arg Tyr Ile Gly Trp Phe Ser Leu Met Gly Ala Leu
                290                 295                 300
Gly Tyr Ser Pro Gly Thr Ser Val Gly Met Tyr Leu Cys Ser Phe Gly
305                 310                 315                 320
Leu Gly Cys Ile Tyr Ile Phe Leu Gln Phe Ala Val Ser His Thr His
                325                 330                 335
Leu Pro Val Thr Asn Pro Glu Asp Gln Leu His Trp Leu Glu Tyr Ala
                340                 345                 350
Ala Asp His Thr Val Asn Ile Ser Thr Lys Ser Trp Leu Val Thr Trp
                355                 360                 365
Trp Met Ser Asn Leu Asn Phe Gln Ile Glu His His Leu Phe Pro Thr
                370                 375                 380
Ala Pro Gln Phe Arg Phe Lys Glu Ile Ser Pro Arg Val Glu Ala Leu
385                 390                 395                 400
Phe Lys Arg His Asn Leu Pro Tyr Tyr Asp Leu Pro Tyr Thr Ser Ala
                405                 410                 415
Val Ser Thr Thr Phe Ala Asn Leu Tyr Ser Val Gly His Ser Val Gly
                420                 425                 430
```

```
Ala Asp Thr Lys Lys Gln Asp
        435

<210> SEQ ID NO 120
<211> LENGTH: 417
<212> TYPE: PRT
<213> ORGANISM: Leishmania major strain Friedlin

<400> SEQUENCE: 120

Met Ala Leu Asp Asn Val Arg Pro His Gln Pro Asn Glu Val Leu Ile
1               5                   10                  15

Asp Gly Val Leu Tyr Asp Cys Thr Asp Phe Arg His Pro Gly Gly Ser
            20                  25                  30

Ile Leu Lys Tyr Tyr Leu Gly Ser Gly Asp Ala Thr Glu Thr Tyr Gln
        35                  40                  45

Gln Phe His Leu Lys Leu Pro Arg Ala Asp Lys Tyr Leu Lys Arg Leu
    50                  55                  60

Pro Asn Arg Pro Ala Pro Pro Gln His Ser Val Asn Val Asp Glu Gln
65                  70                  75                  80

Lys Arg Leu Glu Lys Leu Ser Arg Asp Phe Lys Ala Leu Gln Asp Ala
                85                  90                  95

Cys Val Glu Glu Gly Leu Phe Asn Ala Ser Trp Pro His Ile Val Tyr
            100                 105                 110

Arg Phe Ser Glu Leu Ile Leu Met His Ala Ile Gly Leu Tyr Met Leu
        115                 120                 125

Phe Arg Leu Pro Ile Leu Trp Pro Val Ala Leu Val Ile Leu Gly Val
    130                 135                 140

Ala Glu Gly Arg Cys Gly Trp Trp Met His Glu Ala Gly His Tyr Ser
145                 150                 155                 160

Val Thr Gly Ile Pro Trp Leu Asp Ile Lys Ile Gln Glu Val Leu Tyr
                165                 170                 175

Gly Leu Gly Asp Gly Met Ser Ala Ser Trp Trp Arg Ser Gln His Asn
            180                 185                 190

Lys His His Ala Thr Pro Gln Lys His Arg His Asp Val Asp Leu Glu
        195                 200                 205

Thr Leu Pro Leu Val Ala Phe Asn Lys Ile Ile Ala Arg Arg Gly Lys
    210                 215                 220

Arg Asn Ala Ser Ile Arg Arg Trp Ile Ser Leu Gln Met Phe Leu Phe
225                 230                 235                 240

Gly Pro Val Thr Cys Ser Leu Val Ala Leu Tyr Trp Gln Leu Phe Leu
                245                 250                 255

His Val Arg His Ala Met Arg Thr Gln Arg Tyr Thr Glu Gly Ser Ala
            260                 265                 270

Ile Leu Cys Arg Trp Ile Val Val Gly Val Ile Cys His Gln Leu Gln
        275                 280                 285

Val Ser Phe Trp Gln Gly Leu Gly Gly Val Leu Phe Ser Gln Ala Phe
    290                 295                 300

Ser Ala Ala Tyr Ile Phe Ile Asn Phe Ala Leu Asn His Ser His Leu
305                 310                 315                 320

Pro Met Leu Pro Glu Asp Glu His Ala His Phe Val Glu Tyr Ala Ala
                325                 330                 335

Ile Tyr Thr Met Asn Val Thr Pro Ser Trp Phe Val Thr Trp Phe Met
            340                 345                 350

Gly Tyr Leu Asn Tyr Gln Val Glu His His Leu Phe Pro Thr Met Pro
```

-continued

```
              355                 360                 365
Gln Phe Arg Phe Val Gln Leu Ala Pro Arg Val Arg Lys Leu Phe Glu
            370                 375                 380
Glu Asn Gly Leu Lys Tyr Asp Ser Arg Pro Tyr Met Glu Ser Leu Gln
385                 390                 395                 400
Lys Thr Phe Lys Asn Leu Gly Asp Val Ala Glu Phe Ile Val Ala Gly
                405                 410                 415
Asn

<210> SEQ ID NO 121
<211> LENGTH: 447
<212> TYPE: PRT
<213> ORGANISM: Mus musculus

<400> SEQUENCE: 121

Met Ala Pro Asp Pro Val Pro Thr Pro Gly Pro Ala Ser Ala Gln Leu
1               5                   10                  15
Arg Gln Thr Arg Tyr Phe Thr Trp Glu Glu Val Ala Gln Arg Ser Gly
            20                  25                  30
Arg Glu Lys Glu Arg Trp Leu Val Ile Asp Arg Lys Val Tyr Asn Ile
        35                  40                  45
Ser Asp Phe Ser Arg Arg His Pro Gly Gly Ser Arg Val Ile Ser His
    50                  55                  60
Tyr Ala Gly Gln Asp Ala Thr Asp Pro Phe Val Ala Phe His Ile Asn
65                  70                  75                  80
Lys Gly Leu Val Arg Lys Tyr Met Asn Ser Leu Leu Ile Gly Glu Leu
                85                  90                  95
Ala Pro Glu Gln Pro Ser Phe Glu Pro Thr Lys Asn Lys Ala Leu Thr
            100                 105                 110
Asp Glu Phe Arg Glu Leu Arg Ala Thr Val Glu Arg Met Gly Leu Met
        115                 120                 125
Lys Ala Asn His Leu Phe Phe Leu Val Tyr Leu His Ile Leu Leu
    130                 135                 140
Leu Asp Val Ala Ala Trp Leu Thr Leu Trp Ile Phe Gly Thr Ser Leu
145                 150                 155                 160
Val Pro Phe Ile Leu Cys Ala Val Leu Leu Ser Thr Val Gln Ala Gln
                165                 170                 175
Ala Gly Trp Leu Gln His Asp Phe Gly His Leu Ser Val Phe Gly Thr
            180                 185                 190
Ser Thr Trp Asn His Leu Leu His His Phe Val Ile Gly His Leu Lys
        195                 200                 205
Gly Ala Pro Ala Ser Trp Trp Asn His Met His Phe Gln His His Ala
    210                 215                 220
Lys Pro Asn Cys Phe Arg Lys Asp Pro Asp Ile Asn Met His Pro Leu
225                 230                 235                 240
Phe Phe Ala Leu Gly Lys Val Leu Pro Val Glu Leu Gly Arg Glu Lys
                245                 250                 255
Lys Lys His Met Pro Tyr Asn His Gln His Lys Tyr Phe Phe Leu Ile
            260                 265                 270
Gly Pro Pro Ala Leu Leu Pro Leu Tyr Phe Gln Trp Tyr Ile Phe Tyr
        275                 280                 285
Phe Val Val Gln Arg Lys Lys Trp Val Asp Leu Ala Trp Met Leu Ser
    290                 295                 300
Phe Tyr Ala Arg Ile Phe Phe Thr Tyr Met Pro Leu Leu Gly Leu Lys
```

```
                305                 310                 315                 320
Gly Phe Leu Gly Leu Phe Phe Ile Val Arg Phe Leu Glu Ser Asn Trp
                325                 330                 335

Phe Val Trp Val Thr Gln Met Asn His Ile Pro Met His Ile Asp His
                340                 345                 350

Asp Arg Asn Val Asp Trp Val Ser Thr Gln Leu Gln Ala Thr Cys Asn
                355                 360                 365

Val His Gln Ser Ala Phe Asn Asn Trp Phe Ser Gly His Leu Asn Phe
                370                 375                 380

Gln Ile Glu His His Leu Phe Pro Thr Met Pro Arg His Asn Tyr His
385                 390                 395                 400

Lys Val Ala Pro Leu Val Gln Ser Leu Cys Ala Lys Tyr Gly Ile Lys
                405                 410                 415

Tyr Glu Ser Lys Pro Leu Leu Thr Ala Phe Ala Asp Ile Val Tyr Ser
                420                 425                 430

Leu Lys Glu Ser Gly Gln Leu Trp Leu Asp Ala Tyr Leu His Gln
                435                 440                 445
```

<210> SEQ ID NO 122
<211> LENGTH: 447
<212> TYPE: PRT
<213> ORGANISM: Rattus norvegicus

<400> SEQUENCE: 122

```
Met Ala Pro Asp Pro Val Gln Thr Pro Asp Pro Ala Ser Ala Gln Leu
1               5                   10                  15

Arg Gln Met Arg Tyr Phe Thr Trp Glu Glu Val Ala Gln Arg Ser Gly
                20                  25                  30

Arg Glu Lys Glu Arg Trp Leu Val Ile Asp Arg Lys Val Tyr Asn Ile
                35                  40                  45

Ser Asp Phe Ser Arg Arg His Pro Gly Gly Ser Arg Val Ile Ser His
                50                  55                  60

Tyr Ala Gly Gln Asp Ala Thr Asp Arg Phe Val Ala Phe His Ile Asn
65              70                  75                  80

Lys Gly Leu Val Glu Lys Tyr Met Asn Ser Leu Leu Ile Gly Glu Leu
                85                  90                  95

Ala Pro Glu Gln Ser Ser Phe Glu Pro Thr Lys Asn Lys Ala Leu Thr
                100                 105                 110

Asp Glu Phe Arg Glu Leu Arg Ala Thr Val Glu Arg Met Gly Leu Met
                115                 120                 125

Lys Ala Asn His Leu Phe Phe Leu Phe Tyr Leu Leu His Ile Leu Leu
                130                 135                 140

Leu Asp Val Ala Ala Trp Leu Thr Leu Trp Ile Phe Gly Thr Ser Leu
145                 150                 155                 160

Val Pro Phe Thr Leu Cys Ala Val Leu Leu Ser Thr Val Gln Ala Gln
                165                 170                 175

Ala Gly Trp Leu Gln His Asp Phe Gly His Leu Ser Val Phe Ser Thr
                180                 185                 190

Ser Thr Trp Asn His Leu Val His His Phe Val Ile Gly His Leu Lys
                195                 200                 205

Gly Ala Pro Ala Ser Trp Trp Asn His Met His Phe Gln His His Ala
                210                 215                 220

Lys Pro Asn Cys Phe Arg Lys Asp Pro Asp Ile Asn Met His Pro Leu
225                 230                 235                 240
```

```
Phe Phe Ala Leu Gly Lys Val Leu Ser Val Glu Leu Gly Lys Glu Lys
                245                 250                 255

Lys Lys His Met Pro Tyr Asn His Gln His Lys Tyr Phe Phe Leu Ile
            260                 265                 270

Gly Pro Pro Ala Leu Leu Pro Leu Tyr Phe Gln Trp Tyr Ile Phe Tyr
        275                 280                 285

Phe Val Val Gln Arg Lys Lys Trp Val Asp Leu Ala Trp Met Leu Ser
290                 295                 300

Phe Tyr Val Arg Val Phe Phe Thr Tyr Met Pro Leu Leu Gly Leu Lys
305                 310                 315                 320

Gly Leu Leu Cys Leu Phe Phe Ile Val Arg Phe Leu Glu Ser Asn Trp
                325                 330                 335

Phe Val Trp Val Thr Gln Met Asn His Ile Pro Met His Ile Asp His
            340                 345                 350

Asp Arg Asn Val Asp Trp Val Ser Thr Gln Leu Gln Ala Thr Cys Asn
        355                 360                 365

Val His Gln Ser Ala Phe Asn Asn Trp Phe Ser Gly His Leu Asn Phe
370                 375                 380

Gln Ile Glu His His Leu Leu Pro Thr Met Pro Arg His Asn Tyr His
385                 390                 395                 400

Lys Val Ala Pro Leu Val Gln Ser Leu Cys Ala Lys Tyr Gly Ile Lys
                405                 410                 415

Tyr Glu Ser Lys Pro Leu Leu Thr Ala Phe Ala Asp Ile Val Tyr Ser
            420                 425                 430

Leu Lys Glu Ser Gly Gln Leu Trp Leu Asp Ala Tyr Leu His Gln
        435                 440                 445

<210> SEQ ID NO 123
<211> LENGTH: 444
<212> TYPE: PRT
<213> ORGANISM: Homo sapiens

<400> SEQUENCE: 123

Met Ala Pro Asp Pro Leu Ala Ala Glu Thr Ala Ala Gln Gly Leu Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175
```

```
Leu Gln His Asp Phe Gly His Leu Ser Val Phe Ser Thr Ser Lys Trp
                180                 185                 190

Asn His Leu Leu His His Phe Val Ile Gly His Leu Lys Gly Ala Pro
            195                 200                 205

Ala Ser Trp Trp Asn His Met His Phe Gln His Ala Lys Pro Asn
210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Asn Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
                275                 280                 285

Gln Arg Lys Lys Trp Val Asp Leu Ala Trp Met Ile Thr Phe Tyr Val
            290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Gln Ala Thr Cys Asn Val His Lys
                355                 360                 365

Ser Ala Phe Asn Asp Trp Phe Ser Gly His Leu Asn Phe Gln Ile Glu
            370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln
                435                 440

<210> SEQ ID NO 124
<211> LENGTH: 447
<212> TYPE: PRT
<213> ORGANISM: Caenorhabditis elegans

<400> SEQUENCE: 124

Met Val Leu Arg Glu Gln Glu His Glu Pro Phe Phe Ile Lys Ile Asp
1               5                   10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
```

```
                    100                 105                 110
Arg Met Arg Val Arg Ala Glu Gly Leu Met Asp Gly Ser Pro Leu Phe
            115                 120                 125

Tyr Ile Arg Lys Ile Leu Glu Thr Ile Phe Thr Ile Leu Phe Ala Phe
130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
            165                 170                 175

Gln Leu Phe Lys Asn Arg Tyr Tyr Asn Asp Leu Ala Ser Tyr Phe Val
            180                 185                 190

Gly Asn Phe Leu Gln Gly Phe Ser Ser Gly Gly Trp Lys Glu Gln His
            195                 200                 205

Asn Val His His Ala Ala Thr Asn Val Val Gly Arg Asp Gly Asp Leu
            210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
            245                 250                 255

Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
            275                 280                 285

Asn Thr Ala Ile Tyr Glu Gln Val Gly Leu Ser Leu His Trp Ala Trp
            290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
            325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
            355                 360                 365

Arg Pro Gly Arg Phe Ile Asp Trp Leu Trp Gly Gly Leu Asn Tyr Gln
            370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
            405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
            435                 440                 445

<210> SEQ ID NO 125
<211> LENGTH: 467
<212> TYPE: PRT
<213> ORGANISM: Dictyostelium discoideum AX4
```

<400> SEQUENCE: 125

```
Met Met Glu Thr Asn Asn Glu Asn Lys Glu Lys Leu Lys Leu Tyr Thr
1               5                   10                  15
Trp Asp Glu Val Ser Lys His Asn Gln Lys Asn Asp Leu Trp Ile Ile
            20                  25                  30
Val Asp Gly Lys Val Tyr Asn Ile Thr Lys Trp Val Pro Leu His Pro
        35                  40                  45
Gly Gly Glu Asp Ile Leu Leu Leu Ser Ala Gly Arg Asp Ala Thr Asn
    50                  55                  60
Leu Phe Glu Ser Tyr His Pro Met Thr Asp Lys His Tyr Ser Leu Ile
65                  70                  75                  80
Lys Gln Tyr Glu Ile Gly Tyr Ile Ser Ser Tyr Glu His Pro Lys Tyr
                85                  90                  95
Val Glu Lys Ser Glu Phe Tyr Ser Thr Leu Lys Gln Arg Val Arg Lys
            100                 105                 110
His Phe Gln Thr Ser Ser Gln Asp Pro Lys Val Ser Val Gly Val Phe
        115                 120                 125
Thr Arg Met Val Leu Ile Tyr Leu Phe Leu Phe Val Thr Tyr Tyr Leu
    130                 135                 140
Ser Gln Phe Ser Thr Asp Arg Phe Trp Leu Asn Cys Ile Phe Ala Val
145                 150                 155                 160
Leu Tyr Gly Val Ala Asn Ser Leu Phe Gly Leu His Thr Met His Asp
                165                 170                 175
Ala Cys His Thr Ala Ile Thr His Asn Pro Met Thr Trp Lys Ile Leu
            180                 185                 190
Gly Ala Thr Phe Asp Leu Phe Ala Gly Ala Ser Phe Tyr Ala Trp Cys
        195                 200                 205
His Gln His Val Ile Gly His His Leu Tyr Thr Asn Val Arg Asn Ala
    210                 215                 220
Asp Pro Asp Leu Gly Gln Gly Glu Ile Asp Phe Arg Val Val Thr Pro
225                 230                 235                 240
Tyr Gln Ala Arg Ser Trp Tyr His Lys Tyr Gln His Ile Tyr Ala Pro
                245                 250                 255
Ile Leu Tyr Gly Val Tyr Ala Leu Lys Tyr Arg Ile Gln Asp His Glu
            260                 265                 270
Ile Phe Thr Lys Lys Ser Asn Gly Ala Ile Arg Tyr Ser Pro Ile Ser
        275                 280                 285
Thr Ile Asp Thr Ala Ile Phe Ile Leu Gly Lys Leu Val Phe Ile Ile
    290                 295                 300
Ser Arg Phe Ile Leu Pro Leu Ile Tyr Asn His Ser Phe Ser His Leu
305                 310                 315                 320
Ile Cys Phe Phe Leu Ile Ser Glu Leu Val Leu Gly Trp Tyr Leu Ala
                325                 330                 335
Ile Ser Phe Gln Val Ser His Val Val Glu Asp Leu Gln Phe Met Ala
            340                 345                 350
Thr Pro Glu Ile Phe Asp Gly Ala Asp His Pro Leu Pro Thr Thr Phe
        355                 360                 365
Asn Gln Asp Trp Ala Ile Leu Gln Val Lys Thr Thr Gln Asp Tyr Ala
    370                 375                 380
Gln Asp Ser Val Leu Ser Thr Phe Phe Ser Gly Gly Leu Asn Leu Gln
385                 390                 395                 400
Val Ile His His Cys Phe Pro Thr Ile Ala Gln Asp Tyr Tyr Pro Gln
                405                 410                 415
```

```
Ile Val Pro Ile Leu Lys Glu Val Cys Lys Glu Tyr Asn Val Thr Tyr
            420                 425                 430

His Tyr Lys Pro Thr Phe Thr Glu Ala Ile Lys Ser His Ile Asn Tyr
        435                 440                 445

Leu Tyr Lys Met Gly Asn Asp Pro Asp Tyr Val Arg Lys Pro Val Asn
    450                 455                 460

Lys Asn Asp
465
```

METHOD FOR TRANSFORMING STRAMENOPILES

TECHNICAL FIELD

The present invention relates to a method for transforming stramenopiles. The invention also relates to stramenopiles having an enhanced unsaturated fatty acid content conferred by the introduction of a fatty acid desaturase gene, and to methods for producing unsaturated fatty acids from such unsaturated fatty acid content-enhanced stramenopiles.

BACKGROUND ART

Polyunsaturated fatty acids (PUFA) represent an important component of animal and human nutrition. ω3 polyunsaturated fatty acids (also called n-3 polyunsaturated fatty acids) such as eicosapentaenoic acid (EPA) and docosahexaenoic acid (DHA) have a wide range of roles in many aspects of health, including brain development in children, eye functions, syntheses of hormones and other signaling substances, and prevention of cardiovascular disease, cancer, and diabetes mellitus (Non-Patent Document 1). These fatty acids therefore represent an important component of human nutrition. Accordingly, there is a need for polyunsaturated fatty acid production.

Meanwhile, microorganisms of the class Labyrinthulomycetes are known to produce polyunsaturated fatty acids. Concerning microorganisms of the family *Thraustochytrium*, there are reports of, for example, a polyunsaturated fatty acid-containing phospholipid producing process using *Schizochytrium* microorganisms (Patent Document 1), and *Thraustochytrium* microorganisms having a docosahexaenoic acid producing ability (Patent Document 2). For enhancement of food and/or feed by the unsaturated fatty acids, there is a strong demand for a simple economical process for producing these unsaturated fatty acids, particularly in the eukaryotic system.

With regard to the class Labyrinthulomycetes, there have been reported foreign gene introducing methods for specific strains of the genus *Schizochytrium* (the genus *Auranthiochytrium* (Non-Patent Document 3) in the current classification scheme (Non-Patent Document 2)) (Patent Documents 3 and 4). Further, a method that causes a change in a fatty acid composition by means of transformation is known in which a polyketide synthase (PKS) gene is destroyed to change the resulting fatty acid composition (Non-Patent Document 4). However, there is no report directed to changing a fatty acid composition by manipulating the enzymes of the elongase/desaturase pathway.

CITATION LIST

Patent Documents

Patent Document 1: JP-A-2007-143479
Patent Document 2: JP-A-2005-102680
Patent Document 3: JP-A-2006-304685
Patent Document 4: JP-A-2006-304686
Patent Document 5: JP-A-2005-287380
Patent Document 6: PCT/DK96/00051

Non-Patent Documents

Non-Patent Document 1: Poulos, A Lipids 30:1-14, 1995; Horrocks, L A, and Yeo Y K, Pharmacol Res 40:211-225, 1999
Non-Patent Document 2: Yokoyama R., Honda D., Mycoscience 48:199-211, 2007
Non-Patent Document 3: Lecture Summary for the 60th Conference of The Society for Biotechnology, Japan, p 136, 2008
Non-Patent Document 4: Lippmeier J C et al., Lipids., July; 44(7):621-30. (2009), Epub 2009 Jun. 3.
Non-Patent Document 5: FEBS Lett. 553, 440-444 (2003).
Non-Patent Document 6: Nucleic Acids Res. (1994) 22, 4673-4680)
Non-Patent Document 7: Prasher, D. C. et al., Gene, 111 (2): 229-233 (1992)
Non-Patent Document 8: Chalfie M. et al., Science, 263:802-805, (1994)
Non-Patent Document 9: Southern, P. J., and Berg, P., J. Molec. Appl. Gen. 1, 327-339. (1982)
Non-Patent Document 10: Bio-Experiment Illustrated 2, Fundamentals of Gene Analysis p 63-68, Shujunsha
Non-Patent Document 11: Sanger, F., et al. Proc. Natl. Acad. Sci (1977) 74, 5463
Non-Patent Document 12: Bio-Experiment Illustrated 2, Fundamentals of Gene Analysis p 117-128, Shujunsha
Non-Patent Document 13: Adachi, J. et al. Comput. Sci. Monogr. (1996) 28

SUMMARY OF THE INVENTION

Problems that the Invention is to Solve

The present invention is directed to improving the ability of stramenopiles to produce a useful substance by way of transformation through introduction of a foreign gene. By modifying the ability to produce a useful substance through introduction of a foreign gene associated with the production of a useful substance in stramenopiles, the invention provides a modification method of a fatty acid composition produced by stramenopiles, a method for highly accumulating fatty acids in stramenopiles, an unsaturated fatty acid producing process, stramenopiles having an enhanced unsaturated fatty acid content, and production of unsaturated fatty acid from the unsaturated fatty acid content-enhanced stramenopiles. The present invention provides modification of a fatty acid composition produced by stramenopiles, and a method for highly accumulating fatty acids in stramenopiles, and thus enables more efficient production of polyunsaturated fatty acids.

Means for Solving the Problems

The present inventors conducted intensive studies under the foregoing circumstances of the conventional techniques, and succeeded in transforming stramenopiles with a foreign gene introduced to highly improve the ability to produce an unsaturated fatty acid. The present inventors also found a method for modifying the product fatty acid composition of stramenopiles through expression of a fatty acid desaturase gene introduced into the stramenopiles, and a method for highly accumulating unsaturated fatty acids in the transformed stramenopiles. The present invention was completed after further studies and development for practical applications.

The gist of the present invention includes the following technical matters (1) to (22).

(1) A method for transforming stramenopiles, comprising introducing a foreign gene into stramenopiles.
(2) The method according to (1), wherein the stramenopiles belong to the class Labyrinthulomycetes.

(3) The method according to (2), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium,* or *Sicyoidochytrium.*

(4) The method according to anyone of (1) to (3), wherein the microorganisms are any one of a *Schizochytrium* sp. M-8 strain (FERM P-19755), *Thraustochytrium aureum* ATCC 34304, *Thraustochytrium* sp. ATCC 26185, *Schizochytrium* sp. AL1Ac, *Schizochytrium aggregatum* ATCC 28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298).

(5) The method according to any one of (1) to (4), wherein the foreign gene is a gene associated with tolerance against an antibiotic, colorimetric protein, and/or fatty acid desaturase.

(6) The method according to any one of (1) to (5), wherein the gene associated with fatty acid desaturase is a Δ5 desaturase gene, a Δ12 desaturase gene, and/or an ω3 desaturase gene.

(7) The method according to any one of (1) to (6), wherein the foreign gene is introduced by electroporation or by using a gene gun technique.

(8) A method for modifying the fatty acid composition of stramenopiles,
comprising:
introducing a fatty acid desaturase gene; and
expressing the fatty acid desaturase.

(9) The method according to (8), wherein the fatty acid desaturase is a desaturase.

(10) The method according to (8) or (9), wherein the fatty acid desaturase is a Δ5 desaturase, a Δ12 desaturase, or an ω3 desaturase.

(11) The method according to any one of (8) to (10), wherein the stramenopiles belong to the class Labyrinthulomycetes.

(12) The method according to (11), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium,* or *Sicyoidochytrium.*

(13) The method according to (12), wherein the microorganisms are any one of a *Schizochytrium* sp. M-8 strain (FERM P-19755), *Thraustochytrium aureum* ATCC 34304, *Thraustochytrium* sp. ATCC 26185, *Schizochytrium* sp. AL1Ac, *Schizochytrium aggregatum* ATCC 28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298).

(14) A method for highly accumulating a fatty acid in a stramenopiles by using the method of any one of (8) to (13).

(15) The method according to (14), wherein the fatty acid is an unsaturated fatty acid.

(16) The method according to (15), wherein the unsaturated fatty acid is an unsaturated fatty acid of 18 to 22 carbon atoms.

(17) A fatty acid obtained by using the method of any one of (14) to (16).

(18) Stramenopiles transformed to modify a fatty acid composition.

(19) Stramenopiles transformed to highly accumulate fatty acids.

(20) The stramenopiles according to (18) or (19), wherein the stramenopiles belong to the class Labyrinthulomycetes.

(21) The stramenopiles according to (20), wherein the Labyrinthulomycetes are microorganisms belonging to the genus *Labyrinthula, Althornia, Aplanochytrium, Japonochytrium, Labyrinthuloides, Schizochytrium, Aurantiochytrium, Thraustochytrium, Ulkenia, Oblongichytrium, Botryochytrium, Parietichytrium,* or *Sicyoidochytrium.*

(22) The stramenopiles according to (21), wherein the microorganisms are any one of a *Schizochytrium* sp. M-8 strain (FERM P-19755), *Thraustochytrium aureum* ATCC 34304, *Thraustochytrium* sp. ATCC 26185, *Schizochytrium* sp. AL1Ac, *Schizochytrium aggregatum* ATCC 28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298).

Advantage of the Invention

The present invention enabled modification of the stramenopiles's ability to produce a useful substance (unsaturated fatty acid) through introduction of a foreign gene associated with the production of the useful substance, and thus realized a modification method of a fatty acid composition produced by stramenopiles, and a method for highly accumulating fatty acids in stramenopiles. The invention also realized an unsaturated fatty acid producing process, a stramenopiles having an enhanced unsaturated fatty acid content, and production of an unsaturated fatty acid from the unsaturated fatty acid content-enhanced stramenopiles. The modification of the fatty acid composition produced by stramenopiles, and the method for highly accumulating fatty acid in stramenopiles enabled more efficient production of polyunsaturated fatty acids.

BRIEF DESCRIPTION OF THE DRAWINGS

FIG. 28 represents multiple alignment analyses for the putative amino acid sequence of *Pinguiochrysis pyriformis*-derived Δ12 desaturase, and for the amino acid sequences of fungus- and protozoa-derived Δ12 desaturases. Multiple alignment analyses were performed for the amino acid sequences of Δ12 desaturases derived from *P. pyriformis*, fungus, and protozoan, using ClustalW 1.81 and ESPript 2.2. The same amino acid residues are indicated by blank letters over the solid background, and similar amino acid residues by bold face surrounded by solid lines. Underlines indicate commonly conserved histidine boxes. FIG. 28 includes the following sequences:

| Name | SEQ ID NO: | Source | GenBank Accession No. |
| --- | --- | --- | --- |
| PpD12Dd | SEQ ID NO: 112 | delta 12-fatty acid desaturase [*Pinguiochrysis pyriformis*] | BAK52809 |
| SdD12d | SEQ ID NO: 113 | delta-12 desaturase [*Saprolegnia diclina*] | AAR20443 |
| McD12d | SEQ ID NO: 114 | delta-12 fatty acid desaturase [*Mucor circinelloides*] | BAB69056 |
| RoD12d | SEQ ID NO: 115 | delta-12-fatty acid desaturase [*Rhizopus oryzae*] | AAV52631 |
| MaD12d | SEQ ID NO: 116 | delta-12 fatty acid desaturase [*Mortierella alpina*] | BAA81754 |
| TbD12d | SEQ ID NO: 117 | oleate desaturase [*Trypanosoma brucei*] | AAQ74969 |

Figure 29:
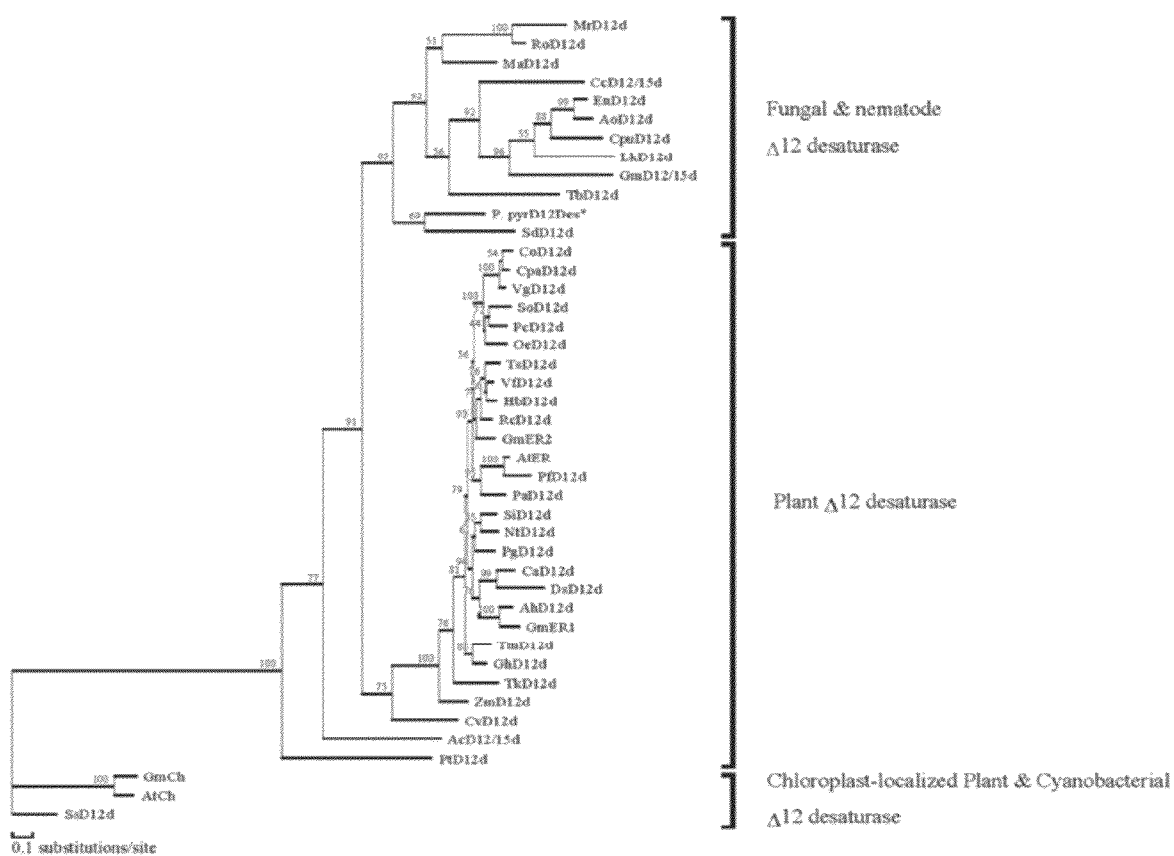

FIG. 29 represents phylogenetic analysis of Δ12 desaturase and bifunctional Δ12/Δ15 desaturase.

Figure 30:
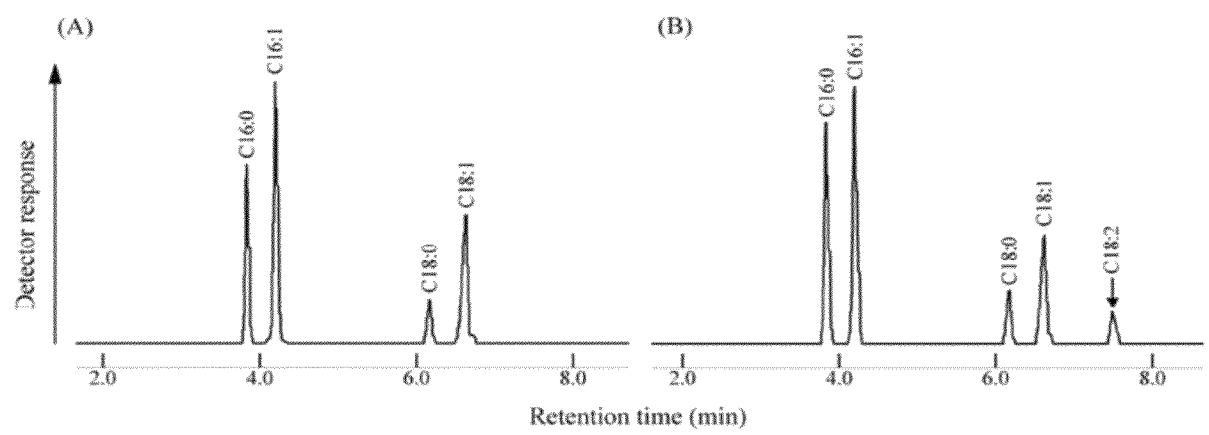

FIG. 30 represents GC analysis of fatty acid methyl ester (FAME) derived from *Saccharomyces cerevisiae* to which a control vector pYES2/CT or a recombinant plasmid pYpD12Des was introduced. Arrow indicates a new peak, with a retention time corresponding to that of the sample linoleic acid methyl ester.

Figure 31:
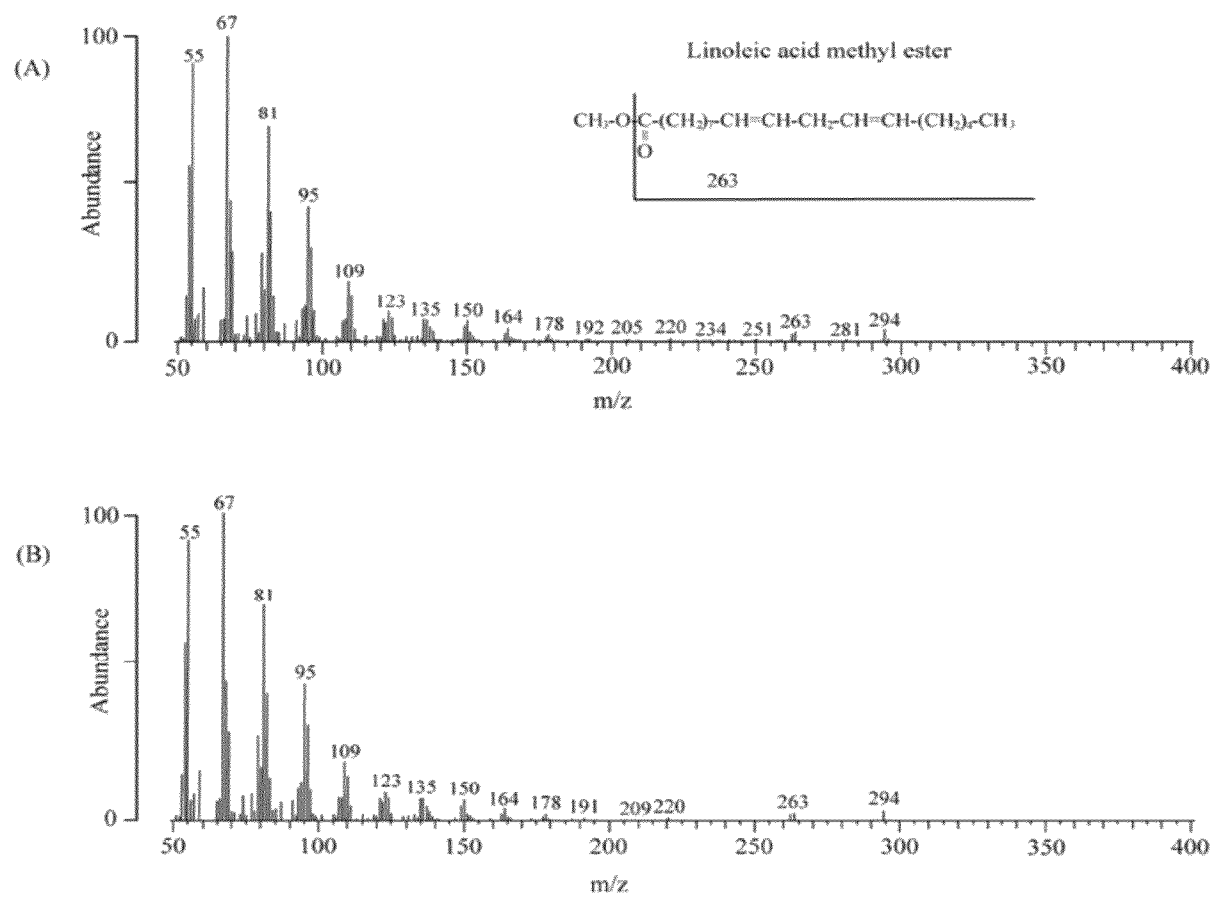

FIG. 31 represents GC-MS analysis of a new peak in pYpD12Des-introduced *S. cerevisiae*-derived FAMEs. Reference numerals: (A), standard substance of linoleic acid; (B), new peak.

Figure 32:
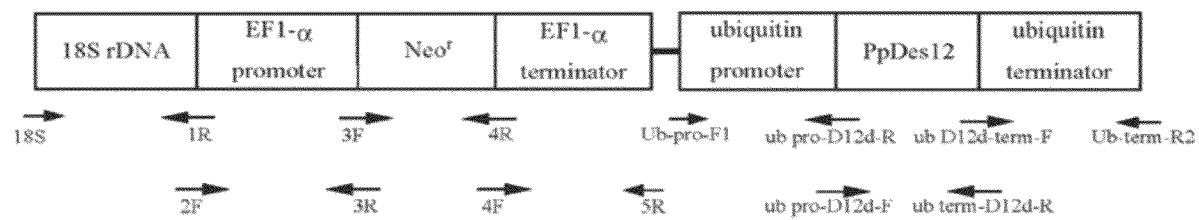

FIG. 32 is a schematic view representing a Δ12 desaturase gene/neomycin-resistant gene expression cassette. Ub-pro-F1 and Ub-term-R2 each include a KpnI site in the sequence.

Figure 33:
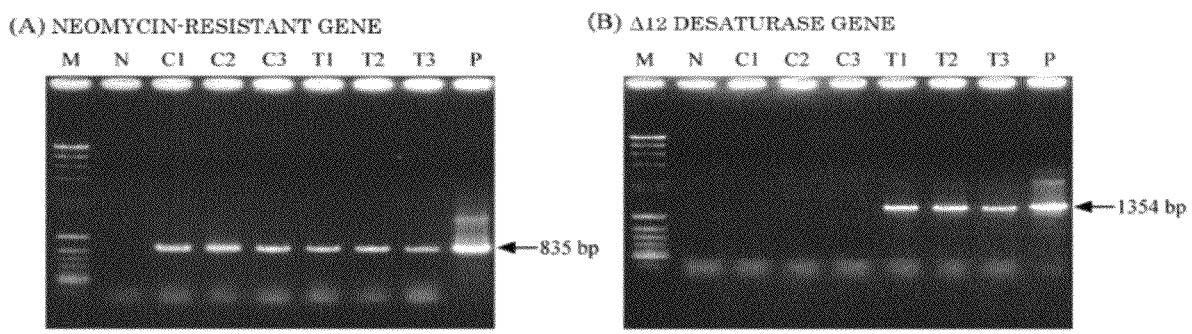

FIG. 33 represents PCR analyses of a control strain and a Δ12 desaturase gene/neomycin-resistant gene expression cassette-introduced strain, using genomic DNAs derived from these strains as templates. (A), results of amplification of neomycin-resistant gene; (B), results of amplification of Δ12 desaturase gene. Reference numerals: M: λ HindIII digest/φx-174 HincII digest; N: wild-type strain (negative control); C1: neomycin-resistant gene expression cassette-introduced strain 1 (positive control in (A); negative control in (B)); C2: neomycin-resistant gene expression cassette-introduced strain 2 (positive control in (A); negative control in (B)); C3: neomycin-resistant gene expression cassette-introduced strain 3 (positive control in (A); negative control in (B)); T1: Δ12 desaturase gene/neomycin-resistant gene expression cassette-introduced strain 1; T2: Δ12 desaturase gene/neomycin-resistant gene expression cassette-introduced strain 2; T3: Δ12 desaturase gene/neomycin-resistant gene expression cassette-introduced strain 3; P: GFP gene/neomycin-resistant gene expression cassette was used as a template (positive control).

Figure 34:
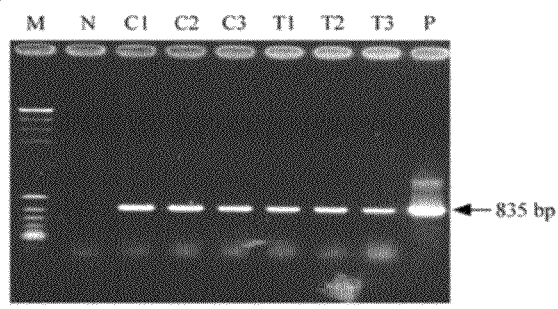
Figure 34:
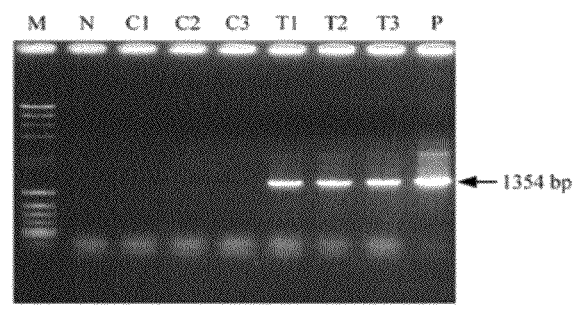

FIG. 34 represents PCR analyses of a control strain and a Δ12 desaturase gene/neomycin-resistant gene expression cassette-introduced strain, using cDNAs derived from these strains as templates. (A), results of amplification of neomycin-resistant gene; (B), results of amplification of Δ12 desaturase gene. Reference numerals: M: λ HindIII digest/φx-174 HincII digest; N: wild-type strain (negative control); C1: neomycin-resistant gene expression cassette-introduced strain 1 (positive control in (A); negative control in (B)); C2: neomycin-resistant gene expression cassette-introduced strain 2 (positive control in (A); negative control in (B)); C3: neomycin-resistant gene expression cassette-introduced strain 3 (positive control in (A); negative control in (B)); T1: Δ12 desaturase gene/neomycin-resistant gene expression cassette-introduced strain 1; T2: Δ12 desaturase gene/neomycin-resistant gene expression cassette-introduced strain 2; T3: Δ12 desaturase gene/neomycin-resistant gene expression cassette-introduced strain 3; P: GFP gene/neomycin-resistant gene expression cassette was used as a template (positive control).

Figure 35:
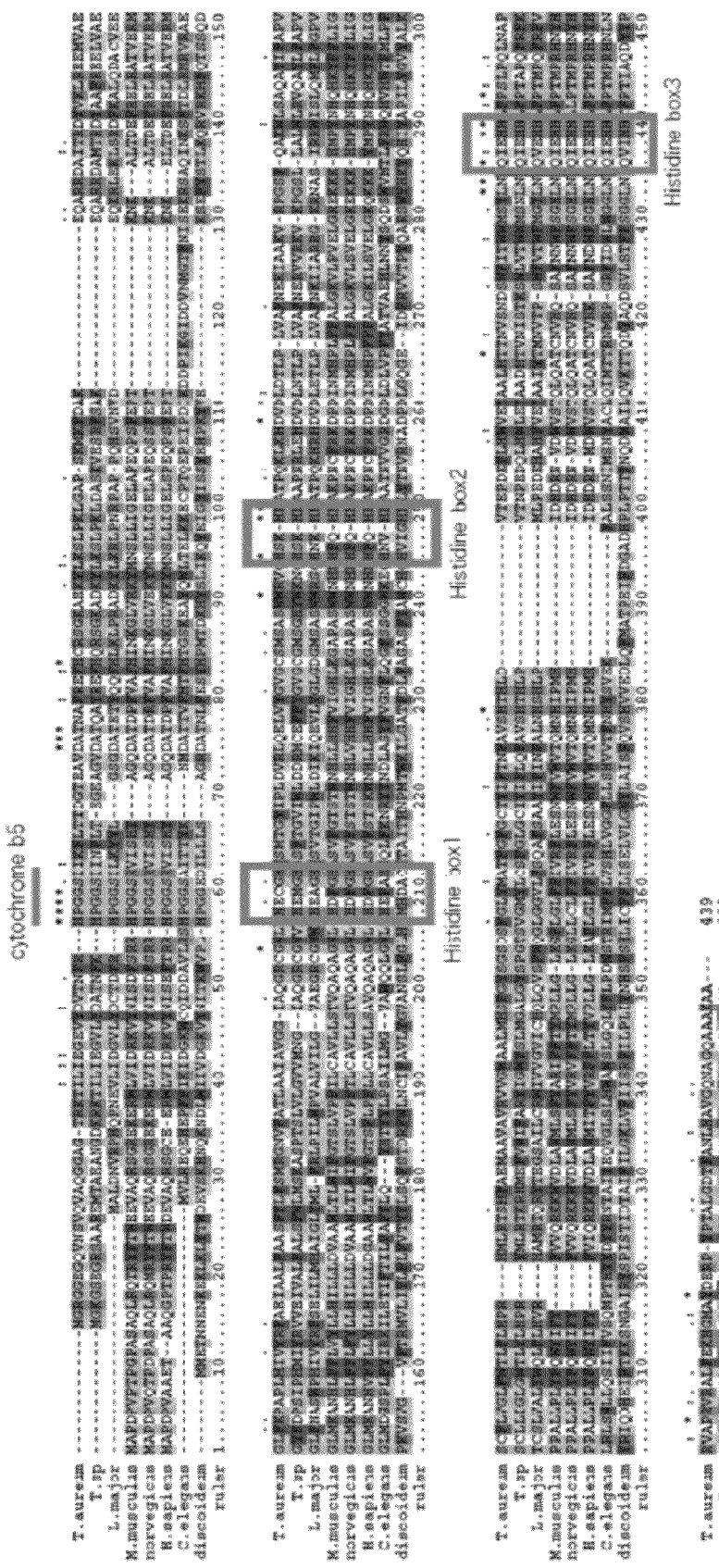

FIG. 35 represents multiple alignment of *T. aureum*-derived Δ5 desaturase. FIG. 35 includes the following sequences:

| Name | SEQ ID NO: | Source | GenBank Accession No. |
| --- | --- | --- | --- |
| T. aureum | SEQ ID NO: 118 | delta-5 desaturase [*Thraustochytrium aureum*] | BAK08911 |
| T. sp | SEQ ID NO: 119 | delta-5 fatty acid desaturase [*Thraustocytrium* sp. ATCC21685] | AAM09687 |
| L. major | SEQ ID NO: 120 | delta-5 fatty acid desaturase [*Leishmania major* strain Friedlin] | XP_001681021 |
| M. musculus | SEQ ID NO: 121 | fatty acid desaturase 1 [*Mus musculus*] | NP_666206 |
| R. norvegicus | SEQ ID NO: 122 | delta-5 desaturase [*Rattus norvegicus*] | AAG35068 |
| H. sapiens | SEQ ID NO: 123 | delta-5 desaturase [*Homo sapiens*] | AAF29378 |
| C. elegans | SEQ ID NO: 124 | Fatty acid desaturase family member (fat-4) [*Caenorhabditis elegans*] | NP_501751 |
| D. discoideum | SEQ ID NO: 125 | delta 5 fatty acid desaturase [*Dictyostelium discoideum* AX4] | XP_640331 |

Figure 36:
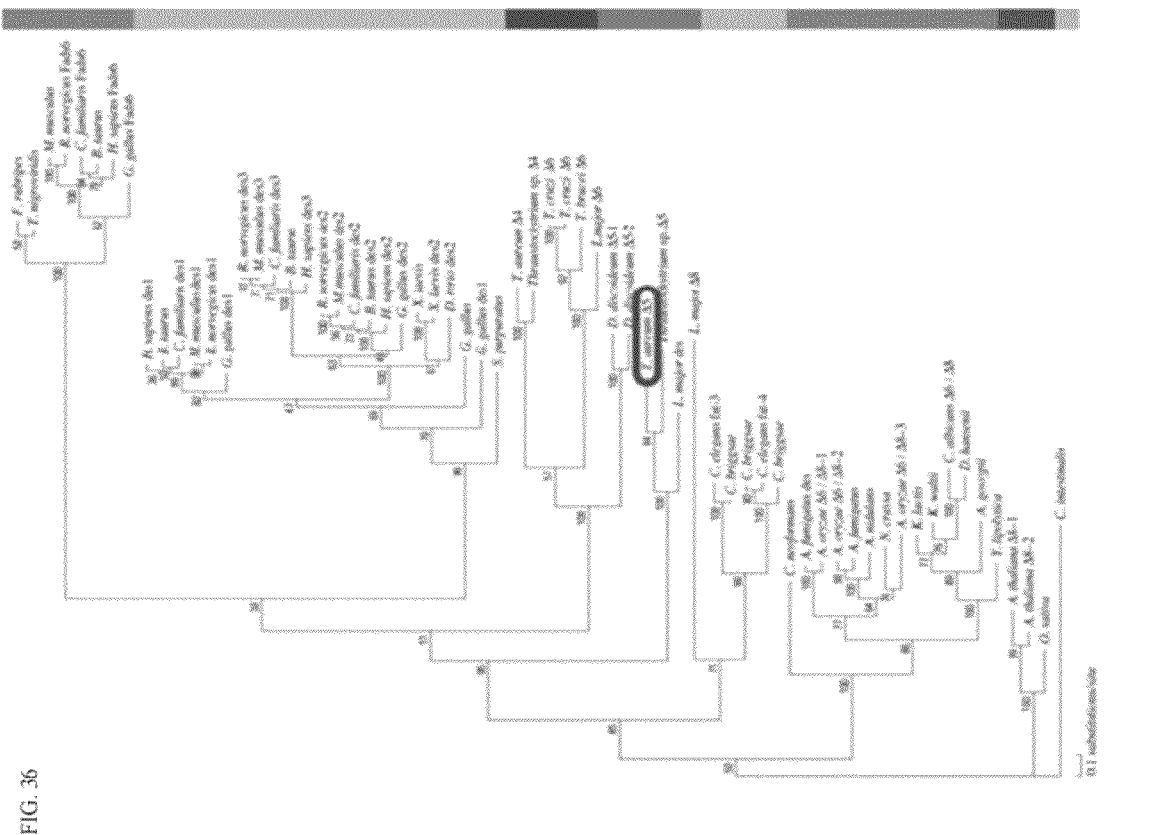

FIG. 36 represents phylogenetic analysis of desaturase.

Figure 37A:
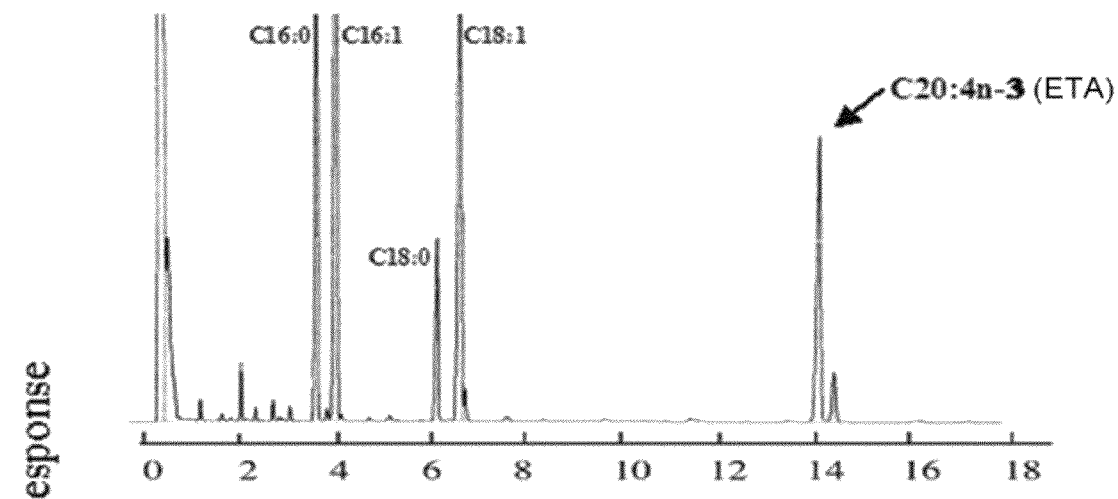
Figure 37A:
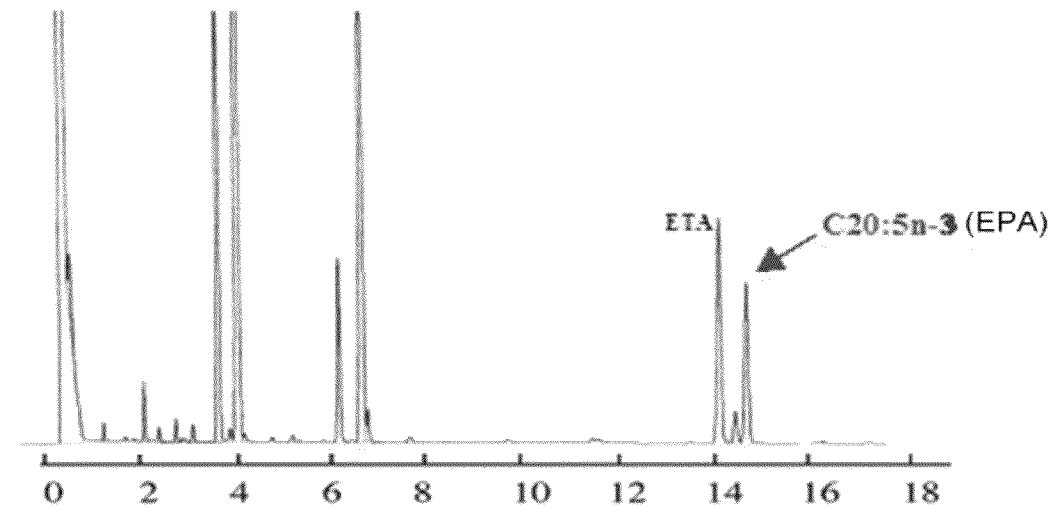

FIG. 37a represents the results of Δ5 desaturase overexpression experiment 1 using yeast as a host. (GC analysis result from ETA-containing medium).

Figure 37B:
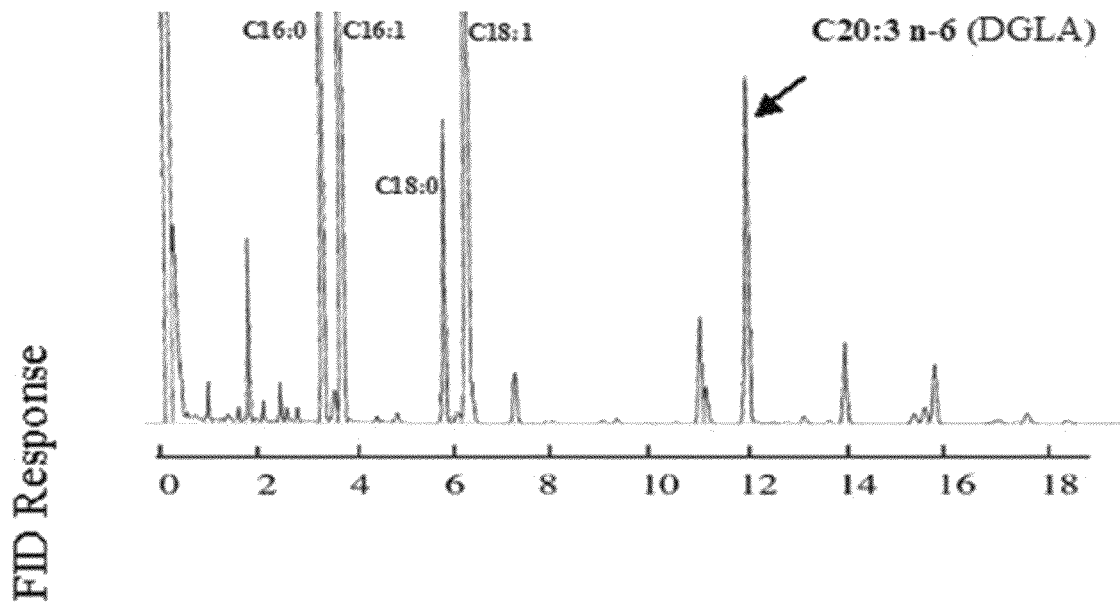
Figure 37B:
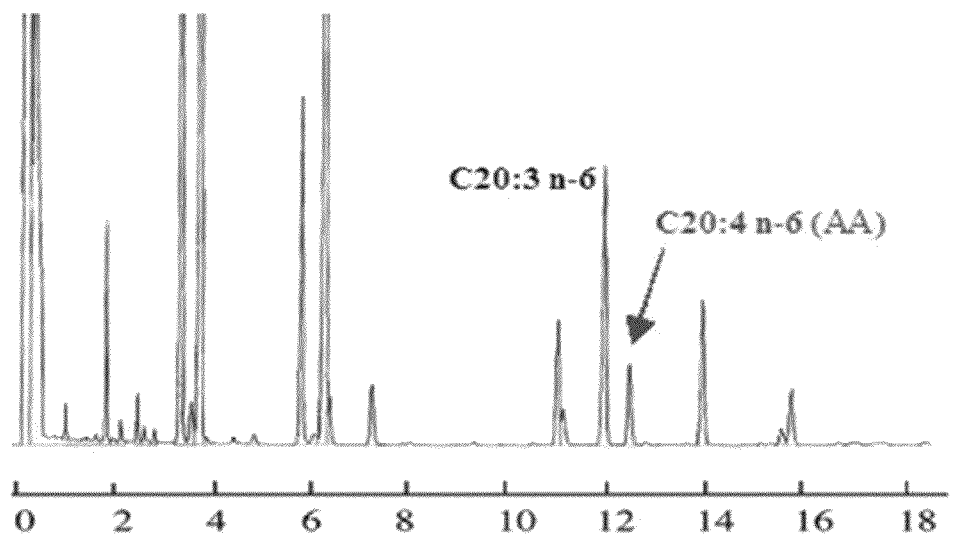

FIG. 37b represents the results of Δ5 desaturase overexpression experiment 2 using yeast as a host. (GC analysis result using DGLA-containing medium).

Figure 37C:
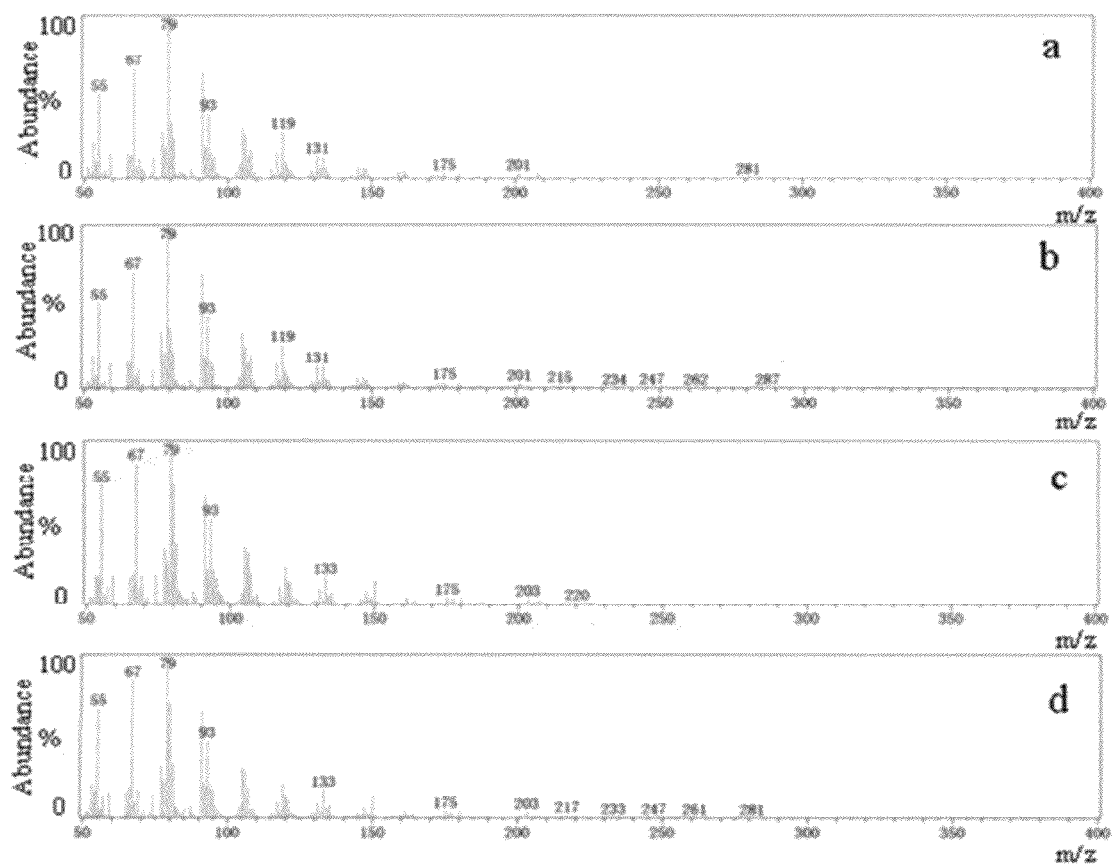

FIG. 37c represents the results of EPA and AA structure analyses by GC-MS; (a), TauΔ5des product EPA; (b), EPA standard substance: (c), TauΔ5des product AA; (d), AA standard substance.

Figure 38:
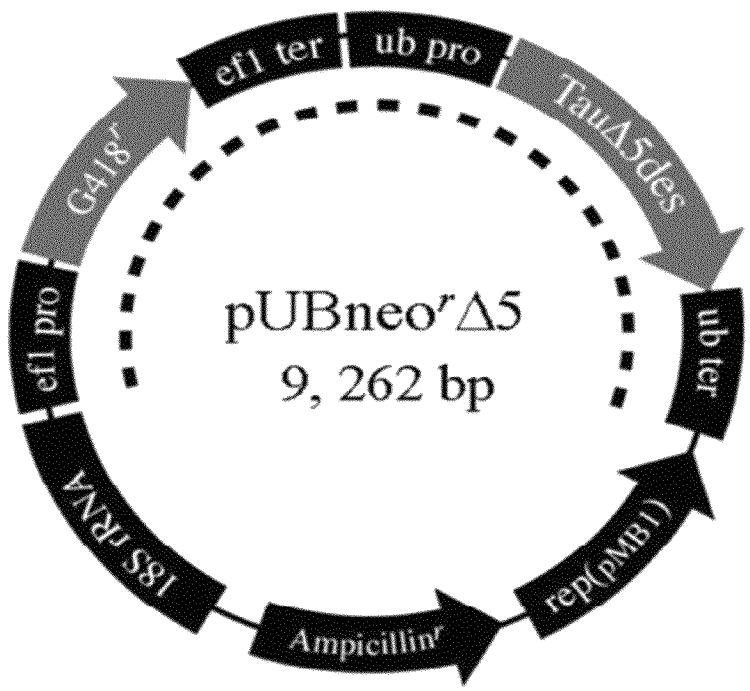
Figure 38:

FIG. 38, (a), represents a vector construct containing a Δ5 desaturase gene/neomycin-resistant gene expression cassette; (b), a PCR amplified Δ5 desaturase gene/neomycin-resistant gene expression cassette.

Figure 39:
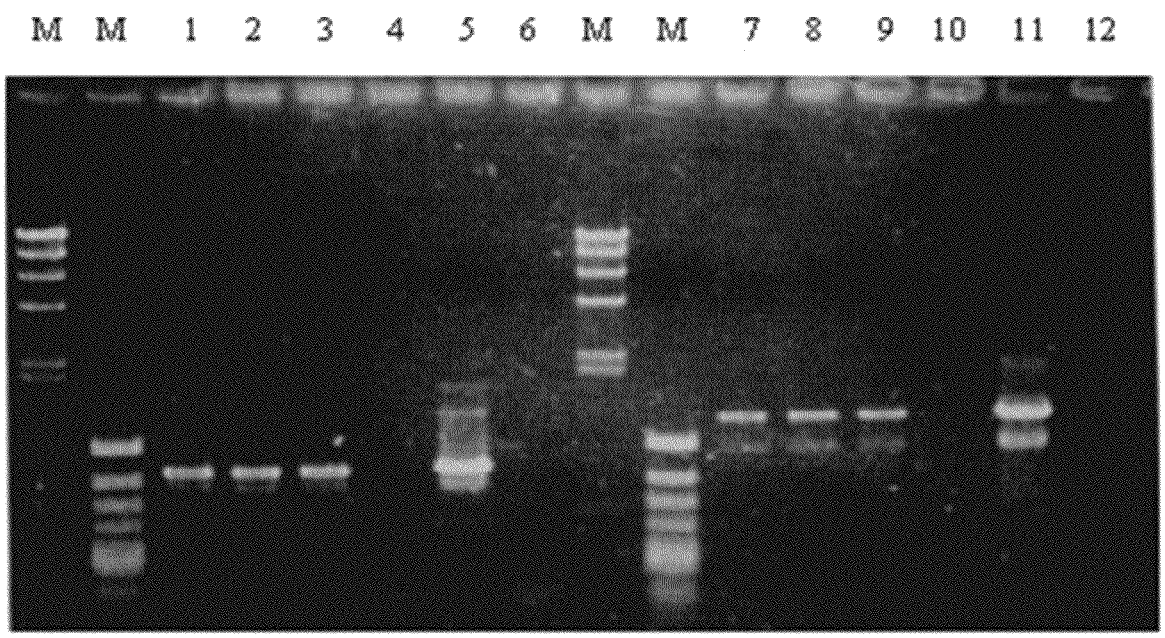

FIG. 39 represents PCR analyses of a control strain and a Δ5 desaturase gene/neomycin-resistant gene expression cassette-introduced strain, using genomic DNAs derived from these strains as templates. Lanes 1 to 6, amplified neomycin-resistant gene; Lanes 7 to 12, amplified Δ5 desaturase gene. Reference numerals: 1: Δ5 desaturase gene/neomycin-resistant gene expression cassette-introduced strain 1; 2: Δ5 desaturase gene/neomycin-resistant gene expression cassette-introduced strain 2; 3: Δ5 desaturase gene/neomycin-resistant gene expression cassette-introduced strain 3; 4: wild-type strain (negative control); 5: Δ5 desaturase gene/neomycin-resistant gene expression cassette was used as a template (positive control); 6: No template (negative control); 7: Δ5 desaturase gene/neomycin-resistant gene expression cassette-introduced strain 1; 8: Δ5 desaturase gene/neomycin-resistant gene expression cassette-introduced strain 2; 9: Δ5 desaturase gene/neomycin-resistant gene expression cassette-introduced strain 3; 10: wild-type strain (negative control); 11: Δ5 desaturase gene/neomycin-resistant gene expression cassette was used as a template (positive control); 12: No template (negative control).

Figure 40:
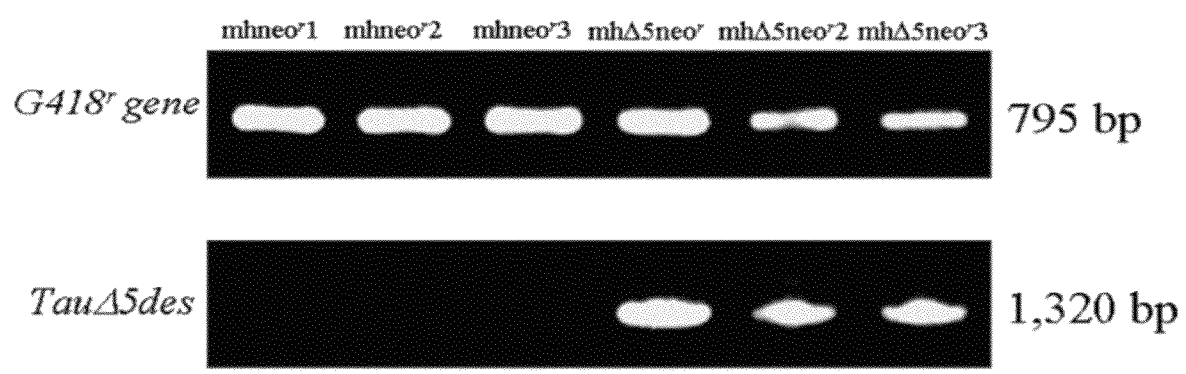

FIG. 40 represents PCR analyses of a control strain and a Δ5 desaturase gene/neomycin-resistant gene expression cassette-introduced strain, using cDNAs derived from these strains as templates. The upper panel represents the results of amplification of neomycin-resistant gene, and the lower panel represents the results of amplification of Δ5 desaturase gene. Reference numerals: mhneo$^r$1: neomycin-resistant gene expression cassette-introduced strain 1; mhneo$^r$2: neomycin-resistant gene expression cassette-introduced strain 2; mhneo$^r$3: neomycin-resistant gene expression cassette-introduced strain 3; mhΔ5neo$^r$1: Δ5 desaturase gene/neomycin-resistant gene expression cassette-introduced strain 1; mhΔ5neo$^r$2: Δ5 desaturase gene/neomycin-resistant gene expression cassette-introduced strain 2; mhΔ5neo$^r$3: Δ5 desaturase gene/neomycin-resistant gene expression cassette-introduced strain 3.

Figure 41:
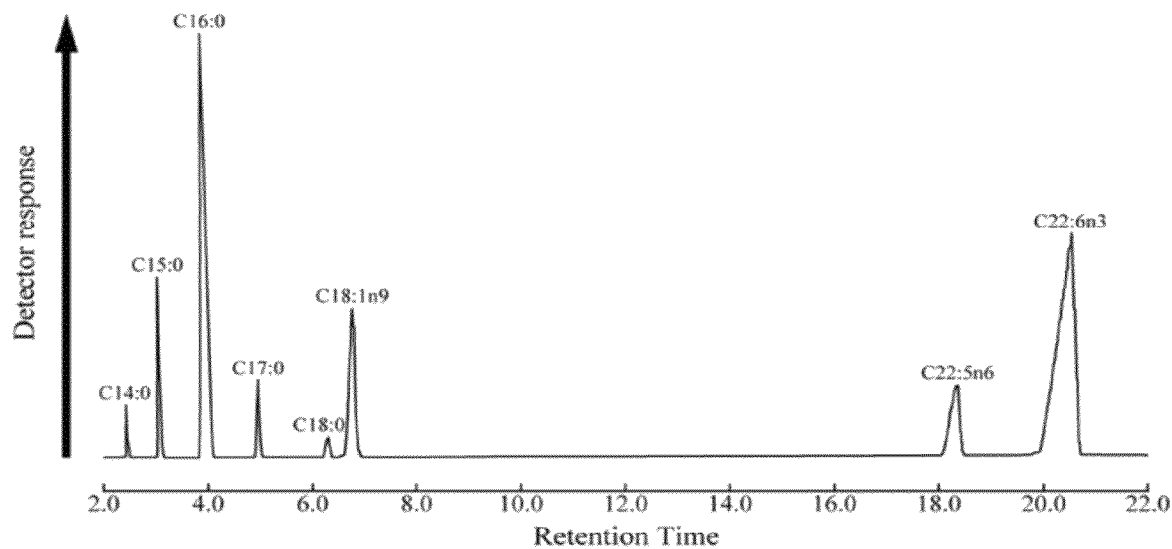
Figure 41:
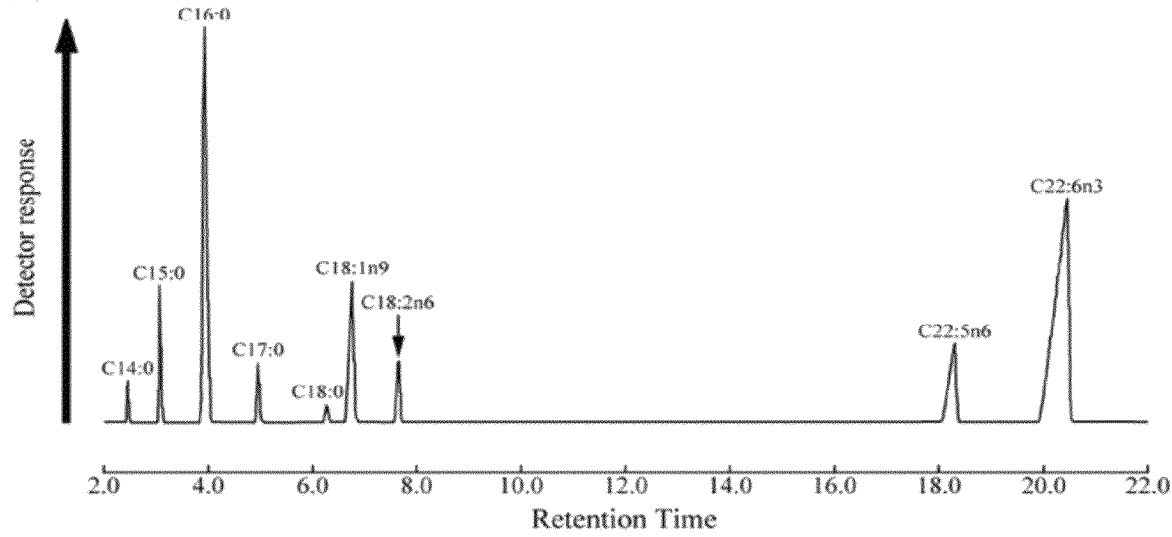

FIG. 41 represents GC analyses of FAMEs derived from a control strain or a Δ12 desaturase gene/neomycin-resistant gene expression cassette-introduced *Aurantiochytrium* sp.mh0186. Arrow indicates a new peak, with a retention time corresponding to that of the sample linoleic acid methyl ester.

Figure 42:
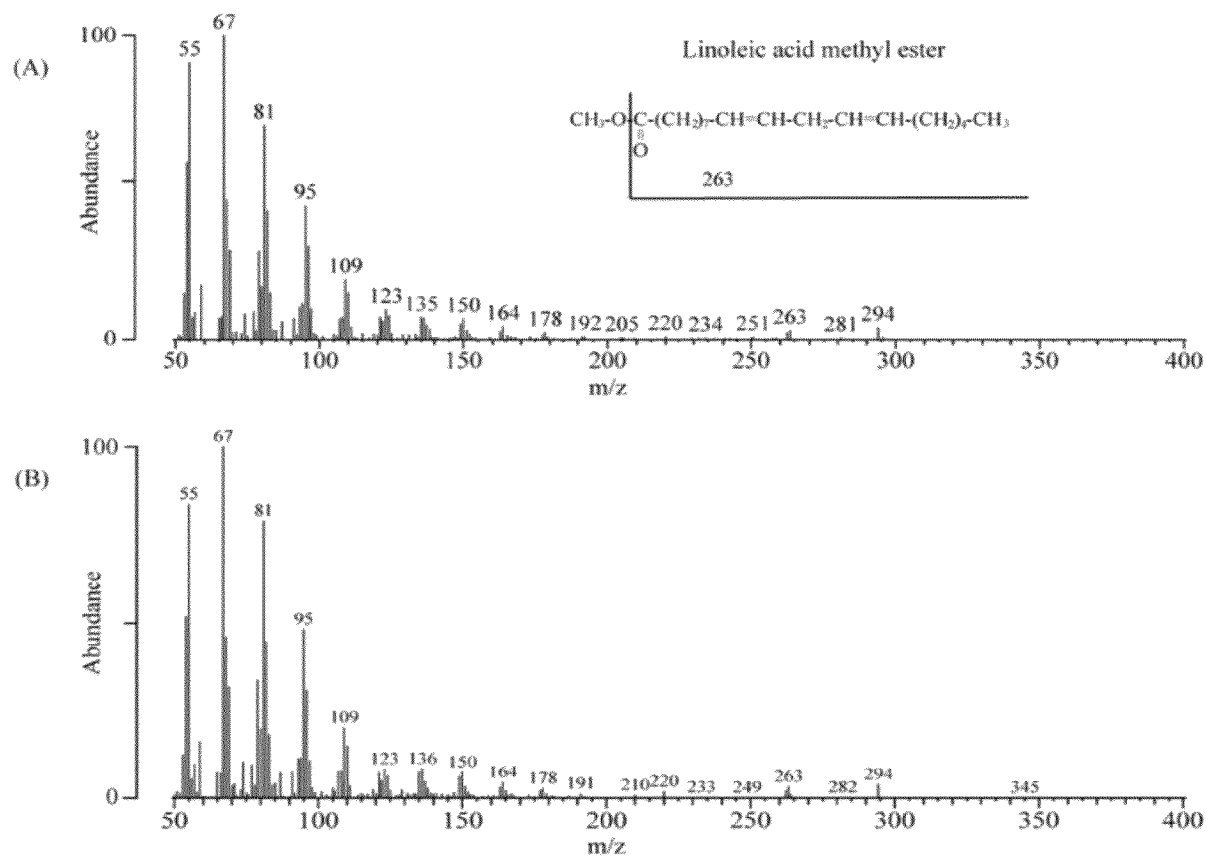

FIG. 42 represents GC-MS analyses of a new peak in Δ12 desaturase gene/neomycin-resistant gene expression cassette-introduced strain-derived FAMEs.

Figure 43:
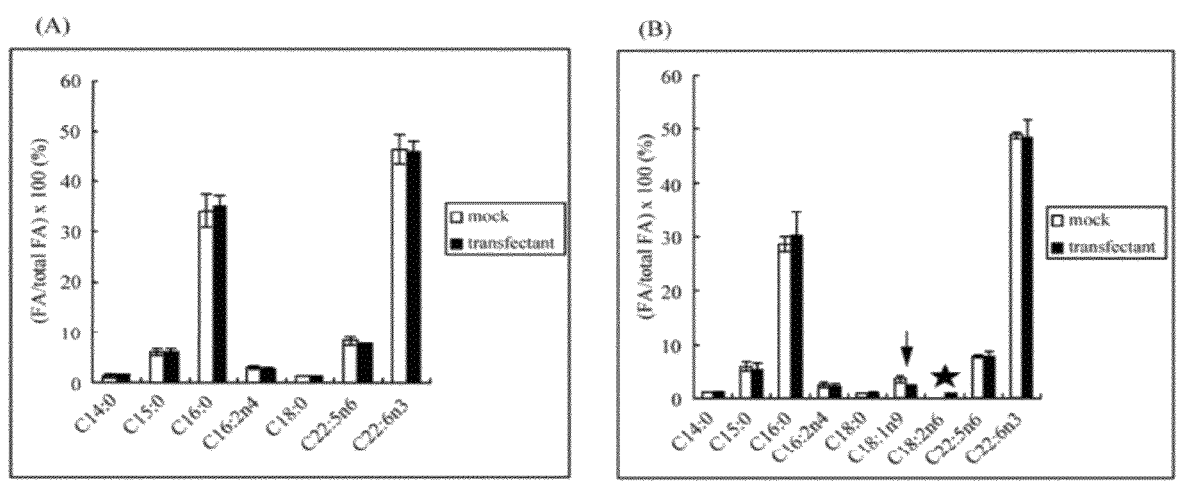

FIG. 43 compares fatty acid compositions of a control strain and a Δ12 desaturase gene/neomycin-resistant gene expression cassette-introduced strain. The blank bar and solid bar represent the fatty acid compositions of the control strain and the Δ12 desaturase gene/neomycin-resistant gene expression cassette-introduced strain, respectively. Arrow indicates the foreign fatty acid oleic acid, and the star the biosynthesized linoleic acid. Values are given as mean values±standard deviation.

Figure 44:
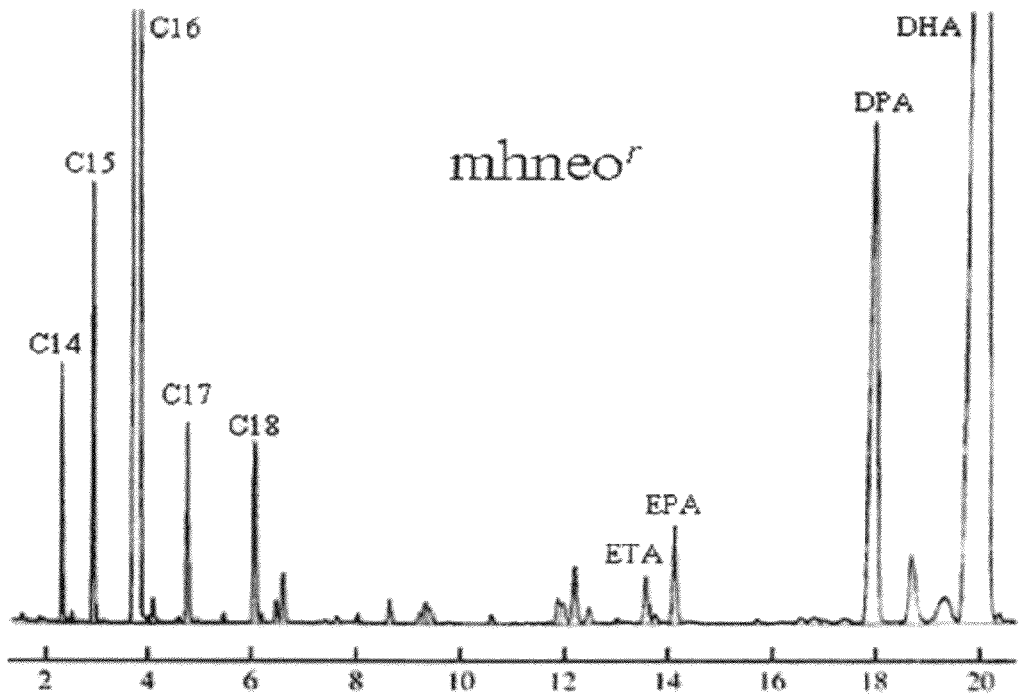
Figure 44:
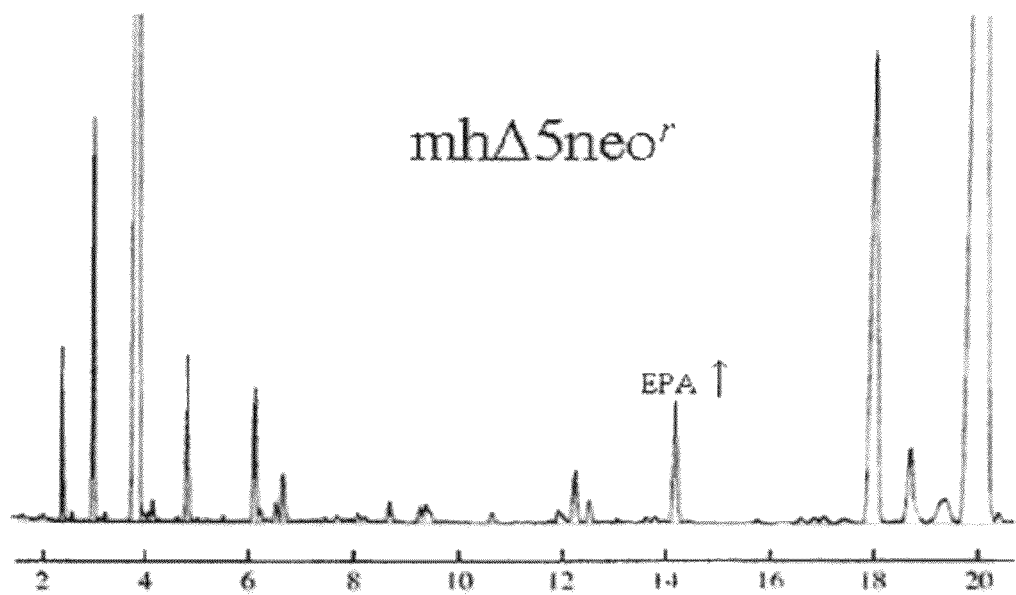

FIG. 44 represents the results of the GC analysis of a mh0186 transfectant.

Figure 45:
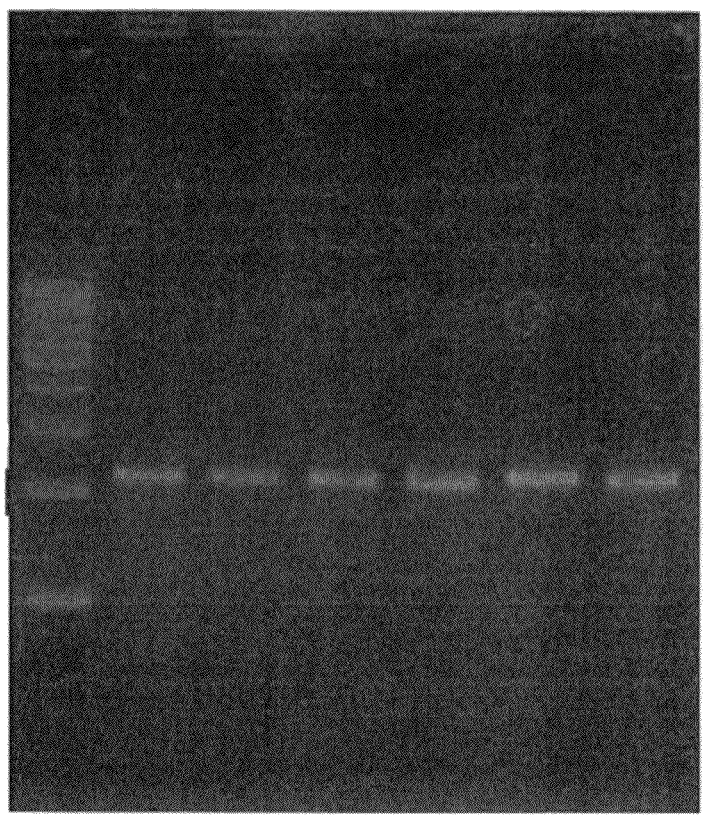

FIG. 45 represents the results of Neo$^r$ (about 2,300 bp) detection by PCR, showing that specific Neo$^r$ amplification, not found in the wild-type strain, was observed in the gene-introduced *Labyrinthula* transfectants.

Figure 46:
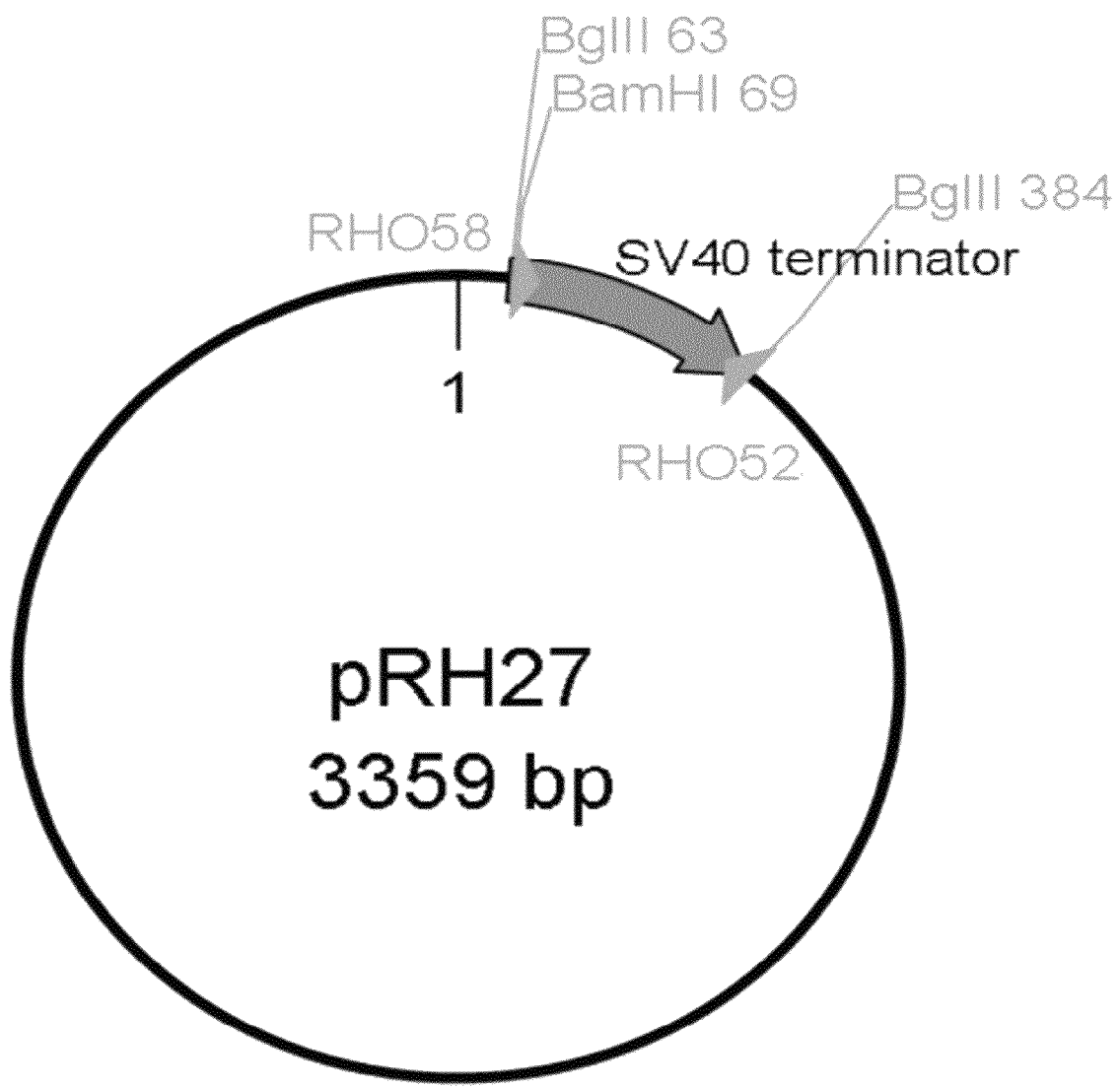

FIG. 46 represents a plasmid containing an SV40 terminator sequence derived from a subcloned pcDNA 3.1 Myc-His vector.

Figure 47:
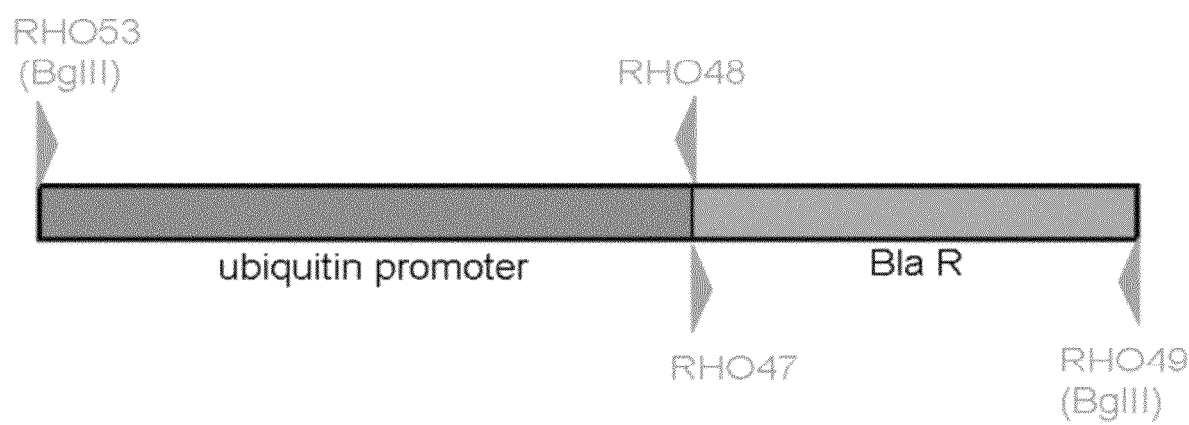

FIG. 47 is a schematic view representing primers used for Fusion PCR, and the product. The end product had a fused sequence of *Thraustochytrium aureum* ATCC 34304-derived ubiquitin promoter and pTracer-CMV/Bsd/lacZ-derived blasticidin resistant gene.

Figure 48:
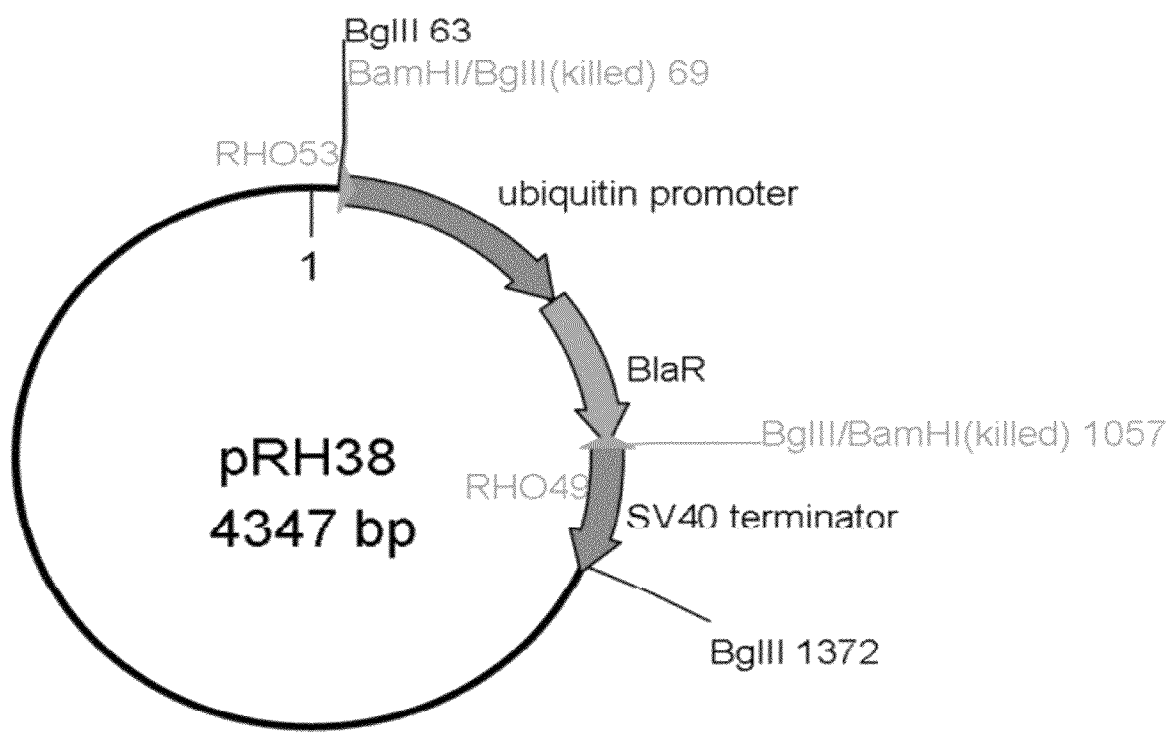

FIG. 48 represents a pTracer-CMV/Bsd/lacZ-derived blasticidin resistant gene BglII cassette produced.

Figure 49:

FIG. 49 is a schematic view representing primers used for Fusion PCR, and the product. The end product had a fused sequence of *Thraustochytrium aureum* ATCC 34304-derived ubiquitin promoter, *Saprolegnia diclina*-derived ω3 desaturase gene sequence, and *Thraustochytrium aureum* ATCC 34304-derived ubiquitin terminator.

Figure 50:
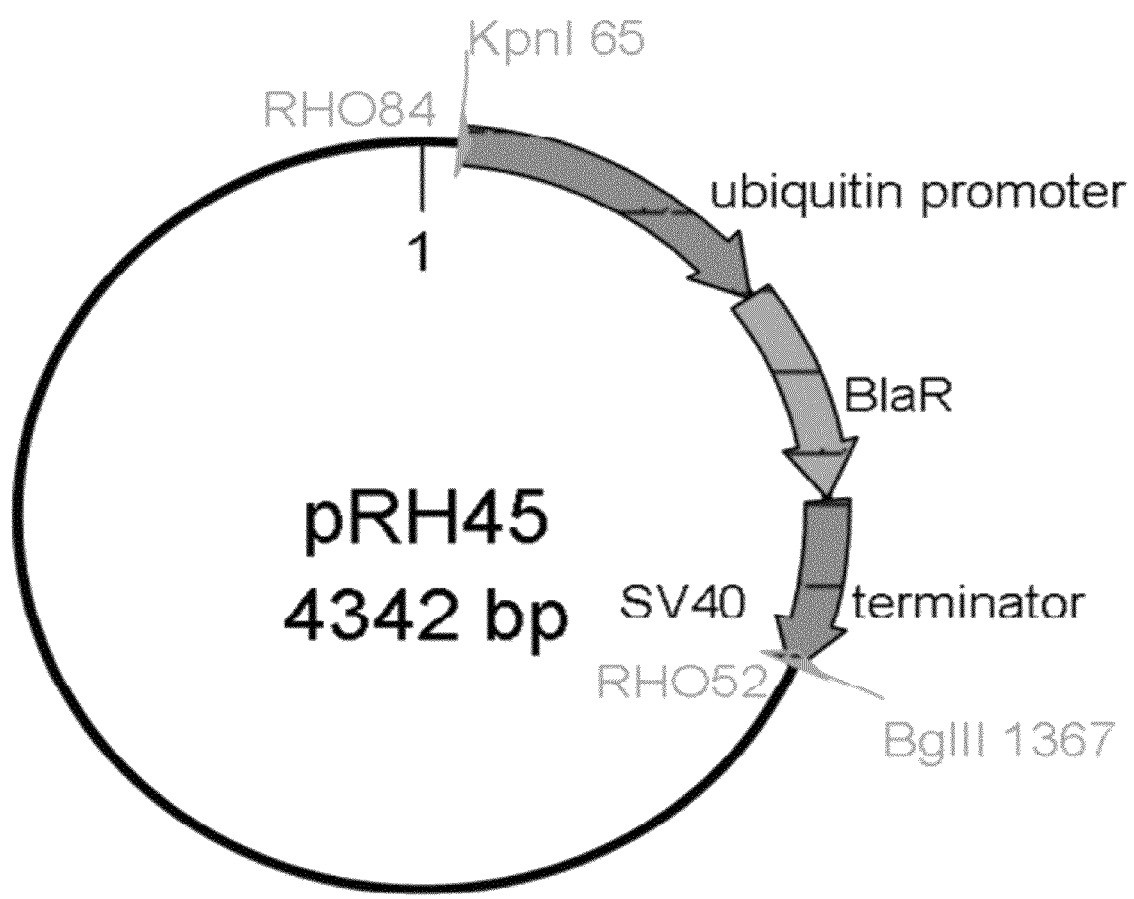

FIG. 50 represents a plasmid in which one of the BglII sites in the blasticidin resistant gene BglII cassette of FIG. 48 is replaced with a KpnI site.

Figure 51:
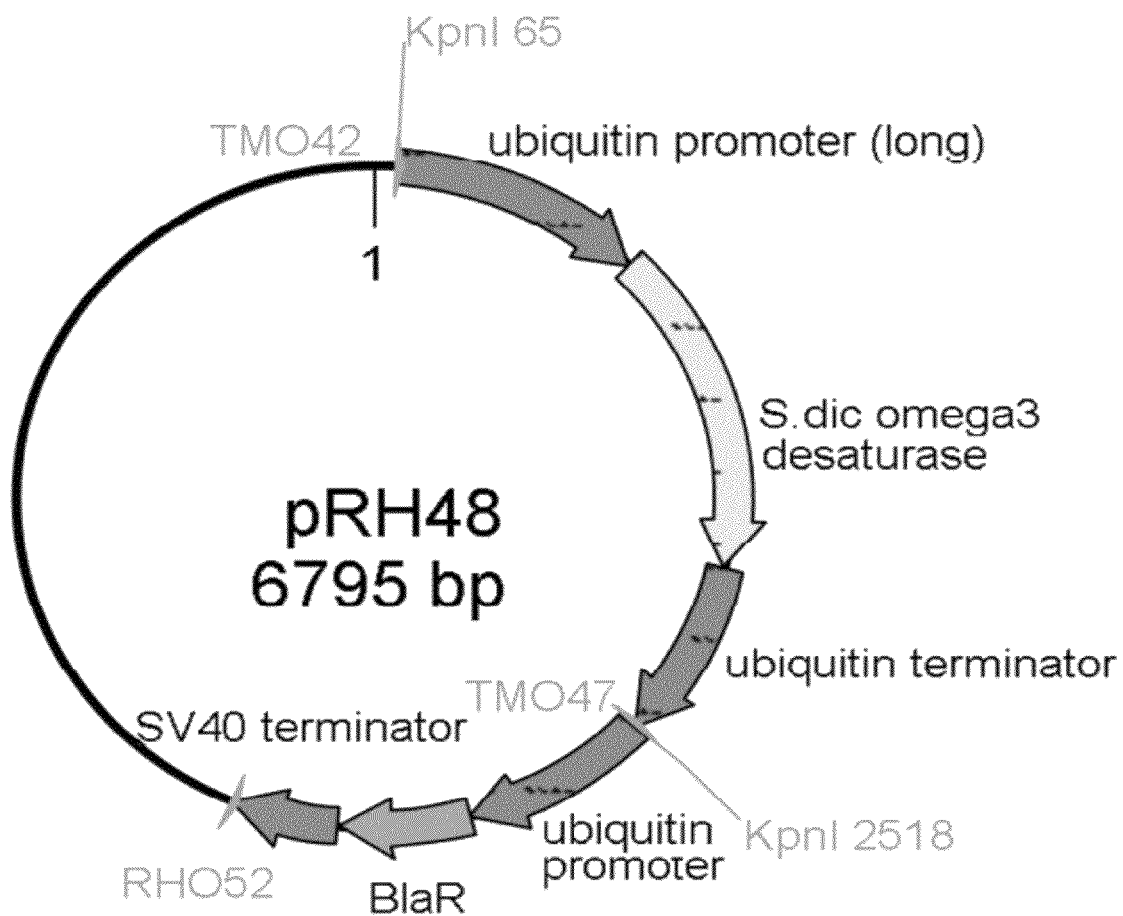

FIG. 51 represents a *Saprolegnia diclina*-derived ω3 desaturase expression plasmid produced. The plasmid includes a blasticidin resistant gene as a drug resistance marker.

Figure 52:
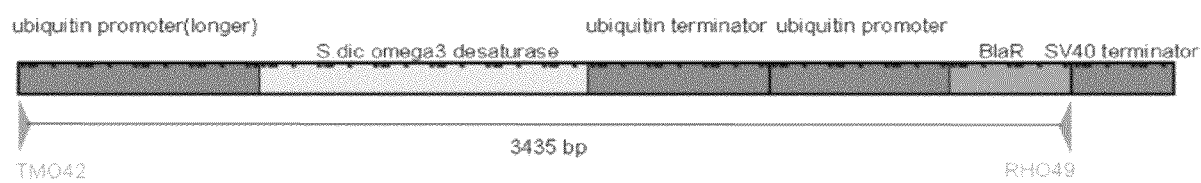

FIG. 52 is a schematic view representing positions of the primers used for a PCR performed to confirm insertion of *Saprolegnia diclina*-derived ω3 desaturase gene into the genome.

Figure 53:
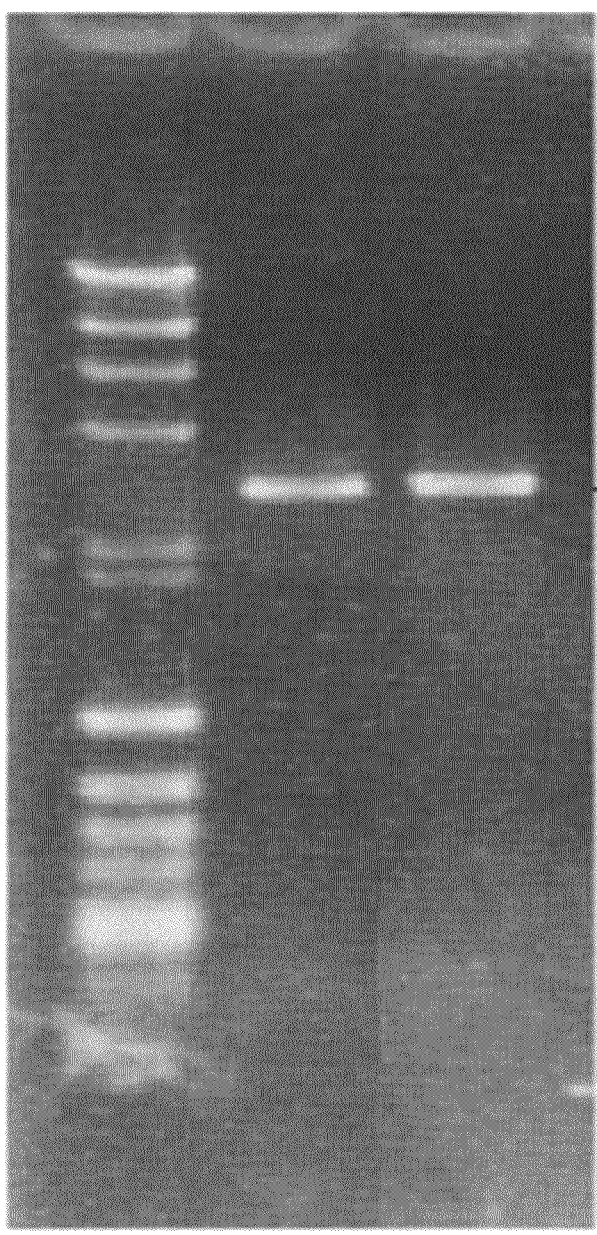

FIG. 53 represents evaluations of a *Thraustochytrium aureum* ATCC 34304 transfectant strain by PCR using genomic DNA as a template. Reference numerals: Lanes 1 and 2: transfectant.

Figure 54:
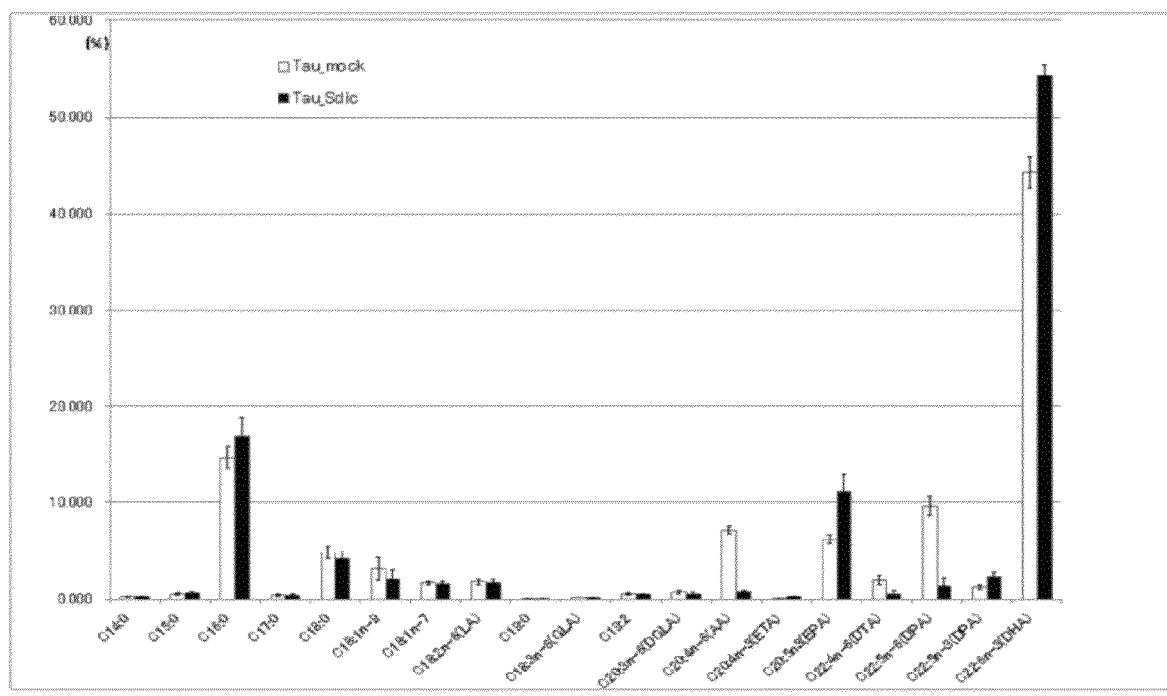

FIG. 54 compares the fatty acid compositions of a *Thraustochytrium aureum* ATCC 34304 control strain and an ω03 desaturase gene introduced strain. The blank bar and solid bar represent the fatty acid compositions of the control strain and the ω3 desaturase gene introduced strain, respectively. Values are given as mean values±standard deviation.

FIG. 55 represents the percentage of fatty acids in the control strain and the ω3 desaturase gene introduced strain relative to the percentage of the *Thraustochytrium aureum* ATCC 34304 wild-type strain taken as 100%.

MODE FOR CARRYING OUT THE INVENTION

The recent studies of the physiological activity and the pharmacological effects of lipids have elucidated the conversion of unsaturated fatty acids into various chemical substances, and the roles of unsaturated fatty acids in the unsaturated fatty acid metabolism. Particularly considered important in relation to disease is the nutritionally preferred proportions of saturated fatty acids, monounsaturated fatty acids, and unsaturated fatty acids, and the proportions of fish oil-derived ω3 series (also known as the n-3 series) fatty acids such as eicosapentaenoic acid and docosahexaenoic acid, and plant-derived ω6 series (also known as the n-6 series) fatty acids as represented by linoleic acid. Because animals are deficient in fatty acid desaturases (desaturases) or have low levels of fatty acid desaturases, some unsaturated fatty acids need to be ingested with food. Such fatty acids are called essential fatty acids (or vitamin F), which include linoleic acid (LA), γ-linolenic acid (GLA), and arachidonic acid (AA or ARA).

Unsaturated fatty acid production involves enzymes called fatty acid desaturases (desaturases). The fatty acid desaturases (desaturases) are classified into two types: (1) those creating a double bond (also called an unsaturated bond) at a fixed position from the carbonyl group of a fatty acid (for example, Δ9 desaturase creates a double bond at the 9th position as counted from the carbonyl side), and (2) those creating a double bond at a specific position from the methyl end of a fatty acid (for example, ω3 desaturase creates a double bond at the 3rd position as counted from the methyl end). It is known that the biosynthesis of unsaturated fatty acid involves the repetition of a set of two reactions, the creation of a double bond by the desaturase (unsaturation), and the elongation of the chain length by several different elongases. For example, Δ9 desaturase synthesizes oleic acid (OA) by unsaturating the stearic acid either synthesized in the body from palmitic acid or ingested directly. Δ6, Δ5, and Δ4 desaturases are fatty acid desaturases (desaturases) essential for the syntheses of polyunsaturated fatty acids such as arachidonic acid (AA), eicosapentaenoic acid (EPA), and docosahexaenoic acid (DHA).

The Labyrinthulomycetes, a member of stramenopiles, has two families: *Thraustochytrium* (Thraustochytriaceae) and Labyrinthulaceae. These microorganisms are known to accumulate polyunsaturated fatty acids such as arachidonic acid, EPA, DTA, DPA, and DHA.

The present invention is concerned with a stramenopiles transformation method that introduces a foreign gene into a stramenopiles. The transformation method of the present invention is the basis for providing a novel modification method of a fatty acid composition produced by stramenopiles, a novel method for highly accumulating fatty acids in a stramenopiles, and a novel unsaturated fatty acid producing process. The transformation method has also made it possible to develop and provide a stramenopiles having an enhanced unsaturated fatty acid content conferred by the introduction of a fatty acid desaturase gene, and a method for producing unsaturated fatty acids from the unsaturated fatty acid content-enhanced stramenopiles.

The present invention is described below in more detail.

[Microorganism]

The microorganisms used in the fatty acid modification method of the present invention are not particularly limited, as long as the microorganisms are stramenopiles considered to carry out fatty acid synthesis after introduction of a fatty acid desaturase gene. Particularly preferred microorganisms are those belonging to the class Labyrinthulomycetes. Examples of the Labyrinthulomycetes include those of the genus *Labyrinthula, Althornia, Aplanochytrium, Japonochytrium, Labyrinthuloides, Schizochytrium, Thraustochytrium, Ulkenia, Aurantiochytrium, Oblongichytrium, Botryochytrium, Parietichytrium*, and *Sicyoidochytrium*.

The stramenopiles used in the present invention are preferably those belonging to the genus *Schizochytorium, Thraustochytrium, Aurantiochytrium*, and *Parietichytrium*, particularly preferably a *Schizochytrium* sp. M-8 strain (FERM P-19755), *Thraustochytrium aureum* ATCC34304, *Thraustochytrium* sp. ATCC26185, *Schizochytrium* sp. AL1Ac, *Schizochytrium aggregatum* ATCC28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 (FERM ABP-11298). The *Schizochytrium* sp. M-8 strain is reported in Patent Document 5, and was acquired according to the method described in this publication (*Thraustochytrium* M-8 strain). First, the sea water and fallen leaves collected in the mangrove forest on Ishigakijima were placed in a 300-ml Erlenmeyer flask, and about 0.05 g of pine pollens (collected at the shore near the city of Miyazaki) were added. The sample was left unattended at room temperature for one week, and the sea water was collected with the pine pollens floating on the surface. The water (0.1 ml) was then applied onto a potato dextrose agar medium prepared in a petri dish. The sample was cultured at 28° C. for 5 days, and cream-colored, non-glossy colonies were picked up, and applied onto a new agar medium. After 3 days, the proliferated microorganisms were observed under a microscope, and preserved in a slant medium after determining the microorganisms as Labyrinthulomycetes from the cell size and morphology. Note that this strain has been domestically deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM P-19755; Mar. 29, 2004). The *Parietichytrium sarkarianum* SEK364 strain was obtained from the surface water collected at the mouth of fukidougawa on Ishigakijima. The water (10 ml) was placed in a test tube, and left unattended at room temperature after adding pine pollens. After 7 days, the pine pollens were applied to a sterile agar medium (2 g glucose, 1 g peptone, 0.5 g yeast extract, 0.2 g chloramphenicol, 15 g agar, distilled water 100 mL, sea water 900 mL). Colonies appearing after 5 days were isolated, and cultured again. This was repeated several times to isolate the cells. Note that this strain has been internationally deposited, and is available from The National Institute of Advanced Industrial Science and Technology, International Patent Organism Depositary (Tsukuba Center, Chuou Dairoku, 1-1-1, Higashi, Tsukuba-shi, Ibaraki) (accession number: FERM ABP-11298; Sep. 24, 2010).

It should be noted that the stramenopiles are also referred to by other names in literatures: *Schizochytorium* sp. mh0186, *Aurantiochytirum* sp. mh0186, or *Aurantiochytrium limacinum* mh0186. These names are also referred to in the present invention. These stramenopiles are cultured in common media, including solid medium and liquid medium, using an ordinary method. The type of medium used is not particularly limited, as long as it is one commonly used for culturing Labyrinthulomycetes, and that contains, for example, a carbon source (such as glucose, fructose, saccharose, starch, and glycerine), a nitrogen source (such as a yeast extract, a corn steep liquor, polypeptone, sodium glutamate, urea, ammonium acetate, ammonium sulfate, ammonium nitrate, ammonium chloride, and sodium nitrate), an inorganic salt (such as potassium phosphate) and appropriately combined with other necessary components. The prepared medium is adjusted to a pH of 3.0 to 8.0, and used after being sterilized with an autoclave or the like. The *Thraustochytrium aureum* ATCC 34304, *Thraustochytrium* sp. ATCC 26185, *Schizochytrium aggregatum* ATCC 28209, and *Ulkenia* sp. ATCC 28207 are deposited and available from ATCC. The *Schizochytrium* sp. SEK210 (NBRC 102615), *Schizochytrium* sp. SEK345 (NBRC 102616), and *Botryochytrium radiatum* SEK353 (NBRC 104107) are deposited and available from The National Institute of Technology and Evaluation.

[Fatty Acid Desaturase]

The fatty acid desaturase (desaturase) of the present invention is not particularly limited, as long as it functions as a fatty acid desaturase. The origin of the fatty acid desaturase gene is not particularly limited, and may be, for example, animals and plants. Examples of the preferred fatty acid desaturase genes include Δ4 fatty acid desaturase gene, Δ5 fatty acid desaturase gene, Δ6 fatty acid desaturase gene, and Δ12 fatty acid desaturase gene, and these may be used either alone or in combination. The Δ4 fatty acid desaturase gene, Δ5 fatty acid desaturase gene, Δ6 fatty acid desaturase gene, and Δ12 fatty acid desaturase gene create an unsaturated bond at carbon 4, 5, 6, and 12, respectively, as counted from the terminal carboxyl group (delta end) of the fatty acid. A specific example of these fatty acid desaturase genes is the microalgae-derived Δ4 fatty acid desaturase gene (Tonon, T., Harvey, D., Larson, T. R., and Graham, I. A. Identification of a very long chain polyunsaturated fatty acid Δ4-desaturase from the microalga Pavlova lutheri; Non-Patent Document 5). Specific examples of Δ5 desaturase include *T. aureum*-derived Δ5 desaturase, and Δ5 desaturases derived from *Thraustochytrium* sp. ATCC 26185, *Dictyostelium discoideum, Rattus norvegicus, Mus musculus, Homo sapiens, Caenorhabditis elegans*, and *Leishmania major*. Examples of Δ12 desaturase include *Pinguio-*

*chrysis pyriformis*-derived Δ12 desaturase, and fungus- and protozoa-derived Δ12 desaturases.

Desaturase is essential for the production of polyunsaturated fatty acids having many important functions. For example, polyunsaturated fatty acids are the main component of the cell membrane, and exist in the form of phospholipids. The fatty acids also function as precursor substances of mammal prostacyclin, eicosanoid, leukotriene, and prostaglandin. Polyunsaturated fatty acids are also necessary for the proper development of a growing infant brain, and tissue formation and repair. Given the biological significance of the polyunsaturated fatty acids, there have been attempts to efficiently produce polyunsaturated fatty acids, and intermediates of polyunsaturated fatty acids.

Δ5 desaturase catalyzes, for example, the conversion of dihomo-γ-linolenic acid (DGLA) to arachidonic acid (AA), and the conversion of eicosatetraenoic acid (ETA) to eicosapentaenoic acid (EPA). Δ6 desaturase catalyzes, for example, the conversion of linoleic acid (LA) to γ-linolenic acid (GLA), and the conversion of α-linolenic acid (ALA) to stearidonic acid (STA). Aside from Δ5 desaturase and Δ6 desaturase, many other enzymes are involved in the polyunsaturated fatty acid biosynthesis. For example, elongase catalyzes the conversion of γ-linolenic acid (GLA) to dihomo-γ-linolenic acid (DGLA), and the conversion of stearidonic acid (STA) to eicosatetraenoic acid (ETA). Linoleic acid (LA) is produced from oleic acid (OA) by the action of Δ12 desaturase.

[Product Unsaturated Fatty Acid]

The unsaturated fatty acid produced by the fatty acid desaturase expressed in stramenopiles are, for example, an unsaturated fatty acid of 18 to 22 carbon atoms. Preferred examples include docosahexaenoic acid (DHA) and eicosapentaenoic acid (EPA), though the preferred unsaturated fatty acids vary depending on the types of the fatty acid desaturase and the fatty acid substrate used. Other examples include α-linolenic acid (ALA), octadecatetraenoic acid (OTA, 18:4n-3), eicosatetraenoic acid (ETA, 20:4n-3), n-3 docosapentaenoic acid (DPA, 22:5n-3), tetracosapentaenoic acid (TPA, 24:5n-3), tetracosahexaenoic acid (THA, 24:6n-3), linoleic acid (LA), γ-linolenic acid (GLA), eicosatrienoic acid (20:3n-6), arachidonic acid (AA), and n-6 docosapentaenoic acid (DPA, 22:5n-6).

[Fatty Acid Desaturase Gene Source]

The organisms that can be used as the fatty acid desaturase gene source in the present invention are not limited to particular genus, species, or strains as described in paragraph [0021], and may be any organisms having an ability to produce polyunsaturated fatty acids. For example, in the case of microorganisms, such organisms are readily available from microorganism depositary authorities. Examples of such microorganisms include the bacteria *Moritella marina* MP-1 strain (ATCC15381) of the genus *Moritella*. The following describes a method using this strain as an example of desaturase and elongase gene sources. The method, however, is also applicable to the isolation of the constituent desaturase and elongase genes from all biological species having the desaturase/elongase pathway.

Isolation of the desaturase and/or elongase gene from the MP-1 strain requires estimation of a conserved region in the amino acid sequence of the target enzyme gene. For example, in desaturase, it is known that a single cytochrome b5 domain and three histidine boxes are conserved across biological species, and that elongase has two conserved histidine boxes across biological species. More specifically, the conserved region of the target enzyme can be estimated by the multiple alignment comparison of the known amino acid sequences of the desaturase or elongase genes derived from various biological species using the clustal w program (Thompson, J. D., et al.; Non-Patent Document 6). It is also possible to estimate conserved regions specific to desaturase and/or elongase having the same substrate specificity by the multiple alignment comparison of the amino acid sequences of desaturase or elongase genes having the same substrate specificity in the desaturase and/or elongase derived from known other organisms. Various degenerate oligonucleotide primers are then produced based on the estimated conserved regions, and the partial sequence of the target gene derived from the MP-1 strain is amplified using an MP-1 strain-derived cDNA library as a template, by using methods such as PCR and RACE. The resulting amplification product is cloned into a plasmid vector, and the base sequence is determined using an ordinary method. The sequence is then compared with a known enzyme gene to confirm isolation of a part of the target enzyme gene from the MP-1 strain. The full-length target enzyme gene can be obtained by hybridization screening using the obtained partial sequence as a probe, or by the RACE technique using the oligonucleotide primers produced from the partial sequence of the target gene.

[Other Gene Sources]

Reference should be made to Non-Patent Document 7 or 8 for GFP (Green Fluorescent Protein), Patent Document 6 for EGFP (enhanced GFP), and Non-Patent Document 9 for neomycin-resistant gene.

[Introduction and Expression of Fatty Acid Desaturase in Stramenopiles]

The fatty acid desaturase gene may be introduced by way of transformation using the conventional method of gene introduction into a microorganism. An example of such a method is the transformation introducing a recombinant expression vector into a cell. Details of the desaturase gene introduction into stramenopiles in the present invention will be specifically described later in Examples. The stramenopiles used for transformation are not particularly limited, and those belonging to the class Labyrinthulomycetes can preferably be used, as described above.

The expression vector is not particularly limited, and a recombinant expression vector with an inserted gene may be used. The vehicle used to produce the recombinant expression vector is not particularly limited, and, for example, a plasmid, a phage, and a cosmid may be used. A known method may be used for the production of the recombinant expression vector. The vector is not limited to specific types, and may be appropriately selected from vectors expressible in a host cell. Specifically, the expression vector may be one that is produced by incorporating the gene of the present invention into a plasmid or other vehicles with a promoter sequence appropriately selected according to the type of the host cell for reliable expression of the gene. The expression vector preferably includes at least one selection marker. Examples of the marker for eukaryotic cell cultures include dihydrofolate reductase, a neomycin-resistant gene, and a GFP. In consideration of the results for antibiotic sensitivity and the selection marker genes used in the eukaryotes transformation system, the selection marker genes presented in Table 1 below were shown to be effective for the Labyrinthulomycetes transformation system.

These selection markers allow for confirmation of whether the polynucleotide according to the present invention has been introduced into a host cell, or whether the polynucleotide is reliably expressed in the host cell. Alternatively, the fatty acid desaturase according to the present invention may be expressed as a fused polypeptide. For example, the fatty acid desaturase according to the present invention may be expressed as a GFP fused polypeptide, using an Aequorea-derived green fluorescence polypeptide GFP as a marker.

Preferably, the foreign gene is introduced by electroporation or by using the gene gun technique. Specific introduction conditions are presented in Table 2. In the present invention, the introduction of the fatty acid desaturase gene changes the fatty acid composition of the cell from that before the introduction of the fatty acid desaturase gene. Specifically, the fatty acid composition is modified by the expression of the fatty acid desaturase gene.

The stramenopiles transformation produce a stramenopiles (microorganism) in which the composition of the fatty acid it produces is modified. The stramenopiles with the fatty acid desaturase-encoding gene expressibly introduced therein can be used for, for example, the production of unsaturated fatty acids. Unsaturated fatty acid production is possible with the stramenopiles that has been modified to change its fatty acid composition as above, and other conditions, including manufacturing process, equipment, and instruments are not particularly limited. The unsaturated fatty acid production includes the step of culturing a microorganism that has been modified to change its fatty acid composition by the foregoing modification method, and the microorganism is used with a medium to produce unsaturated fatty acids.

The cell culture conditions (including medium, culture temperature, and aeration conditions) may be appropriately set according to such factors as the type of the cell, and the type and amount of the unsaturated fatty acid to be produced.

As used herein, the term "unsaturated fatty acids" encompasses substances containing unsaturated fatty acids, and attributes such as the content, purity, shape, and composition are not particularly limited. Specifically, in the present invention, the cell or medium itself having a modified fatty acid composition may be regarded as unsaturated fatty acids. Further, a step of purifying the unsaturated fatty acids from such cells or media also may be included. A known method of purifying unsaturated fatty acids and other lipids (including conjugate lipids) may be used for the purification of the unsaturated fatty acids.

[Method of Highly Accumulating Unsaturated Fatty Acid in Stramenopiles]

Accumulation of unsaturated fatty acids in stramenopiles are realized by culturing the transformed stramenopiles of the present invention. For example, the culture is performed using a common solid or liquid medium. The type of medium used is not particularly limited, as long as it is one commonly used for culturing Labyrinthulomycetes, and that contains, for example, a carbon source (such as glucose, fructose, saccharose, starch, and glycerine), a nitrogen source (such as a yeast extract, a corn steep liquor, polypeptone, sodium glutamate, urea, ammonium acetate, ammonium sulfate, ammonium nitrate, ammonium chloride, and sodium nitrate), an inorganic salt (such as potassium phosphate), and appropriately combined with other necessary components. Particularly preferably, a yeast extract/glucose agar medium (GY medium) is used. The prepared medium is adjusted to a pH of 3.0 to 8.0, and used after being sterilized with an autoclave or the like. The culture may be performed by aerated stirred culture, shake culture, or static culture at 10 to 40° C., preferably 15 to 35° C., for 1 to 14 days.

For the collection of the produced unsaturated fatty acids, the stramenopiles are grown in a medium, and the intracellular lipids (oil and fat contents with the polyunsaturated fatty acids, or the polyunsaturated fatty acids) are released by processing the microorganism cells obtained from the medium. The lipids are then collected from the medium containing the released intracellular lipids. Specifically, the cultured stramenopiles are collected by using a method such as centrifugation. The cells are then disrupted, and the intracellular fatty acids are extracted using a suitable organic solvent according to an ordinary method. Oil and fat with the enhanced polyunsaturated fatty acid content can be obtained in this manner.

In the present invention, the transformed stramenopiles with the introduced fatty acid desaturase gene are cultured, and the stramenopiles produce fatty acids of a modified composition. This is the result of the introduced fatty acid desaturase unsaturating the fatty acids normally produced in stramenopiles. The fatty acid compositional changes before and after the modification are presented and compared in Tables 8 to 10. For example, although the expression of *Pinguiochrysis*-derived Δ12 desaturase does not change the types of the fatty acids produced, the introduced enzyme affects the product ratio. Specifically, oleic acid was converted to linoleic acid, at a conversion efficiency of 30±6.6%.

In an expression test using a foreign *Labyrinthula*-derived Δ5 desaturase in a particular species of *Labyrinthula*, the EPA content showed an about 1.4-fold increase. In a culture performed in a medium containing ETA or DGLA, the ETA and DGLA were converted to EPA and AA, respectively, and the unsaturated fatty acids increased. As to the conversion efficiency in *Labyrinthula*, the conversion efficiency of a precursor substance in *Labyrinthula* was higher than that in a yeast, specifically 75% for ETA, and 63% for DGLA. These results were obtained form CG-MS test data.

The unsaturated fatty acids of the present invention encompass various drugs, foods, and industrial products, and the applicable areas of the unsaturated fatty acids are not particularly limited. Examples of the food containing oil and fat that contain the unsaturated fatty acids of the present invention include foods with health claims such as supplements, and food additives. Examples of the industrial products include feeds for non-human organisms, films, biodegradable plastics, functional fibers, lubricants, and detergents.

The present invention is described below in more detail based on examples. Note, however, that the present invention is in no way limited by the following examples.

EXAMPLE 1

Labyrinthulomycetes, Culture Method, and Preservation Method (1) Strains Used in the Present Invention

*Thraustochytrium aureum* ATCC 34304, and *Thraustochytrium* sp. ATCC 26185 were obtained from ATCC. *Aurantiochytrium limacinum* mh0186, and *Schizochytrium* sp. AL1Ac were obtained from University of Miyazaki, Faculty of Agriculture.

*Schizochytrium aggregatum* ATCC 28209, and *Ulkenia* sp. ATCC 28207 were obtained from ATCC. *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364 were obtained from Konan University, Faculty of Science and Engineering.

(2) Medium Composition
i. Agar Plate Medium Composition
PDA Agar Plate Medium

A 0.78% (w/v) potato dextrose agar medium (Nissui Pharmaceutical Co., Ltd.), 1.75% (w/v) Sea Life (Marine Tech), and a 1.21% (w/v) agar powder (nacalai tesque) were mixed, and sterilized with an autoclave at 121° C. for 20 min. After sufficient cooling, ampicillin sodium (nacalai tesque) was added in a final concentration of 100 μg/ml to prevent bacterial contamination. The medium was dispensed onto a petri dish, and allowed to stand on a flat surface to solidify.

ii. Liquid Medium Composition

GY Liquid Medium 3.18% (w/v) glucose (nacalai tesque), a 1.06% (w/v) dry yeast extract (nacalai tesque), and 1.75% (w/v) Sea Life (Marine Tech) were mixed, and sterilized with an autoclave at 121° C. for 20 min. Then, 100 μg/ml ampicillin sodium (nacalai tesque) was added.

PD Liquid Medium 0.48% (w/v) potato dextrose (Difco), and 1.75% (w/v) Sea Life (Marine Tech) were mixed, and sterilized with an autoclave at 121° C. for 20 min. Then, 100 μg/ml ampicillin sodium (nacalai tesque) was added.

H Liquid Medium 0.2% (w/v) glucose (nacalai tesque), a 0.02% (w/v) dry yeast extract (nacalai tesque), 0.05% sodium glutamate (nacalai tesque), and 1.75% (w/v) Sea Life (Marine Tech) were mixed, and sterilized with an autoclave at 121° C. for 20 min. Then, 100 μg/ml ampicillin sodium (nacalai tesque) was added.

(3) Culture Method i. Agar Plate Culture

*Labyrinthula* cells were inoculated using a platinum loop or a spreader, and static culture was performed at 25° C. to produce colonies. Subcultures were produced by collecting the colonies with a platinum loop, suspending the collected colonies in a sterilized physiological saline, and applying the suspension using a platinum loop or a spreader. As required, the cells on the plate were inoculated in a liquid medium for conversion into a liquid culture.

ii. Liquid Culture

*Labyrinthula* cells were inoculated, and suspension culture was performed by stirring at 25° C., 150 rpm in an Erlenmeyer flask or in a test tube. Subcultures were produced by adding a culture fluid to a new GY or PD liquid medium in a 1/200 to 1/10 volume after confirming proliferation from the logarithmic growth phase to the stationary phase. As required, the cell culture fluid was applied onto a PDA agar plate medium for conversion into an agar plate culture.

(4) Maintenance and Preservation Method of Labyrinthulomycetes

In addition to the subculture, cryopreservation was performed by producing a glycerol stock. Specifically, glycerol (nacalai tesque) was added in a final concentration of 15% (v/v) to the logarithmic growth phase to stationary phase of a cell suspension in a GY liquid medium, and the cells were preserved in a −80° C. deep freezer.

EXAMPLE 2

Figure 1:
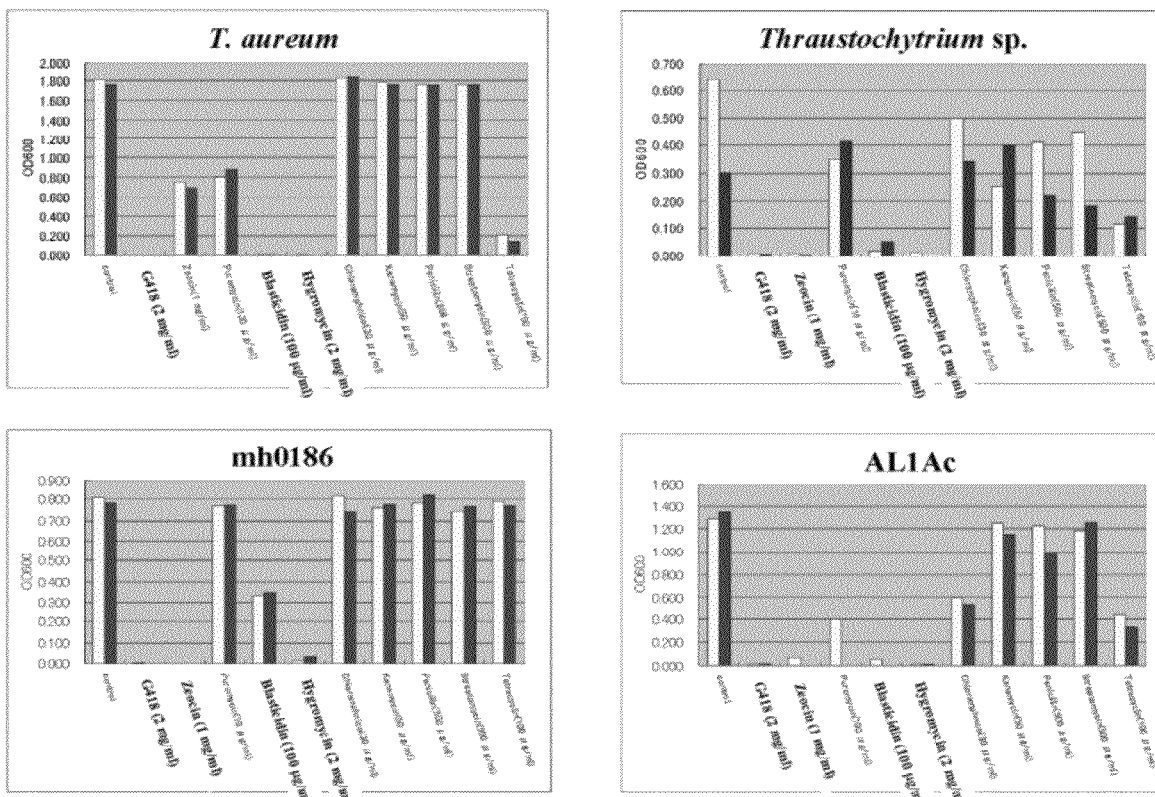
FIG. 1 represents the results of screening of antibiotics sensitivity test. The labels on the X axis are, from the left, control, G418 (2 mg/ml), Zeocin (1 mg/ml), Puromycin (100 µg/ml), Blasticidin (100 µg/ml), Hygromycin (2 mg/ml), Chloramphnicol (30 µg/ml), Kanamycin (50 µg/ml), Penicillin (500 µg/ml), Streptomycin (500 µg/ml), and Tetracyclin (100 µg/ml).

Selection of Selection Markers Used for Antibiotic Sensitivity Test and for Transformation System of Labyrinthulomycetes (1) Screening of Antibiotics Showing Sensitivity in Liquid Culture Precultures of four strains of Labyrinthulomycetes were added to GY liquid media containing various antibiotics, and cultured at 150 rpm, 25° C. for 5 days. Then, turbidity at 600 nm (OD600) was measured. FIG. 1 presents the antibiotics used and antibiotic concentrations, along with the measurement results.

Figure 2:
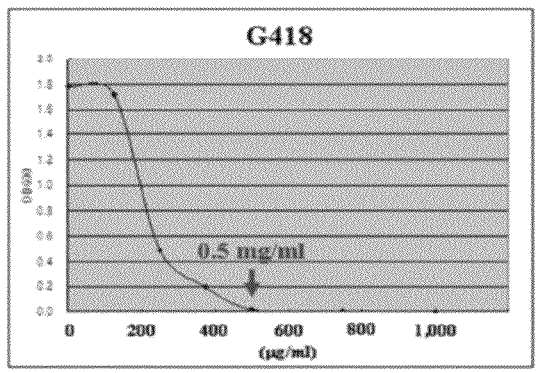
FIG. 2 represents minimal growth inhibitory concentrations in liquid cultures of *T. aureum.*
Figure 2:
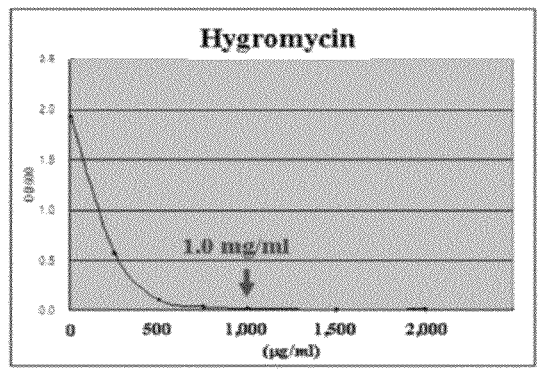
Figure 2:
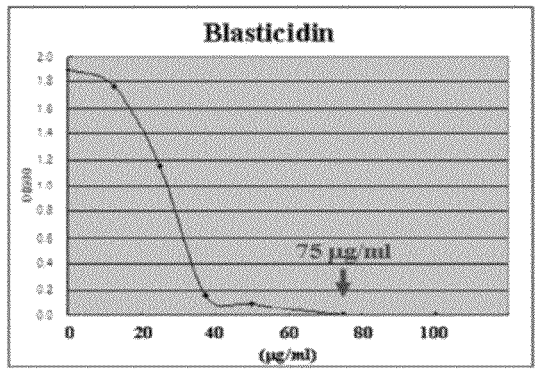
Figure 3:
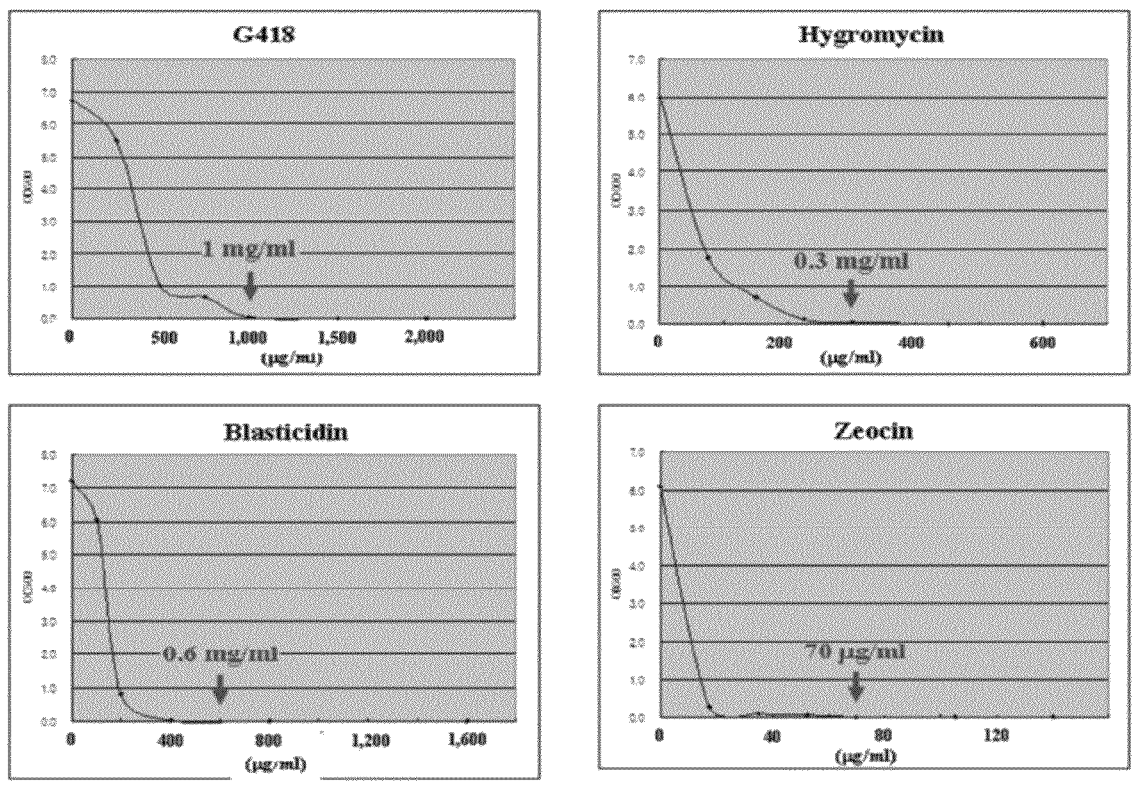
FIG. 3 represents minimal growth inhibitory concentrations in liquid cultures of *Thraustochytrium* sp.
Figure 4:
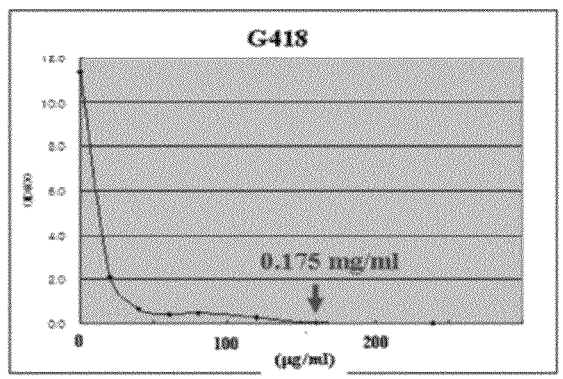
FIG. 4 represents minimal growth inhibitory concentrations in liquid cultures of mh0186.
Figure 4:
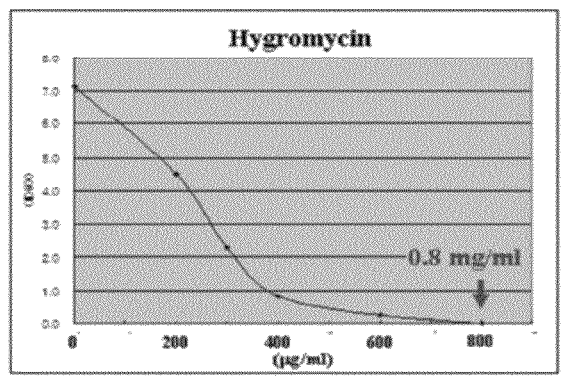
Figure 4:
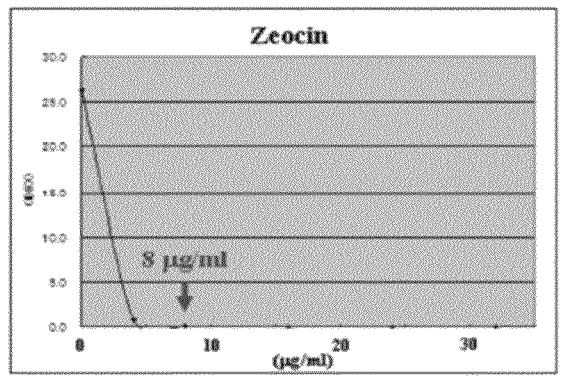
Figure 5:
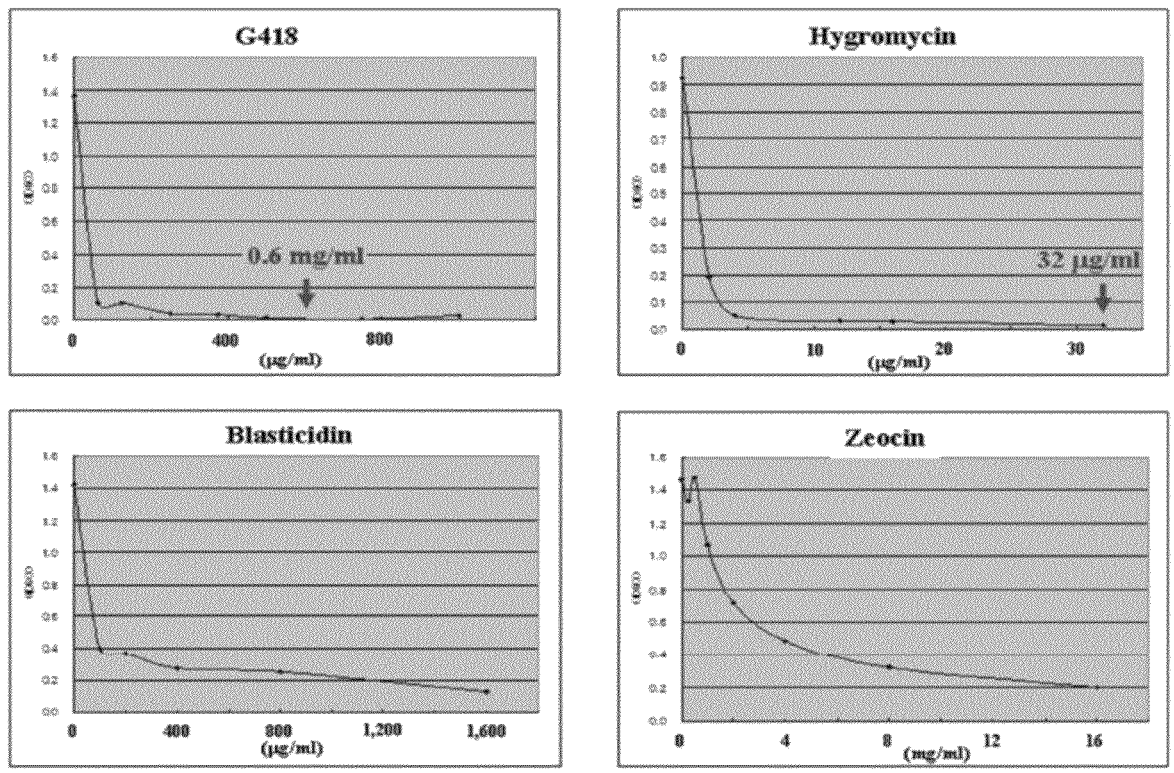
FIG. 5 represents minimal growth inhibitory concentrations in liquid cultures of AL1Ac.

(2) Determination of Minimal Growth Inhibitory Concentration (MIC) in Liquid Culture MICS in liquid culture were determined for the antibiotics that Labyrinthulomycetes showed sensitivity. Precultures of four strains of Labyrinthulomycetes were added to GY liquid media containing various antibiotics of different concentrations, and cultured at 150 rpm, 25° C. for 5 days. Then, turbidity at 600 nm ($OD_{600}$) was measured. FIG. 2 present the results for *T. aureum*, FIG. 3 present the results for *Thraustochytrium* sp. ATCC 26185, FIG. 4 present the results for *A. limacinum* mh0186, and FIG. 5 present the results for *Schizochytrium* sp. AL1Ac, respectively.

(3) Determination of MIC in Agar Plate Culture

Figure 6:
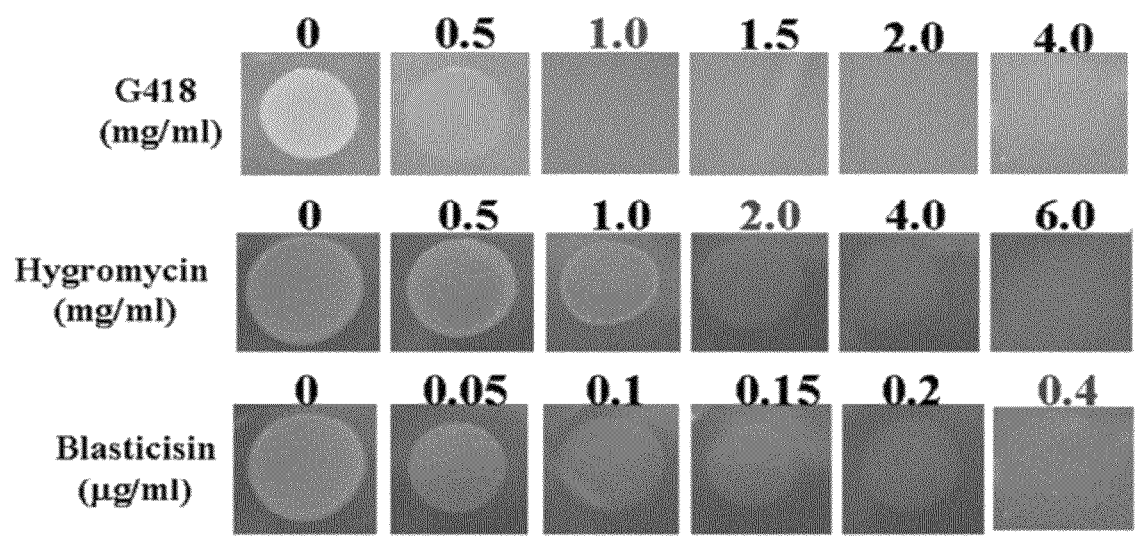
FIG. 6 represents minimal growth inhibitory concentrations in plate cultures of *T. aureum.*
Figure 7:
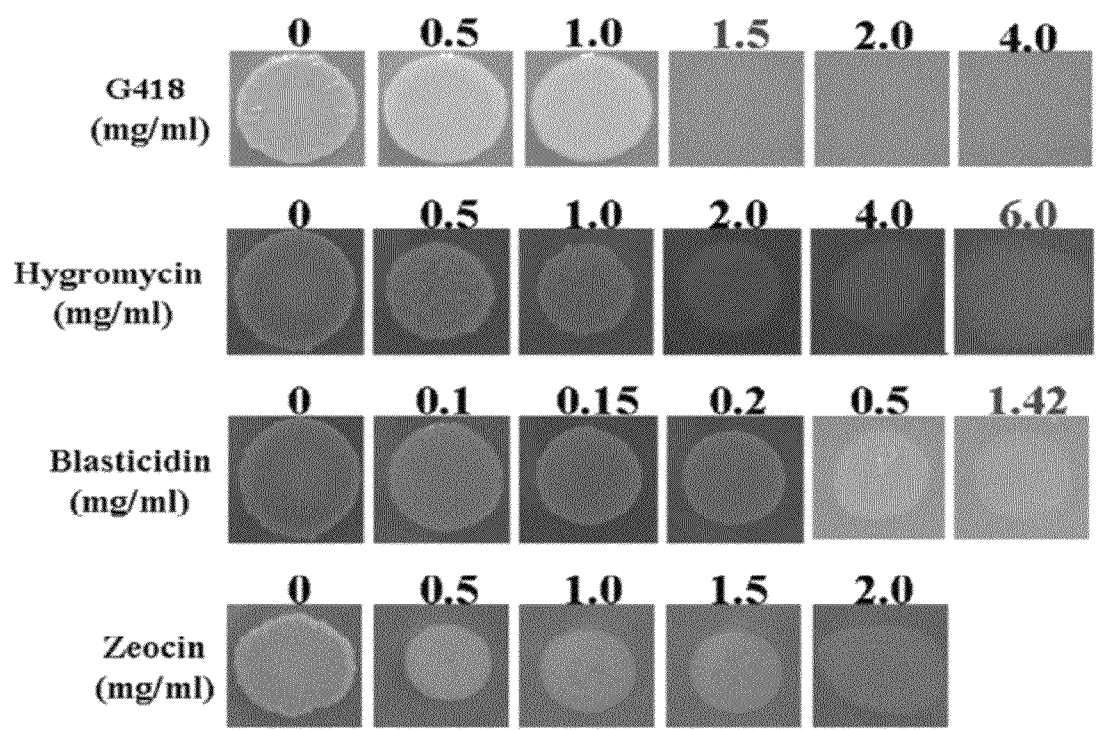
FIG. 7 represents minimal growth inhibitory concentrations in plate cultures of *Thraustochytrium* sp.
Figure 8:
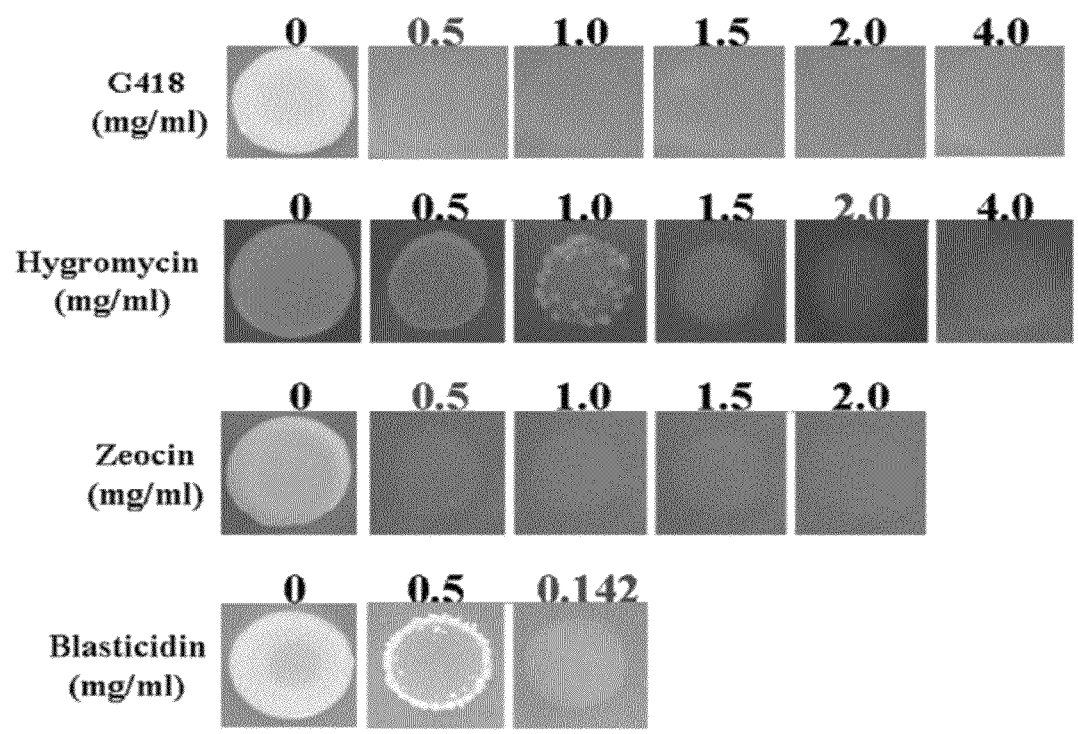
FIG. 8 represents minimal growth inhibitory concentrations in plate cultures of mh0186.
Figure 9:
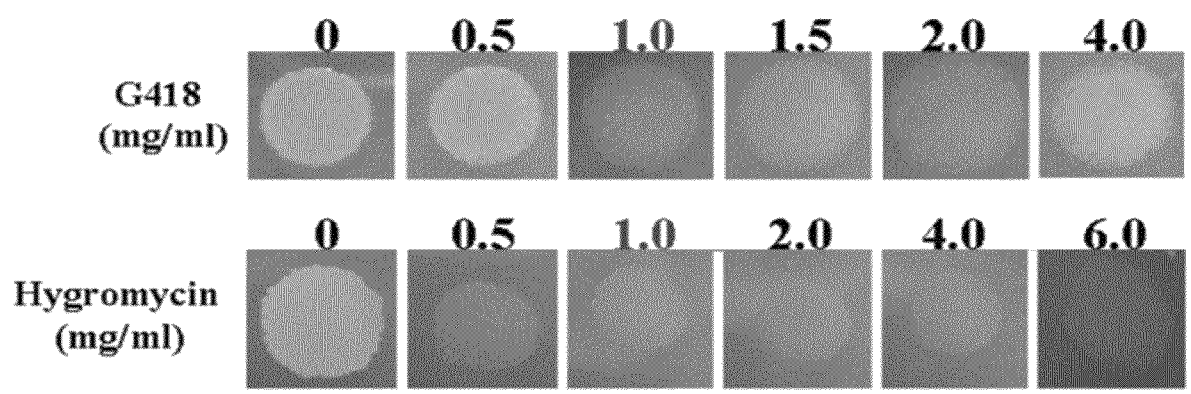
FIG. 9 represents minimal growth inhibitory concentrations in plate cultures of AL1Ac.

Precultures (5 μl) of four strains of Labyrinthulomycetes were dropped onto PDA agar media containing various antibiotics of different concentrations, and observed for colony formation after being cultured at 25° C. for 7 days. FIG. 6 present the results for *T. aureum*, FIG. 7 present the results for *Thraustochytrium* sp. ATCC 26185, FIG. 8 present the results for *A. limacinum* mh0186, and FIG. 9 present the results for *Schizochytrium* sp. AL1Ac, respectively.

In consideration of these results of the antibiotic sensitivity test and the selection marker genes used for the eukaryotes transformation system, the selection marker genes presented in the following Table 1 were found to be effective in the Labyrinthulomycetes transformation system.

TABLE 1

| Tested strain | Usable selection marker genes |
| --- | --- |
| *T. aureum* | $Neo^r$, $Hyg^r$, $Bla^r$ |
| *Thraustochytrium* sp. | $Neo^r$, $Hyg^r$, $Bla^r$, $Ble^r$ |
| *A. limacinum* mh0186 | $Neo^r$, $Hyg^r$, $Bla^r$, $Ble^r$ |
| *Schizochytrium* sp. AL1Ac | $Neo^r$, $Hyg^r$ |

$Neo^r$: Neomycin resistant gene,
$Hyg^r$: Hygromycin resistant gene
$Bla^r$: Blasticidin resistant gene,
$Ble^r$: Bleomycin resistant gene

EXAMPLE 3

Isolation of *T. aureum*-Derived EF-1α and Ubiquitin Genes, and Isolation of Gene Expression Regulatory Regions (1) Isolation of *T. aureum*-Derived EF-1α Gene and Gene Expression Region i. Isolation of *T. aureum*-Derived EF-1α Gene cDNA Sequence

*T. aureum* cells cultured in a GY liquid medium were harvested in the logarithmic growth phase to stationary phase by centrifugation at 4° C., 3,500×g for 10 min. The resulting cells were suspended in a sterilized physiological saline, and washed by recentrifugation. The cells were then ground into a powder with a mortar after rapid freezing with liquid nitrogen. Total RNA was extracted from the disrupted cell solution using a Sepasol RNA I Super (nacalai tesque), and mRNA was purified from the total RNA using an Oligotex™-dT30 <Super> mRNA Purification Kit (Takara Bio).

Thereafter, a cDNA library including a synthetic adapter added to the 5'- and 3'-ends was produced using a SMART™ RACE cDNA Amplification Kit (clontech). A single forward degenerate oligonucleotide primer EF-F1 (SEQ ID NO: 1 in the Sequence Listing) was produced based on a known EF-1α conserved sequence using a DNA synthesizer (Applied Biosystems). 3' RACE performed with these materials confirmed a specific amplification product. The DNA fragments isolated by electrophoresis on a 1% agarose gel were cut out with, for example, a clean cutter, and the DNA was extracted from the agarose gel according to the method described in Non-Patent Document 10. This was followed by the TA cloning of the DNA fragments using a pGEMR-T easy Vector System I (Promega), and the base sequences of these fragments were determined according to the method of Sanger et al. (Non-Patent Document 11). Specifically, the base sequences were determined by the dieterminator technique using a BigDyeR Terminator v3.1 Cyele Sequencing Kit, and a 3130 genetic analyzer (Applied Biosystems). The result that the resulting 980-bp 3' RACE product (SEQ ID NO: 2 in the Sequence Listing) was highly homologous to the EF-1α genes derived from other organisms strongly suggested that the product was a partial sequence of the *T. aureum*-derived EF-1α gene.

From this sequence, two reverse oligonucleotide primers EF-1r (SEQ ID NO: 3 in the Sequence Listing) and EF-2r (SEQ ID NO: 4 in the Sequence Listing) were produced, and 5' RACE was performed using these primers. The result confirmed 5' RACE products specific to the both. A base sequence analysis found that the former was a 496-bp partial sequence (SEQ ID NO: 5 in the Sequence Listing) of the *T. aureum*-derived putative EF-1α gene, and the latter a 436-bp (SEQ ID NO: 6 in the Sequence Listing) partial sequence of the *T. aureum*-derived putative EF-1α gene. There was a complete match with the 3' RACE product in the overlapping portions.

It was found from these results that the cDNA sequence of the *T. aureum*-derived putative EF-1α gene was a 1,396-bp sequence (SEQ ID NO: 7 in the Sequence Listing), and that the ORF region was a 1,023-bp region (SEQ ID NO: 9 in the Sequence Listing) encoding 341 amino acid residues (SEQ ID NO: 8 in the Sequence Listing).

ii. Isolation of *T. aureum*-Derived EF-1α Gene Regulatory Region

*T. aureum* cells cultured in GY medium were harvested by centrifugation. The resulting cells were suspended in a sterilized physiological saline, and washed by recentrifugation. The cells were then ground into a powder with a mortar after rapid freezing with liquid nitrogen. The genomic DNA was extracted according to the method described in Non-Patent Document 12, and A260/280 was taken to measure the purity and concentration of the extracted genomic DNA.

This was followed by PCR genome walking to isolate the EF-1α gene ORF upstream sequence (promoter) or ORF downstream sequence (terminator), using an LA PCR in vitro Cloning Kit. Note that a reverse oligonucleotide primer r3 (SEQ ID NO: 10 in the Sequence Listing) was used for the amplification of the ORF upstream sequence, and forward oligonucleotide primers EF-t-F1 (SEQ ID NO: 11 in the Sequence Listing) and EF-t-F2 (SEQ ID NO: 12 in the Sequence Listing) were used for the amplification of the ORF downstream sequence. Analysis of the base sequences of the resulting specific amplification products revealed successful isolation of a 615-bp ORF upstream sequence (SEQ ID NO: 13 in the Sequence Listing), and a 1, 414-bp ORF downstream sequence (SEQ ID NO: 14 in the Sequence Listing) of the *T. aureum*-derived EF-1α gene. In the following, the former is denoted as EF-1α promoter, and the latter EF-1α terminator.

(2) Isolation of *T. aureum*-Derived Ubiquitin Gene and Gene Expression Region i. Isolation of *T. aureum*-Derived Ubiquitin Gene cDNA Sequence 3' RACE was performed with a forward degenerate oligonucleotide primer 2F (SEQ ID NO: 15 in the Sequence Listing) produced from a known ubiquitin gene conserved sequence, using the cDNA library created by using a SMART™ RACE cDNA Amplification Kit (clontech) as a template. Analysis of the base sequence of the resulting amplification product revealed that the product was a 278-bp partial sequence (SEQ ID NO: 16 in the Sequence Listing) of the *T. aureum*-derived putative ubiquitin gene. Specific amplification products could not be obtained in 5' RACE, despite use of various oligonucleotide primers under different PCR conditions. This raised the possibility that the high GC-content higher-order structure of the target mRNA might have inhibited the reverse transcription reaction in the cDNA library production.

5' RACE was thus performed using a 5' RACE System for Rapid Amplification of cDNA Ends, Version 2.0 (Invitrogen), which uses a reverse transcriptase having high heat stability. Note that reverse oligonucleotide primer 1R (SEQ ID NO: 17 in the Sequence Listing) was used for the reverse transcription reaction, and reverse nucleotide primer 2R (SEQ ID NO: 18 in the Sequence Listing) was used for the PCR reaction after the cDNA synthesis. Analysis of the base sequence of the resulting amplification product revealed that the product was a 260-bp partial sequence (SEQ ID NO: 19 in the Sequence Listing) of the *T. aureum*-derived putative ubiquitin gene, and there was a complete match with the 3' RACE product in the overlapping portion. The result thus revealed successful isolation of the *T. aureum*-derived putative ubiquitin gene cDNA sequence.

However, it is known that the ubiquitin gene typically has a repeat structure of the same sequence. It is thus speculated the result did not represent the full-length structure of the gene, but rather revealed the 5'- and 3'-end noncoding regions, and the single sequence forming the repeat structure in the ORF region. Note that the single sequence found in the ORF region of the *T. aureum*-derived putative ubiquitin gene was found to be a 228-bp sequence (SEQ ID NO: 21 in the Sequence Listing) encoding 76 amino acid residues (SEQ ID NO: 20 in the Sequence Listing).

ii. Isolation of *T. aureum*-Derived Ubiquitin Gene Regulatory Region

PCR genome walking was performed to isolate a ubiquitin gene ORF upstream sequence (promoter) or an ORF downstream sequence (terminator), using an LA PCR in vitro Cloning Kit. Note that reverse oligonucleotide primers REVERS-U PR-1 (SEQ ID NO: 22 in the Sequence Listing) and REVERS-U PR-2 (SEQ ID NO: 23 in the Sequence Listing) were used for the amplification of the ORF upstream sequence, and forward oligonucleotide primers ubqterminalf1 (SEQ ID NO: 24 in the Sequence Listing) and ter2F (SEQ ID NO: 25 in the Sequence Listing) were used for the amplification of the ORF downstream sequence. Analysis of the base sequences of the specific amplification products revealed successful isolation of a 801-bp ORF upstream sequence (SEQ ID NO: 26 in the Sequence Listing), and a 584-bp ORF downstream sequence (SEQ ID NO: 27 in the Sequence Listing) of the *T. aureum*-derived ubiquitin gene. In the following, the former will be denoted as ubiquitin promoter, and the latter ubiquitin terminator.

In this manner, the promoters and terminators of the *T. aureum*-derived house keeping gene EF-1α and the ubiquitin gene were successfully isolated as the gene expression regulatory regions that constantly function in Labyrinthulomycetes.

EXAMPLE 4

Production of Drug-Resistant Gene Expression Cassette (1) Artificial Synthesis of Neomycin-Resistant Gene (Neo^r)

Artificial Neo^r was synthesized by MediBic according to the codon usage of *T. aureum* in codon usage database (www.kazusa.or.jp/codon/). The base sequence is represented by SEQ ID NO: 28 in the Sequence Listing, and the encoded amino acid sequence by SEQ ID NO: 29 of the Sequence Listing.

(2) Construction of Neo$^r$ Expression Cassette i. Construction of Neo$^r$ Expression Cassette Using EF-1α Promoter and Terminator A DNA fragment including *T. aureum*-derived 18S rDNA joined by fusion PCR to the upstream side of a drug-resistant gene (Neo$^r$) expression cassette including EF-1α promoter/ artificial Neo$^r$/EF-1α terminator was produced by using the oligonucleotide primers represented by SEQ ID NOS: 30 to 38 of the Sequence Listing, according to the method described in Nippon Nogeikagaku Kaishi, Vol. 77, No. 2 (February, 2003), p. 150-153. PCR reaction was run at a denature temperature of 98° C. for 10 seconds, and the annealing and extension reactions were appropriately adjusted according to the Tm of the primers, and the length of the amplification product.

Figure 10:
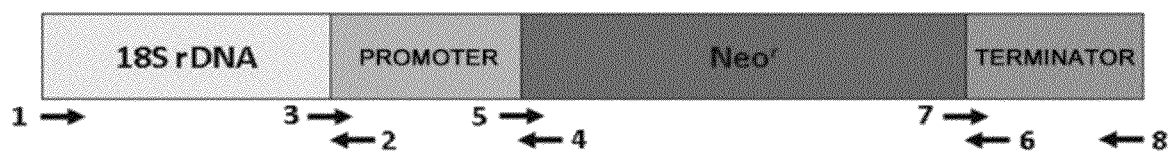
FIG. 10 is a schematic view representing a drug-resistant gene cassette (EF-1α promoter, terminator). Reference numerals: 1. 18S 2. 1R 3. 2F 4. neo-pro-3F 5. n-G-pro-3F 6. n-term-G-4R 7. n-term-G-4F 8. terminator 5R

As a result, *T. aureum* 18S rDNA, EF-1α promoter, artificial Neo$^r$, and EF-1α terminator were successfully joined (4,454 bp; SEQ ID NO: 39 in the Sequence Listing; FIG. 10).

Figure 11:
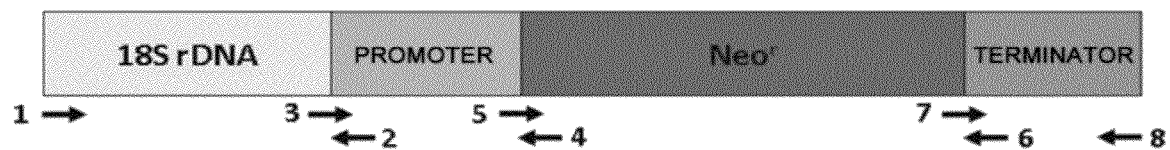
FIG. 11 is a schematic view representing a drug-resistant gene cassette (ubiquitin promoter, terminator). Reference numerals: 1. Ndel18SF 2. 18s-fug-ubq-R 3. Ubpro-HindIII-R 4. UbproG418fus1R 5. ubproG418fus2F 6. G418ubtersus3R 7. G418ubterfus4F 8. KpnIterR.
Figure 12:
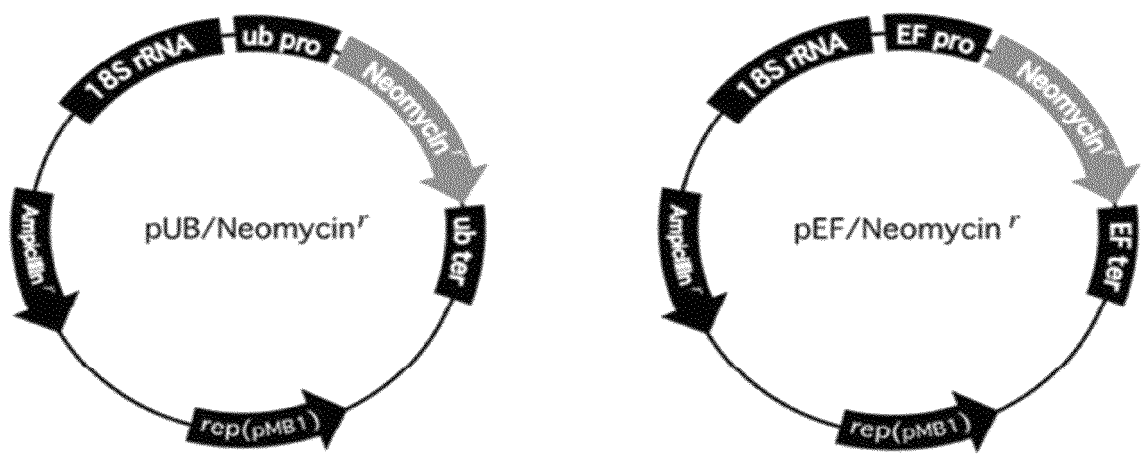
FIG. 12 represents constructed *Labyrinthula-Escherichia coli* shuttle vectors.

By TA cloning using a pGEM-T easy (Invitrogen), a *Labyrinthula-Escherichia coli* shuttle vector was constructed that included a Neo$^r$ expression cassette with the EF-1α promoter and terminator used as the selection marker for *Labyrinthula*, and the *T. aureum*-derived 18S rDNA sequence as a homologous recombination site. In the following, this will be denoted as pEFNeomycin$^r$ (FIG. 12).

ii. Construction of Neo$^r$ Expression Cassette Using Ubiquitin Promoter and Terminator The same technique used for the Neo$^r$ expression cassette using the EF-1α promoter and terminator was used to join *T. aureum* 18S rDNA, ubiquitin promoter, artificial Neo$^r$, and ubiquitin terminator, using the oligonucleotide primers represented by SEQ ID NOS: 40 to 47 of the Sequence Listing (FIG. 11). The constructed Neo$^r$ expression cassette was incorporated by using the NdeI/KpnI site of a pUC18 vector, and a *Labyrinthula-Escherichia coli* shuttle vector was constructed that included a Neo$^r$ expression cassette with the ubiquitin promoter and terminator used as the selection marker for *Labyrinthula*, and the *T. aureum*-derived 18S rDNA sequence as a homologous recombination site. In the following, this will be denoted as pUBNeomycin$^r$ (FIG. 12).

In this manner, two vectors were constructed: The *Labyrinthula-Escherichia coli* shuttle vector pEFNeomycin$^r$ including the Neo$^r$ expression cassette with the EF-1α gene promoter and terminator used as the selection marker for *Labyrinthula*; and the pUBNeomycin$^r$ including the Neo$^r$ expression cassette with the ubiquitin gene promoter and terminator. For easy Neo$^r$ expression in *Labyrinthula*, these vectors use the artificially synthesized Neo$^r$ whose codons have been optimized by using the *T. aureum* codon usage as reference. Further, the vectors include the *T. aureum*-derived 18S rDNA sequence, taking into consideration incorporation into chromosomal DNA by homologous recombination (FIGS. 10 and 11).

EXAMPLE 5

Gene Introduction Experiment Using *Labyrinthula*

(1) DNAs Used in Gene Introduction Experiment

Gene introduction experiment was conducted using the following four DNAs.
(1) Cyclic vector pUBNeomycin$^r$
(2) Cyclic vector pEFNeomycin$^r$
(3) Linear Neo$^r$ expression cassette adopting ubiquitin promoter and terminator (ub-Neo$^r$)
(4) Linear Neo$^r$ expression cassette adopting EF-1α promoter and terminator (EF-Neo$^r$)

For (3), PCR was performed with an oligonucleotide primer set Ubpro-fug-18s-F (SEQ ID NO: 42 in the Sequence Listing)/KpnterR (SEQ ID NO: 47 in the Sequence Listing), using an LA taq Hot Start Version (Takara Bio), and pUB-Neomycin$^r$ as a template, and the resulting amplification product was gel purified. For (4), PCR was performed with an oligonucleotide primer set 2F (SEQ ID NO: 32 in the Sequence Listing)/terminator 5R (SEQ ID NO: 33 in the Sequence Listing), using an LA taq Hot Start Version (Takara Bio), and pEFNeomycin$^r$ as a template, and the resulting amplification product was gel purified.

(2) Gene Introducing Technique Used for Gene Introduction Experiment i. Electroporation Labyrinthulomycetes were cultured in a GY liquid medium to the middle to late stage of the logarithmic growth phase at 25° C., 150 rpm, and the supernatant was removed by centrifugation at 3,500×g, 4° C. for 10 min. The resulting cells were suspended in sterilized 1.75% Sea Life (Marine Tech), and washed by recentrifugation. The cells (5×10$^6$) were then suspended in 50 mM sucrose, or in a reagent for gene introduction attached to the equipment used. After applying electrical pulses in different settings, GY liquid medium (1 ml) was immediately added, and the cells were cultured at 25° C. for 12 hours. The culture fluid was then applied to a PDA agar plate medium containing 2 mg/ml G418 (*T. aureum, Thraustochytrium* sp. ATCC 26185, *Schizocytrium* sp. AL1Ac) or 0.5 mg/ml G418 (*A. limacinum* mh0186). After static culturing at 25° C., colony formation of transfectants with the conferred G418 resistance was observed.

ii. Gene Gun Technique

Labyrinthulomycetes were cultured in a GY liquid medium to the middle to late stage of the logarithmic growth phase at 25° C., 150 rpm, and the supernatant was removed by centrifugation at 3,500×g, 4° C. for 10 min. The resulting cells were resuspended in a GY liquid medium in 100 times the concentration of the original culture fluid, and a 20-μl portion of the cell suspension was evenly applied as a thin layer of about a 3-cm diameter on a 5-cm diameter PDA agar plate medium containing or not containing G418. After drying, DNA penetration was performed by using the gene gun technique, using a PDS-1000/He system (Bio-Rad Laboratories). The penetration conditions were investigated by varying the penetration pressure, as follows.

target distance: 6 cm (fixed)
   vacuum: 26 inches Hg (fixed)
   micro carrier size: 0.6 μm (fixed)
   Rupture disk (penetration pressure): 450, 900, 1100, 1350, and 1,550

In the case of the G418-containing PDA agar plate medium, the cells after the penetration were statically cultured for about 12 hours from the introduction. The static culture was continued after spreading the cells with 100 μl of PDA liquid medium on the PDA agar plate. On the other hand, in the PDA agar plate medium containing no G418, the cells after the penetration were statically cultured for about 12 hours from the introduction, collected, and reapplied to a PDA agar plate medium containing 2 mg/ml or 0.5 mg/ml G418. After static culturing at 25° C., colony formation of transfectants with the conferred G418 resistance was observed.

(3) Acquisition and Evaluation of Transfectant i. *A. limacinum* Transfectant

Gene introduction was performed by electroporation under the following conditions
- introduced DNA: pUBNeomycin$^r$ and ub-Neo$^r$
- gene introducing technique: electroporation
- cell suspension buffer: 50 mM sucrose
- gene introducing apparatus: Gene Pulser (Bio-Rad Laboratories) with a 1-mm gap cuvette
- pulse settings: 50 μF/50 Ω/0.75 kV, single application In samples using the linear DNA ub-Neo$^r$, G418-resistant colonies were observed at the efficiency as high as $2.4 \times 10^0$ cfu/μq DNA. On the other hand, in samples using the cyclic DNA pUBNeomycin$^r$, no colony formation was observed, regardless of multiple introductions.

A comparative examination of introduction efficiency was made using a gene introducing apparatus. Introduction tests were conducted using a Microporator MP-100 (AR Brown) or a Nucleofector™ (amaxa) with the attached condition search kit. While no single colony was formed with the Microporator MP-100, the Nucleofector used with the attached cell suspension buffer Nucleofector R solution L produced transfectants with good reproducibility at the efficiency as high as $9.5 \times 10^0$ cfu/μg DNA.

Then, pulse settings were examined with the NucleofectorR solution L, using a Gene Pulser (Bio-Rad Laboratories). It was found as a result that transfectants could be obtained with good reproducibility at the efficiency as high as $1.2 \times 10^1$ cfu/μg DNA by double application under the following conditions: capacitance 50 μF, electrical resistance 50Ω, and electric field intensity 0.75 kV. The results are summarized in Table 2 below.

TABLE 2

| Gene introducing apparatus | Introduction reagent (cell suspension buffer) | Pulse settings | Gene introduction efficiency |
|---|---|---|---|
| Gene Pulser | 50 mM sucrose | 50 μF/50 Ω/0.75 kV, single application | up to $2.4 \times 10^0$ cfu/μg DNA |
| Microporator MP-100 | Attached buffer | Conditions specified in the manual | — |
| Nucleofector ™ | Attached buffer (Necleofector ® solution L) | Conditions specified in the manual | up to $9.5 \times 10^0$ cfu/μg DNA |
| Gene Pulser | Necleofector ® solution L | 50 μF/50 Ω/0.75 kV, double application | up to $1.2 \times 10^1$ cfu/μg DNA | ii. Evaluation of *A. limacinum* Transfectant Using G418-Resistance as Index

Figure 13:
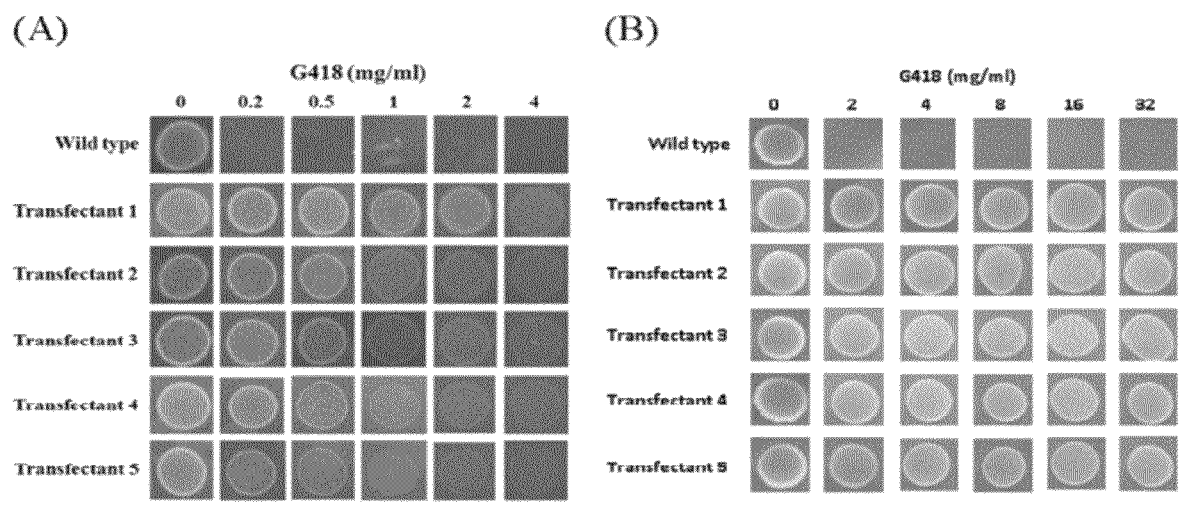
FIG. 13 represents evaluations of *A. limacinum* transfectants using G418 resistance as an index.

The transfectants were cultured in 0.5 mg/ml G418-containing GY liquid medium. The wild-type strain was cultured in GY liquid medium containing no G418. The culture fluids of these strains were spotted in 10-μl portions on PDA agar plate media containing G418 (0, 0.2, 0.5, 1, 2, 4 mg/ml), and growth on the agar plate media was observed after culturing the cells at 25° C. for 2 days. It was found as a result that the proliferation was inhibited at 0.2 mg/ml G418 in the wild-type strain, whereas the transfectants proliferated even in the presence of 4 mg/ml G418 (FIG. 13A). Further, there was no change in G418 resistance, and proliferation was observed even at a G418 concentration of 32 mg/ml in a similar experiment conducted with PDA agar plate media containing G418 (0, 2, 4, 8, 16, 32 mg/ml) after subculturing the transfectants five times in a GY liquid medium containing no G418 (FIG. 13B). These results using the G418 resistance as an index confirmed that the conferred character was stable.

iii. Morphology Comparison of *A. limacinum* Transfectant and Wild-Type Strain

Figure 14:
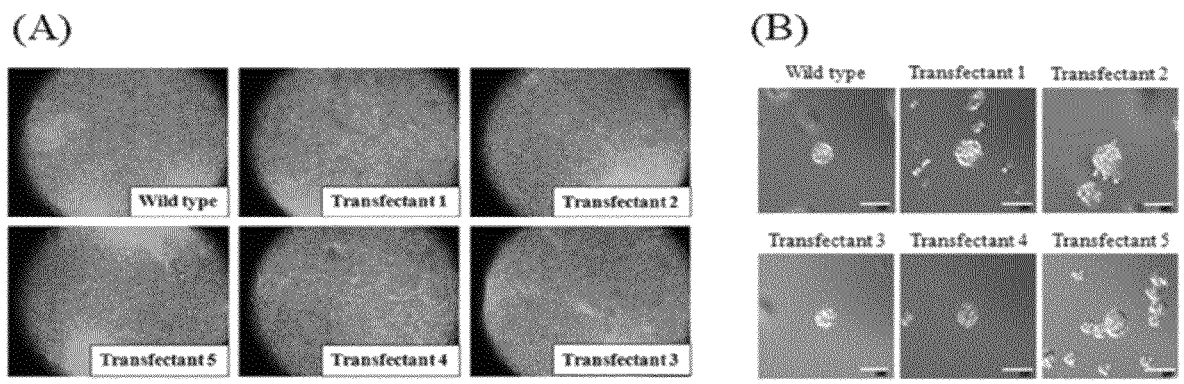
FIG. 14 represents morphological comparisons between *A. limacinum* transfectants and a wild-type strain.

It was confirmed by microscopy (FIG. 14A) and by confocal laser microscope observation after staining the oil globules in the cells with nile red (FIG. 14B) that there was no morphological change between the wild-type strain and the transfectants. Further, 18S rDNA analysis confirmed that the transfectants were *A. limacinum*.

iv. Evaluation of *A. limacinum* Transfectant by PCR Using Genomic DNA as Template The transfectants were cultured in 0.5 mg/ml G418-containing GY liquid medium. The wild-type strain was cultured in GY liquid medium containing no G418. Genomic DNA was extracted from the cells of each strain by using an ISOPLANT (nacalai tesque). Using the genomic DNA as a template, Neo$^r$ was amplified by PCR using an LA taq Hot Start Version (Takara Bio). The oligonucleotide primers ubproG418fus2F (SEQ ID NO: 45 in the Sequence Listing)/G418ubtersus3R (SEQ ID NO: 46 in the Sequence Listing) were used (PCR cycles: 94° C. 2 min/98° C. 10 sec, 68° C. 1 min, 72° C., 30 cycles/4° C.).

Figure 15:
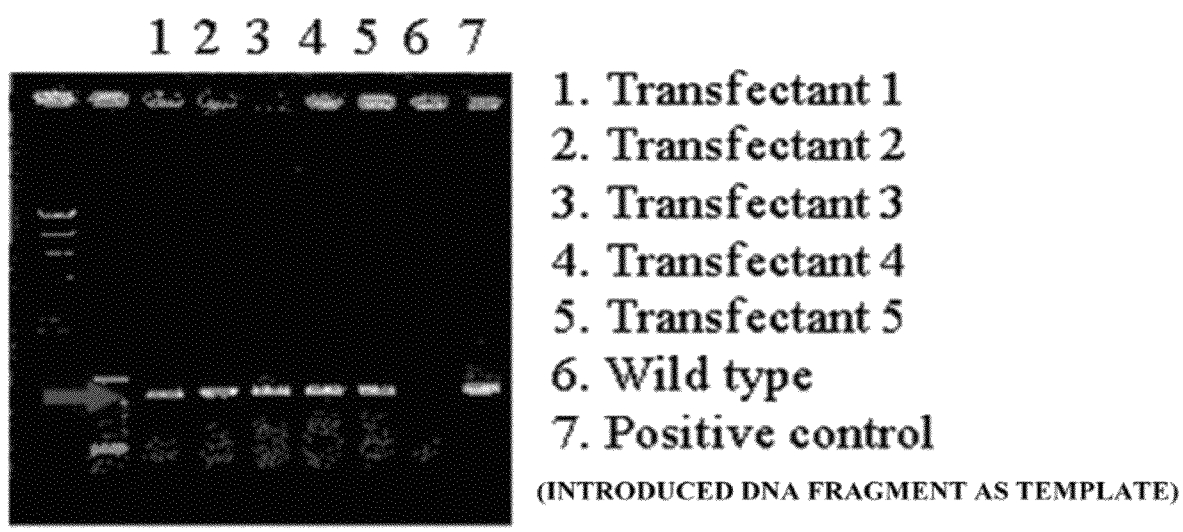
FIG. 15 represents evaluations of *A. limacinum* transfectants by PCR using genomic DNA as a template. Reference numerals: 1: Transfectant 1 2: Transfectant 2 3: Transfectant 3 4: Transfectant 4 5: Transfectant 5 6: Wild type 7: Positive control (introduced DNA fragment was used as a template).

As a result, specific Neo$^r$ amplification, not found in the wild-type strain, was observed in the transfectants (FIG. 15). The result thus suggested that the introduced ub-Neo$^r$ was incorporated in the chromosomal DNA.

v. Evaluation of *A. limacinum* Transfectant by Southern Blotting

Genomic DNAs (2 μg) of the *A. limacinum* transfectants and the wild-type strain extracted according to an ordinary method were digested with various restriction enzymes at 37° C. for 16 hours, and Southern blotting was performed according to the DIG Manual, 8th, Roche, using a DIG-labeled Neo$^r$ as a probe.

Figure 16:
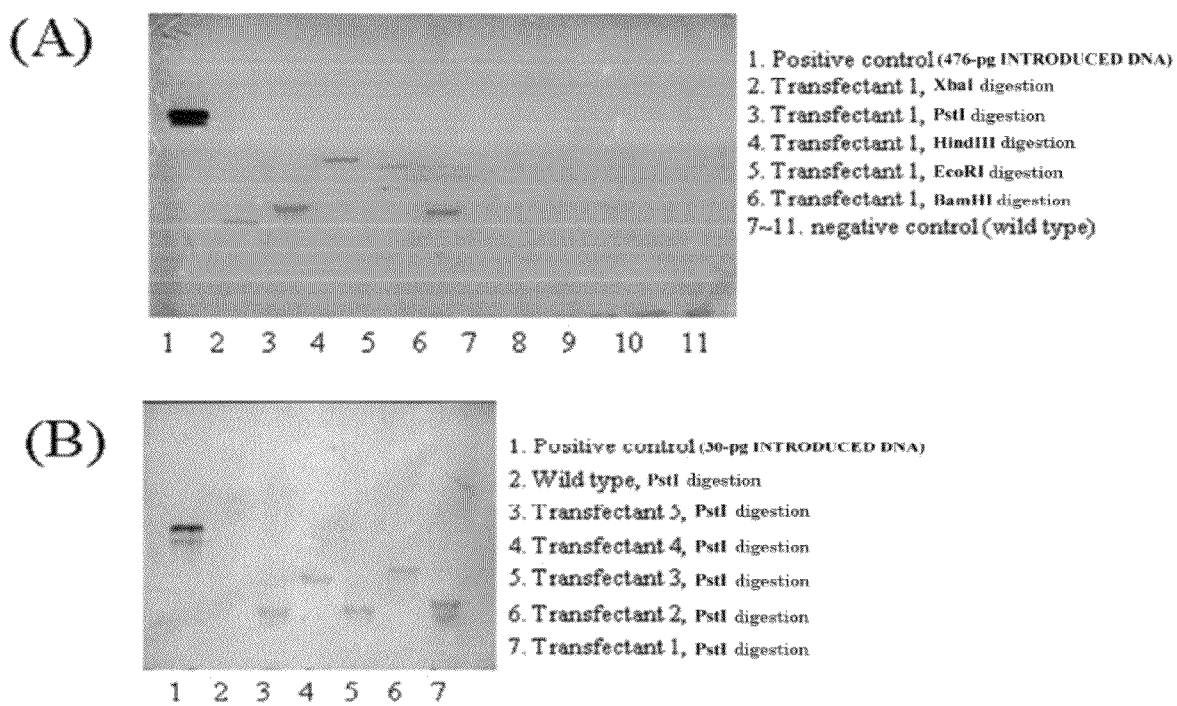
FIG. 16 represents evaluations of *A. limacinum* transfectants by Southern blotting. Reference numerals: (A) 1. Positive control (476-pg introduced DNA) 2. Transfectant 1, XbaIdigestion 3. Transfectant 1, PstI treatment 4. Transfectant 1, HindIII treatment 5. Transfectant 1, EcoRI treatment 6. Transfectant 1, BamHI treatment 7 to 11. negative control (wild type) (B) 1. Positive control (30-pg introduced DNA) 2. Wild type, PstI treatment 3. Transfectant 5, PstI treatment 4. Transfectant 4, PstI treatment 5. Transfectant 3, PstI treatment 6. Transfectant 2, PstI treatment 7. Transfectant 1, PstI treatment.

As a result, a Neo$^r$ band was detected, as shown in FIG. 16A. This suggested that the ub-Neo$^r$ by the introduced ubiquitin promoter and terminator had been incorporated in the chromosomal DNA. Further, the result that the five transfectant bands digested with the same enzyme (PstI) had different molecular weights suggested that the introduced DNA fragment was randomly incorporated in the chromosomal DNA (FIG. 16B).

vi. Evaluation of *A. limacinum* Transfectant by RT-PCR

Total RNA was extracted from the cells of the *A. limacinum* transfectants and the wild-type strain using a Sepasol RNA I super (nacalai tesque). After cleaning the total RNA using an RNeasy plus mini kit (QIAGEN), a reaction was run at 37° C. for 1 hour by using a Cloned DNase I (Takara Bio) according to the attached manual to degrade the contaminated genomic DNA. This was followed by a reverse transcription reaction using a PrimeScript Reverse Transcriptase (Takara Bio) to synthesize cDNA by reverse transcription reaction. The cDNA was used as a template to amplify Neo$^r$ by PCR using an LA taq Hot Start Version (Takara Bio). The oligonucleotide primers ubproG418fus2F (SEQ ID NO: 45 in the Sequence Listing)/G418ubtersus3R (SEQ ID NO: 46 in the Sequence Listing) were used (PCR cycles: 94° C. 2 min/98° C. 10 sec, 68° C. 1 min, 72° C., 30 cycles/4° C.).

Figure 17:
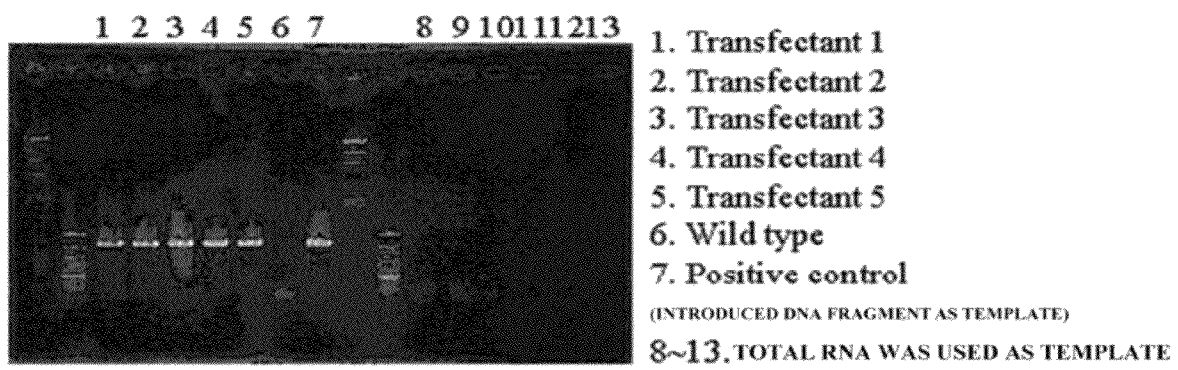
FIG. 17 represents evaluations of *A. limacinum* transfectants by RT-PCR. Reference numerals: 1: Transfectant 1 2: Transfectant 2 3: Transfectant 3 4: Transfectant 4 5: Transfectant 5 6: Wild type 7: Positive control (introduced DNA fragment was used as a template); 8 to 13: Total RNA was used as a template.

As a result, Neo$^r$ amplification products were confirmed in the transfectants (FIG. 17, lanes 1 to 5). The result that amplification products were not observed in a PCR using the total RNA as a template (FIG. 17, lanes 8 to 13) suggested that the products observed in lanes 1 to 5 were not genomic DNA contamination, but originated in the Neo$^r$ mRNA reverse transcripts (Neo$^r$ cDNA). It was therefore found that the ub-Neo$^r$ incorporated in the chromosomal DNA was subject to transcription into mRNA.

vii. Acquisition of *T. aureum* Transfectant

Two types of DNAs, pUBNeomycin$^r$ and ub-Neo$^r$, were used as the introduced DNAs. After investigating various conditions, it was found that no transfectants could be obtained by electroporation. With the gene gun technique, however, it was possible to acquire transfectants with the conferred G418 resistance. The gene introduction efficiency was the highest at a penetration pressure of 1,100 psi, specifically as high as $1.9 \times 10^2$ cfu/µg DNA in the case of ub-Neo$^r$. The gene introduction efficiency was as high as $1.4 \times 10^1$ cfu/µg DNA for the pUBNeomycin$^r$, showing that the introduction efficiency was about 14 times higher in the random integration introducing the liner DNA than in the introduction of the cyclic DNA using the 18S rDNA sequence as a homologous recombination site. It was also found that the transfectants maintained the G418 resistance even after being subcultured five times in a GY liquid medium containing no G418.

viii. Morphology Comparison of *T. aureum* Transfectant and Wild-Type Strain

Figure 18:
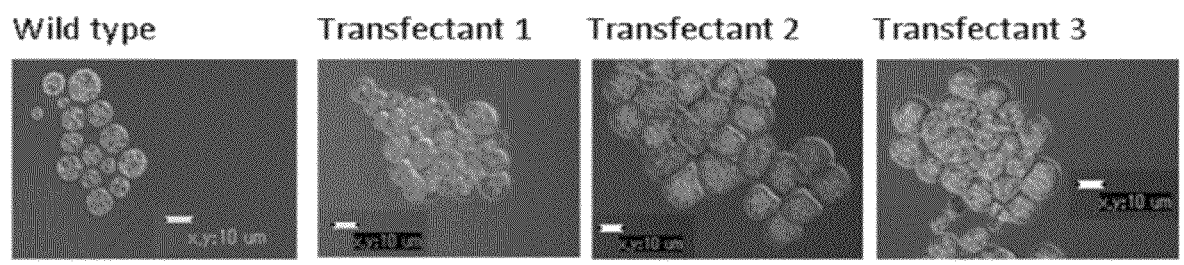
FIG. 18 represents morphological comparisons between *T. aureum* transfectants and a wild-type strain.
Figure 19:
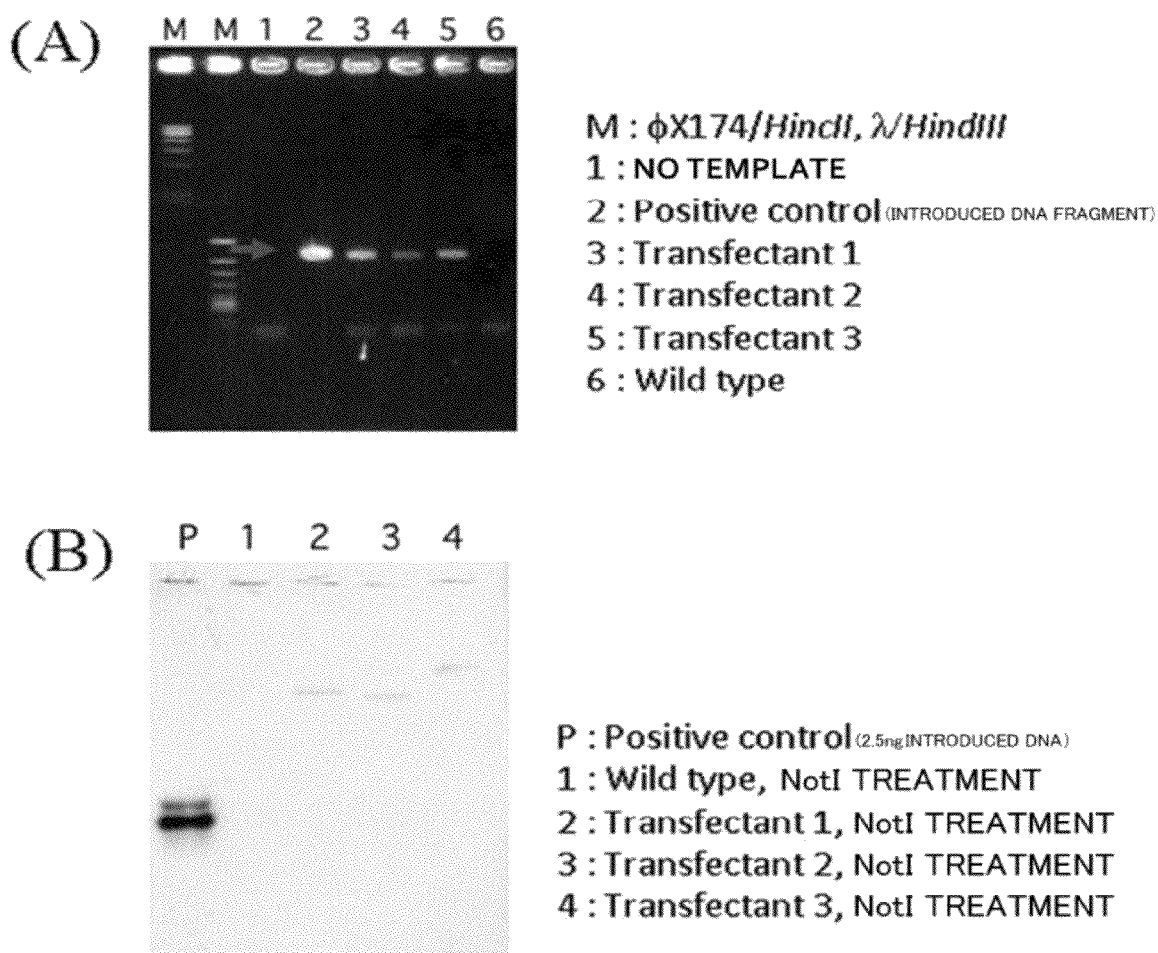
FIG. 19 represents evaluations of *T. aureum* transfectants by PCR using genomic DNA as a template, and by Southern blotting. Reference numerals: (A) M : φX174/HincII, λ HindIII 1: No template 2: Positive control (introduced DNA fragment) 3: Transfectant 1 4: Transfectant 2 5: Transfectant 3 6: Wild type (B) P: Positive control (introduced DNA, 2.5 ng) 1: Wild type, NotI treatment 2: Transfectant 1, NotI treatment 3: Transfectant 2, NotI treatment 4: Transfectant 3, NotI treatment.

Confocal laser microscope observation after staining the oil globules of the cells with nile red (FIG. 18) confirmed no morphological change between the wild-type strain and the transfectants. Further, 18S rDNA analysis confirmed that the transfectants were *T. aureum*.

ix. Evaluation of *T. aureum* Transfectant by PCR Using Genomic DNA as Template and by Southern Blotting As with the case of the *A. limacinum* transfectants, random incorporation of ub-Neo$^r$ in the chromosomal DNA was confirmed by PCR using the genomic DNA as a template (FIG. 19A), and by Southern blotting detecting Neo$^r$ (FIG. 19B).

x. Evaluation of *T. aureum* Transfectant by RT-PCR

Figure 20:
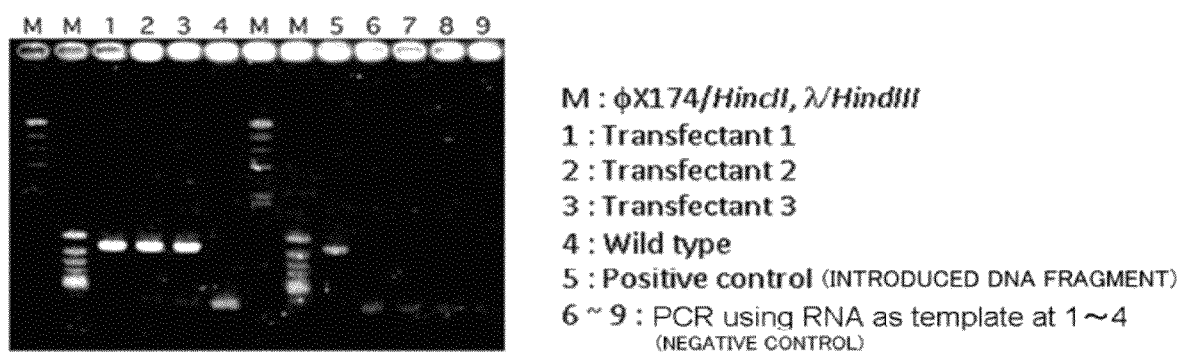
FIG. 20 represents evaluations of *T. aureum* transfectants by RT-PCR. Reference numerals: M: φX174/HincII, λ HindIII 1: Transfectant 1 2: Transfectant 2 3: Transfectant 3 4: Wild type 5: Positive control (introduced DNA fragment) 6 to 9: the same as 1 to 4 except that RNA was used as a template in PCR (negative control).

As with the case of the *A. limacinum* transfectants, it was found that the ub-Neo$^r$ incorporated in the chromosomal DNA was subject to transcription into mRNA (FIG. 20).

xi. Acquisition of *Thraustochytrium* sp. ATCC 26185 Transfectant

Figure 21:
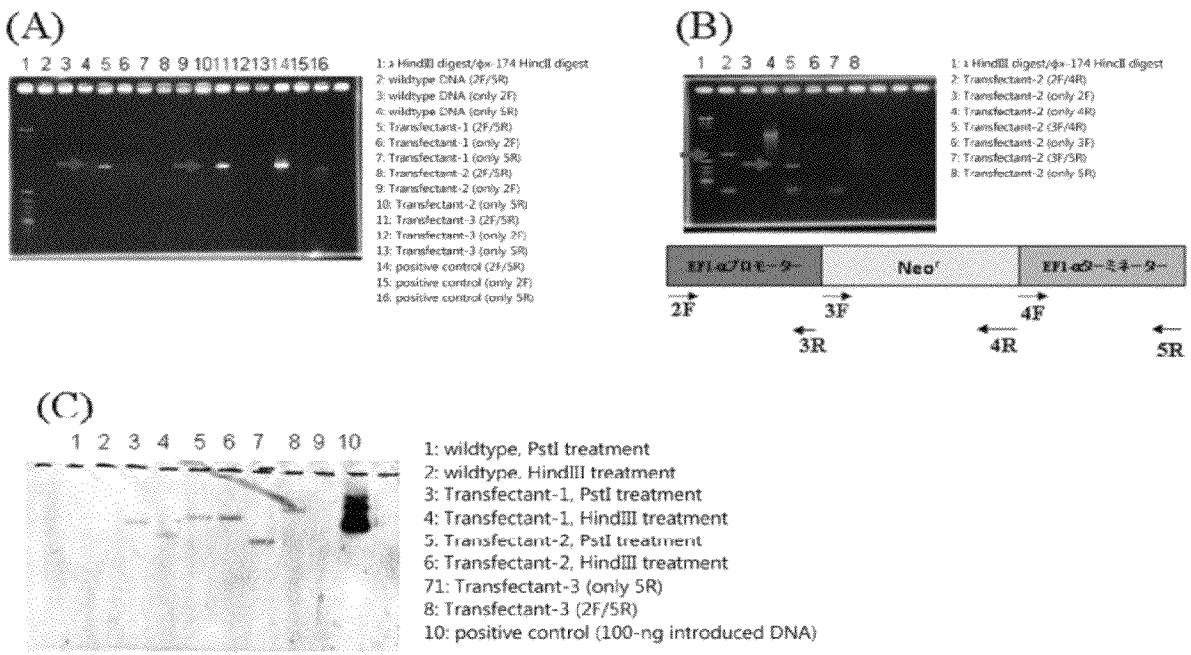
FIG. 21 represents evaluations of *Thraustochytrium* sp. ATCC 26185 transfectants by PCR using genomic DNA as a template, and by Southern blotting. Reference numerals: (A) 1: λ HindIII digest/φx-174 HincII digest 2: wild type DNA (2F/5R) 3: wild type DNA (only 2F) 4: wild type DNA (only 5R) 5: Transfectant-1 DNA (2F/5R) 6: Transfectant-1 DNA (only 2F) 71: Trnsfectant-1 DNA (only 5R) 8: Transfectant-2 DNA (2F/5R) 9: Transfectant-2 DNA (only 2F) 10: Transfectant-2 DNA (only 5R) 11: Transfectant-3 DNA (2F/5R) 12: Transfectant-3 RNA (only 2F) 13: Transfectant-3 RNA (only 5R) 14: positive control (2F/5R) 15: positive control (only 2F) 16: positive control (only 5R) (B) 1: λ HindIII digest/φx-174 HincII digest 2: Transfectant-2 DNA (2F/4R) 3: Transfectant-2 DNA (only 2F) 4: Transfectant-2 DNA (only 4R) 5: Transfectant-2 DNA (3F/4R) 6: Transfectant-2 DNA (only 3F) 7: Trnsfectant-2 DNA (3F/5R) 8: Transfectant-2 DNA (only 5R) (C) 1: wild type, PstI treatment; 2: wild type, HindIII treatment 3: Transfectant-1, PstI treatment 4: Transfectant-1, HindIII treatment 5: Transfectant-2 PstI treatment 6: Transfectant-2, HindIII treatment 71: Transfectant-3, PstI treatment 8: Transfectant-3, HindIII treatment 10: positive control (100-ng introduced DNA).

A linear Neo$^r$ expression cassette adopting EF-1α promoter and terminator (EF-Neo$^r$) was used as the introduced DNA. After investigating various conditions, transfectants were obtained by electroporation at a very low gene introduction efficiency ($10^{-1}$ cfu/µg DNA or less). It was also found that the transfectants maintained the G418 resistance even after being subcultured five times in a GY liquid medium containing no G418.

xii. Evaluation of *Thraustochytrium* sp. ATCC 26185 Transfectant by PCR Using Genomic DNA as Template and by Southern Blotting As with the case of the *A. limacinum* transfectants, random incorporation of EF-Neo$^r$ into the chromosomal DNA was confirmed by PCR using the genomic DNA as a template (FIG. 21A, B), and by Southern blotting detecting Neo$^r$ (FIG. 21C). However, a presence of partial defects in the terminator region was suggested in one of the three transfectants analyzed (Transfectant 2; FIG. 21B, lane7).

xiii. Evaluation of *Thraustochytrium* sp. ATCC 26185 Transfectant by RT-PCR

Figure 22:
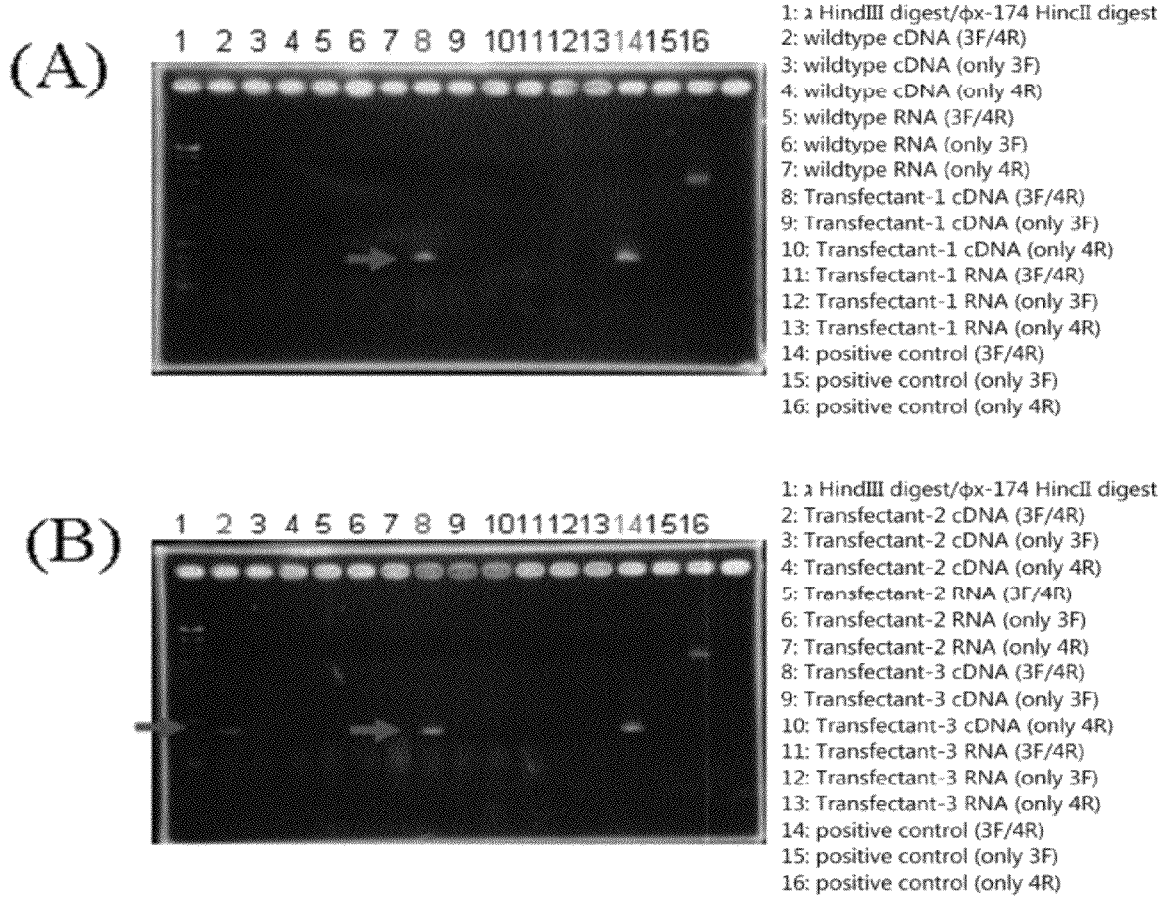
FIG. 22 represents evaluations of *Thraustochytrium* sp. ATCC 26185 transfectants by RT-PCR. Reference numerals: (A) 1: λ HindIII digest/φx-174 HincII digest 2: wild type cDNA (3F/4R) 3: wild type cDNA (only 3F) 4: wild type cDNA (only 4R) 5: wild type RNA (3F/4R) 6: wild type RNA (only 3F) 7: wild type RNA (only 4R) 8: Transfectant-1 cDNA (3F/4R) 9: Transfectant-1 cDNA (only 3F) 10: Transfectant-1 cDNA (only 4R) 11: Transfectant-1 RNA (3F/4R) 12: Transfectant-1 RNA (only 3F) 13: Transfectant-1 RNA (only 4R) 14: positive control (3F/4R) 15: positive control (only 3F) 16: positive control (only 4R) (B) 1: λ HindIII digest/φx-174 HincII digest 2: Transfectant-2 cDNA (3F/4R) 3: Transfectant-2 cDNA (only 3F) 4: Transfectant-2 cDNA (only 4R) 5: Transfectant-2 RNA (3F/4R) 6: Transfectant-2 RNA (only 3F) 7: Transfectant-2 RNA (only 4R) 8: Transfectant-3 cDNA (3F/4R) 9: Transfectant-3 cDNA (only 3F) 10: Transfectant-3 cDNA (only 4R) 11: Transfectant-3 RNA (3F/4R) 12: Transfectant-3 RNA (only 3F) 13: Transfectant-3 RNA (only 4R) 14: positive control (3F/4R) 15: positive control (only 3F) 16: positive control (only 4R).
Figure 23:
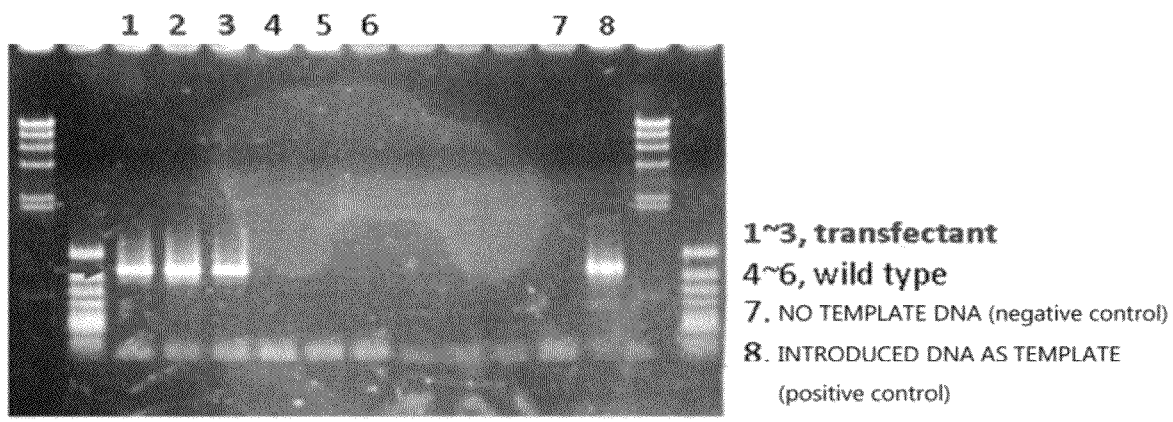
FIG. 23 represents evaluations of *Schizochytrium* sp. AL1Ac transfectants by PCR using genomic DNA as a template. Reference numerals: Lanes 1 to 3: Transfectant; Lanes 4 to 6: Wild-type strain; Lane 7: No template DNA (negative control); Lane 8: Introduced DNA was used as a template (positive control).

It was found that the EF-Neo$^r$ incorporated in the chromosomal DNA was subject to transcription into mRNA (FIG. 22A, B), including the Transfectant 2 in which partial defects in the terminator region were suggested (FIG. 22, lane 14).

xiv. Acquisition of *Schizochytrium* sp. AL1Ac Transfectant ub-Neo$^r$ was used as the introduced DNA. Despite investigation of various conditions, no transfectants could be obtained by electroporation. However, with the gene gun technique examined under different conditions, it was possible to obtain transfectants at a penetration pressure of 1,100 psi, even though the gene introduction efficiency was very low ($10^{-1}$ cfu/µg DNA or less). It was also found that the transfectants maintained the G418 resistance even after being subcultured five times in a GY liquid medium containing no G418.

xv. Evaluation of *Schizochytrium* sp. AL1Ac Transfectant by PCR Using Genomic DNA as Template As with the case of the *A. limacinum* transfectants, incorporation of the introduced DNA fragments in the chromosomal DNA was strongly suggested by PCR using the genomic DNA as a template (FIG. 23).

As the results of these gene introduction experiments demonstrate, it became possible to obtain transfectants of all four strains of *Labyrinthula* by random integration using the linear DNA, and electroporation or gene gun technique (Table 3).

TABLE 3

| Tested strain | Gene introduction method | Gene introduction efficiency |
|---|---|---|
| *A. limacinum* mh0186 | Electroporation | up to $1.2 \times 10^1$ cfu/µg DNA |
| *T. aureum* | Gene gun | up to $1.9 \times 10^2$ cfu/µg DNA |
| *Thraustochytrium* sp. | Electroperation | up to $10^0$ cfu/µg DNA |
| *Schizochytrium* sp. AL1Ac | Gene gun | up to $10^0$ cfu/µg DNA |

The G418 resistance of the transfectants was stable, suggesting that the introduced DNA was randomly incorporated in the chromosomal DNA, as evaluated by PCR using the genomic DNA as a template, or by Southern blotting analysis.

EXAMPLE 6

Expression of Foreign Protein in *Aurantiochytrium limacinum* mh0186 and *Thraustochytrium aureum* ATCC 34304 by Transformation (1) Expression of Aequorea green fluorescent protein (GFP)

i. Incorporation of GFP Gene into mh0186 Genomic DNA

The ubiquitin gene-derived promoter and terminator regions derived from *Thraustochytrium aureum* ATCC 34304 (obtained from American type culture collection), and Enhanced GFP gene (Clontech) were amplified by PCR using a PrimeSTAR GC polymerase kit (Takara Bio) (PCR cycles: 94° C. 2 min/94° C. 1 min, 62° C. 30 sec, 72° C. 1 min, 30 cycles/4° C.). The promoter region and the GFP gene were joined by fusion PCR using a PrimeSTAR GC polymerase kit (Takara Bio) (PCR cycles: 94° C. 2 min/94° C. 1 min, 62° C. 30 sec, 72° C. 2 min, 30 cycles/4° C.). By using this as a template, the promoter region, the GFP gene, and the terminator region were joined by fusion PCR with a PrimeSTAR GC polymerase kit (Takara Bio) (PCR cycles: 94° C. 2 min/ 94° C. 1 min, 62° C. 30 sec, 72° C. 3 min, 30 cycles/4° C.). The joined DNA fragment was then incorporated in a pGEM-T Easy vector (Promega). By using this plasmid as a template, a KpnI site was added to the both ends of the GFP gene cassette by PCR performed with primers Ub-pro-F1 (SEQ ID NO: 48 in the Sequence Listing) and Ub-term-R2 (SEQ ID NO: 49 in the Sequence Listing), using a PrimeSTAR GC polymerase kit (Takara Bio). The resulting cassette was then incorporated at the KpnI site (immediately following the terminator region) of a pUC18 vector including an artificially synthesized neomycin-resistant gene cassette (ubiquitin gene-derived promoter and terminator regions) to produce a GFP gene/neomycin-resistant gene expression cassette. The vector including the GFP gene/neomycin-resistant gene expression cassette was named pNeoGFP.

The GFP gene/neomycin-resistant gene expression cassette was amplified with primers Ub18Spro-F2 (SEQ ID NO: 50 in the Sequence Listing) and pUC18-R (SEQ ID NO: 51 in the Sequence Listing), using a PrimeSTAR GC polymerase kit (Takara Bio). After purification, the purified DNA fragment (5 μg) was introduced into the mh0186 strain. This was performed by following the gene introduction procedure in which cells cultured in a 200-ml GY liquid medium for 3 days were suspended in 0.3 M sorbitol (Wako Pure Chemical Industries, Ltd.) or in Nucleofector Solution L (lonza) used as a final cell suspension, and then subjected to electroporation under 0.75 kV, 50Ω, 50 μF conditions using a GENE PULSER® II (Bio-Rad Laboratories). The DNA fragments (0.625 μg) purified in a similar fashion were also introduced into *T. aureum* cultured in a 200-ml GY liquid medium for 5 days, by using the gene gun technique with a Standard Pressure Kit (Bio-Rad Laboratories) and a PDS-1000/He system (Bio-Rad Laboratories). The DNA was introduced by penetrating the cells applied onto a PDA agar plate medium (containing 2 mg/ml G418), under the following conditions: 0.6-micron gold particles, target distance 6 cm, vacuum 26 mmHg, Rupture disk 1,100 PSI.

For the mh0186 strain, genomic DNA was extracted from cells cultured in a 100-ml GY liquid medium (containing 0.5 mg/ml G418) for 3 days. In the case of *T. aureum*, genomic DNA was extracted from cells cultured in a 100-ml GY liquid medium (containing 2 mg/ml G418) for 7 days. The purity and the concentration of the extracted genomic DNA were measured by measuring A260/280 using an Ultrospec 3000 (Amersham Pharmacia Biotech). By using the extracted genomic DNA as a template, PCR was performed with primers 3F (SEQ ID NO: 52 in the Sequence Listing), 4R (SEQ ID NO: 53 in the Sequence Listing), Ub-GFP-F (SEQ ID NO: 54 in the Sequence Listing), and UB-GFP-R (SEQ ID NO: 55 in the Sequence Listing), using an LA Taq HS polymerase Kit (Takara Bio) (PCR cycles: 98° C. 2 min/98° C. 20 sec, 60° C. 30 sec, 72° C. 1 min, 30 cycles/4° C.).

Figure 24:
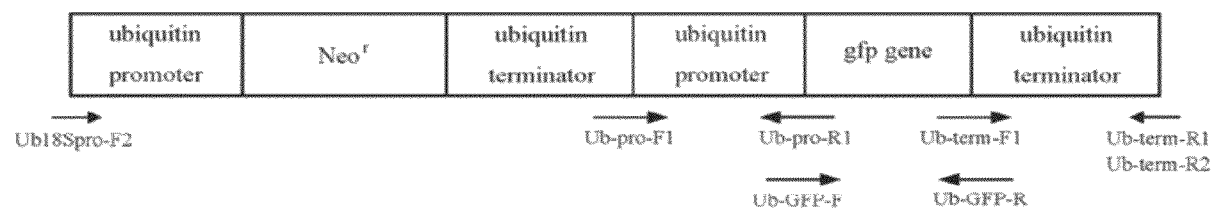
FIG. 24 is a schematic view of a GFP (Green Fluorescent Protein) gene/neomycin-resistant gene expression cassette. Ub-pro-F1 and Ub-term-R2 each include a KpnI site in the sequence.
Figure 25:
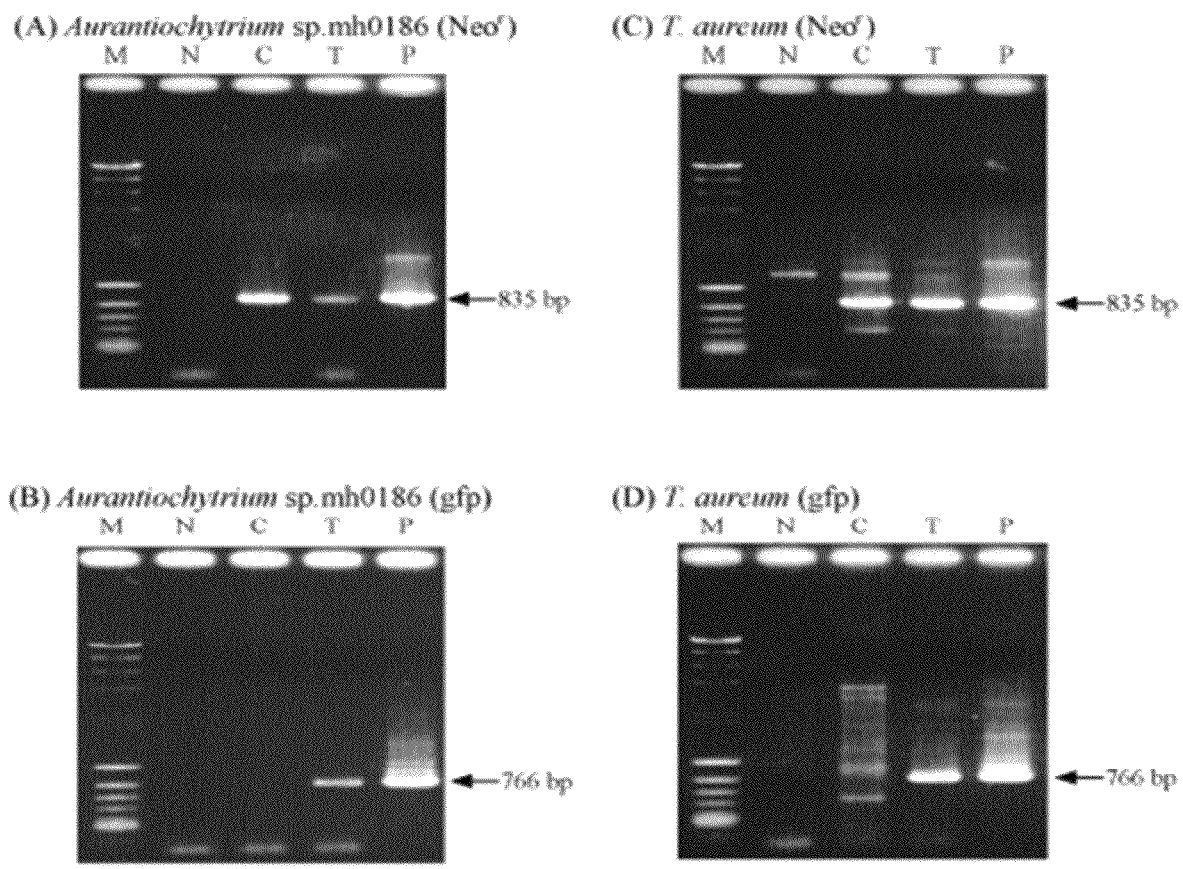
FIG. 25 represents PCR analyses of a control strain and a GFP gene/neomycin-resistant gene expression cassette-introduced strain, using genomic DNAs derived from these strains as templates. (A, B), PCR results for *Aurantiochytrium* sp.mh0186; (C, D), PCR results for *T. aureum*; (A, C), results of amplification of a neomycin-resistant gene; (B, D), results of amplification of a GFP gene. Reference numerals: M: λ HindIII digest/φx-174 HincII digest; N: wild-type strain (negative control); C: neomycin-resistant gene expression cassette-introduced strain (positive control in (A, C); negative control in (B, D)); T: GFP gene/neomycin-resistant gene expression cassette-introduced strain; P: GFP gene/neomycin-resistant gene expression cassette was used as a template (positive control).

Fusion PCR performed with the chimeric primers presented in Table 4 joined all the GFP gene, ubiquitin gene promoter region, and ubiquitin gene terminator region. The resulting fragment was incorporated at the KpnI site (immediately following the terminator region) of a pUC18 vector (Takara Bio) including an artificially synthesized neomycin-resistant gene cassette (ubiquitin gene-derived promoter and terminator regions) to produce a GFP gene/neomycin-resistant gene expression cassette (FIG. 24). Introducing the GFP gene/neomycin-resistant gene expression cassette into the *A. limacinum* mh0186 strain and *T. aureum* produced transfectants. These transfectants were subjected to a PCR using the genomic DNA as a template, and the result confirmed that the GFP gene and the neomycin-resistant gene were successfully incorporated into the genomic DNA of the GFP gene/neomycin-resistant gene expression cassette transfectants (FIG. 25).

TABLE 4

| Name | Sequence | Direction |
| --- | --- | --- |
| Ub18Spro-F2 (SEQ ID NO: 50) | 5'-AGAGGAAGGTGAAGTCGTAACAAGGCGTTAGA-3' | Forward |
| Ub-pro-F1 (SEQ ID NO: 48) | 5'-TC<u>GGTACC</u>CGTTAGAACGCGTAATACGAC-3' | Forward |
| Ub-pro-R1 (SEQ ID NO: 102) | 5'-TCCTCGCCCTTGCTCACCATGTTGGCTAGTGTTGCTTAGGT-3' | Reverse |
| Ub-GFP-F (SEQ ID NO: 54) | 5'-ACCTAAGCAACACTAGCCAACATGGTGAGCAAGGGCGAGGA-3' | Forward |
| Ub-GFP-R (SEQ ID NO: 55) | 5'-AGCACATACTACAGATAGCTTAGTTTTACTTGTACAGCTCGTCCA-3' | Reverse |
| Ub-term-F1 (SEQ ID NO: 103) | 5'-TGGACGAGCTGTACAAGTAAAACTAAGCTATCTGTAGTATGTGCT-3' | Forward |
| Ub-term-R1 (SEQ ID NO: 104) | 5'-ATCTAGAACCGCGTAATACGACTCACTATAGGGAGAC-3' | Reverse |
| Ub-term-R2 (SEQ ID NO: 49) | 5'-TC<u>GGTACC</u>ACCGCGTAATACGACTCACTATAGGGAGACTGCAGTT-3' | Reverse |
| pUC18-R (SEQ ID NO: 51) | 5'-AACAGCTATGACCATGATTACGAATTCGAGCTCGG-3' | Reverse |

Ub-pro-F1 and Ub-term-R2 have KpnI site in the sequence (underlined).

ii. GFP mRNA Expression

For the mh0186 strain, total RNA was extracted from a main cell culture incubated in a 100-ml GY liquid medium (containing 0.5 mg/ml G418) for 3 days. In the case of *T. aureum*, total RNA was extracted from cells cultured in a 100-ml GY liquid medium (containing 2 mg/ml G418) for 7 days. Sepasol RNAI Super (nacalai tesque) was used for the extraction. The total RNA was cleaned by using an RNeasy Mini Kit (QIAGEN). The purity of the total RNA was increased by a DNase treatment using a Cloned DNaseI (Takara Bio), and the purity and the concentration of the purified total RNA were measured by measuring A260/280 using an Ultrospec 3000 (Amersham Pharmacia Biotech). cDNA was produced from the purified total RNA using a PrimeScript™ Reverse Transcriptase (Takara Bio). By using the cDNA as a template, a PCR was performed with primers 3F (SEQ ID NO: 52 in the Sequence Listing), 4R (SEQ ID NO: 53 in the Sequence Listing), Ub-GFP-F (SEQ ID NO: 54 in the Sequence Listing), and UB-GFP-R (SEQ ID NO: 55 in the Sequence Listing), using an LA Taq HS polymerase kit (Takara Bio) (PCR cycles: 98° C. 2 min/98° C. 20 sec, 60° C. 30 sec, 72° C. 1 min, 30 cycles/4° C.).

Figure 26:
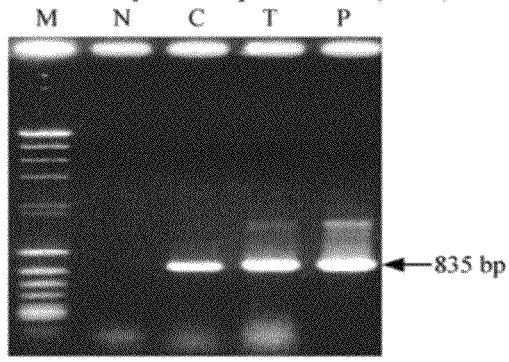
FIG. 26 represents PCR analyses of a control strain and a GFP gene/neomycin resistant gene expression cassette-introduced strain, using cDNAs derived from these strains as templates. (A, B), PCR results for *Aurantiochytrium* sp.mh0186; (C, D), PCR results for *T. aureum*; (A, C), results of amplification of a neomycin-resistant gene; (B, D), results of amplification of a GFP gene. Reference numerals: M: λ HindIII digest/φx-174 HincII digest; N: wild-type strain (negative control); C: neomycin-resistant gene expression cassette-introduced strain (positive control in (A, C); negative control in (B, D)); T: GFP gene/neomycin-resistant gene expression cassette-introduced strain; P: GFP gene/neomycin-resistant gene expression cassette was used as a template (positive control).
Figure 26:
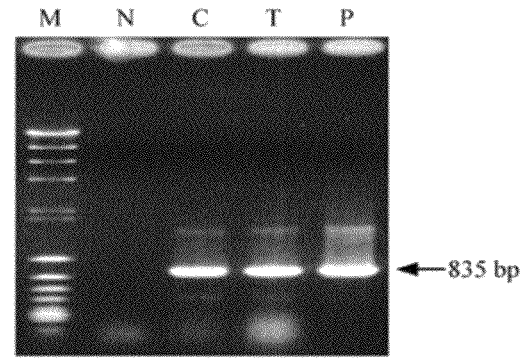
Figure 26:
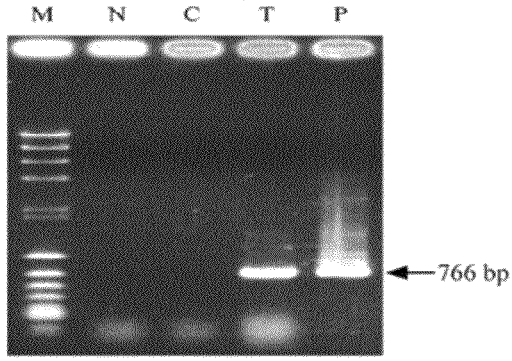
Figure 26:
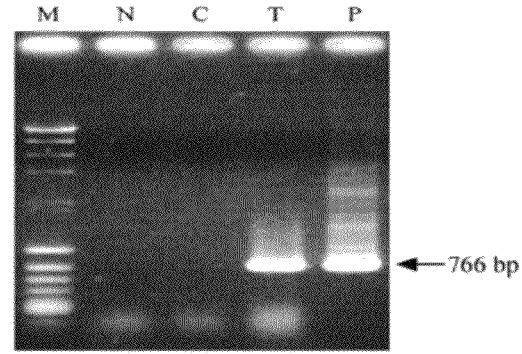

The result indicated that the incorporated GFP gene and neomycin-resistant gene were subject to transcription into mRNA (FIG. 26).

iii. GFP Expression

For the mh0186 strain, cells cultured in a 3-ml GY liquid medium (containing 0.5 mg/ml G418) for 3 days were harvested by centrifugation at room temperature, 3,500×g for 10 min. In the case of *T. aureum*, cells (1 ml) cultured in a 100-ml GY liquid medium (containing 2 mg/ml G418) for 7 days were harvested by centrifugation performed under the same conditions. The harvested cells were washed twice with a 500-μl sterilized SEA LIFE, observed under a confocal laser microscope (ECLIPSE TE2000-U; Nikon; 40×60 magnification, oil-immersion lens, excitation light Ar laser 488 nm), and imaged by using EZ-C1 software (Nikon).

Figure 27:
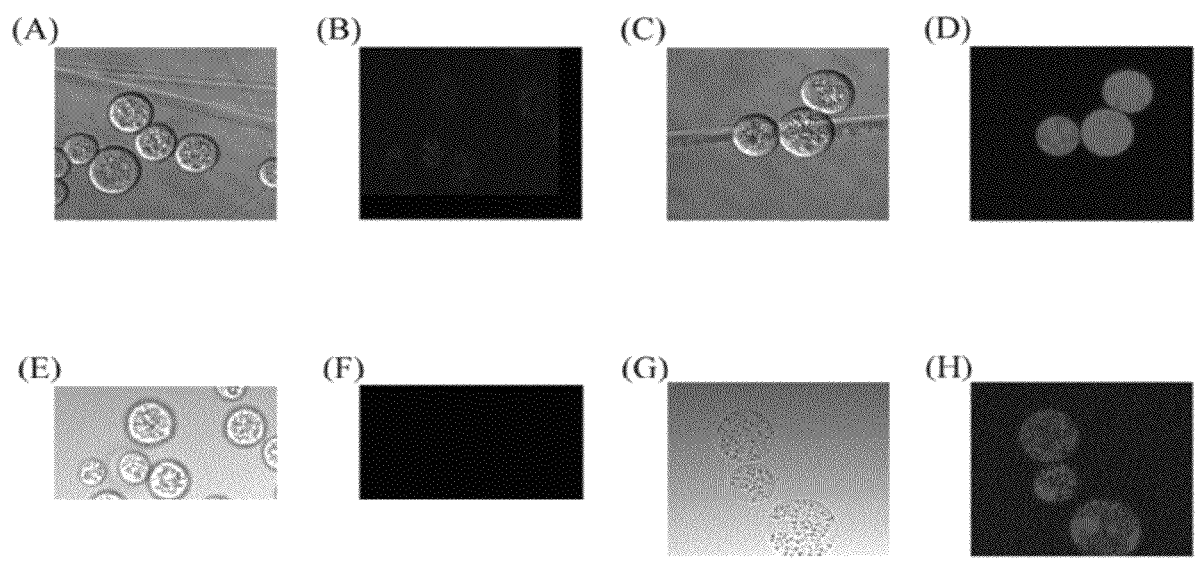
FIG. 27 represents the results of GFP fluorescence observation using a confocal laser microscope. (A), differential interference image of a *T. aureum* wild-type; (B), fluorescence image of a *T. aureum* wild-type; (C), differential interference image of GFP expressing *T. aureum*; (D), fluorescence image of GFP expressing *T. aureum*; (E), differential interference image of an *Aurantiochytrium* sp.mh0186 wild-type; (F), fluorescence image of an *Aurantiochytrium* sp.mh0186 wild-type; (G), differential interference image of GFP expressing *Aurantiochytrium* sp.mh0186; (H), fluorescence image of GFP expressing *Aurantiochytrium* sp.mh0186.

Confocal laser microscopy showed GFP fluorescence in the GFP gene/neomycin-resistant gene expression cassette transfectants, but not in the wild type (FIG. 27).

(2) Pinguiochrysis Δ12 Desaturase Expression i. Cloning of Δ12 Desaturase

Pinguiochrysis pyriformis MBIC 10872 (obtained from Marine Biotechnology Institute Culture collection) was cultured in ESM medium (produced according to the method described in the medium list of the NIES collection), and cells at the late stage of the logarithmic growth phase were harvested by centrifugation at 4° C., 6,000×g for 15 min. The harvested cells were frozen by liquid nitrogen, and total RNA was extracted by using the phenol/SDS/LiCl technique (1). Then, poly (A) +RNA was purified from the total RNA, using a mRNA Purification Kit (GE healthcare Bio-sciences). Single-stranded cDNA was then produced from the purified poly (A) +RNA, using a Ready-To-Go T-Primed First-Strand Kit (GE healthcare Bio-sciences). By using the cDNA as a template, a PCR was performed with primers F1 (SEQ ID NO: 56 in the Sequence Listing) and R1 (SEQ ID NO: 57 in the Sequence Listing) produced based on a known conserved sequence of Δ12 desaturase, using an Advantage™ 2 PCR Kit (Clontech) (PCR cycles: 95° C. 30 sec, 50° C. 30 sec, 68° C. 2 min, 40 cycles/4° C.). The amplified PCR product was incorporated in a pGEM-T easy vector (Promega), and introduced into competent cells DH5α (Toyobo) by electroporation. By using the extracted transfectant plasmid as a template, the base sequence was analyzed by sequencing using a Dye Terminator Cycle Sequencing Kit (BECKMAN COULTER). A P. pyriformis, cDNA library was constructed using a Lambda cDNA Library Construction Kits (Stratagene). Screening of positive clones was performed by plaque hybridization using an ECL Direct Nucleic Acid Labeling and Detection System (GE healthcare Bio-sciences). As to the incubation conditions with the probe, the clones were incubated at 42° C. for 3 hours with a labeled probe added in an 8 ng/ml concentration, and washed twice at 55° C. for 10 min (primary washing with no urea), and twice at room temperature for 5 min (secondary washing with no urea). As the probe, a 314-bp cDNA fragment amplified by a PCR with primers SP1/F (SEQ ID NO: 58 in the Sequence Listing) and SP1/R (SEQ ID NO: 59 in the Sequence Listing) using an Advantage™ 2 PCR Kit (Clontech) was used (PCR cycles: 94° C. 3 min/94° C. 30 sec, 56° C. 30 sec, 68° C. 1 min, 35 cycles/4° C.). A plasmid containing the acquired partial sequence was used as a template in the PCR. After several screenings, the positive clones were transferred from the λ phage to a pBluescript (Stratagene) using an ExAssist helper phage (Stratagene).

As a result, a 515-bp putative Δ12 desaturase gene partial sequence was successfully amplified. Screening of positive clones including the full length of the target gene by plaque hybridization using the acquired DNA fragment as a probe successfully isolated seven positive clones from $5.5 \times 10^6$ clones. Analyses of these sequences suggested that the acquired gene was a gene containing a 1,314-bp ORF encoding 437 amino acids.

ii. Alignment with Δ12 Desaturases Derived from Other Organisms

Multiple alignment analysis was performed for the amino acid sequences of P. pyriformis-, fungus-, and protozoa-derived Δ12 desaturases, using ClustalW 1.81 and ESPript 2.2 (http://espript.ibcp.fr/ESPript/cgi-bin/ESPript.cgi).

Figure 28:
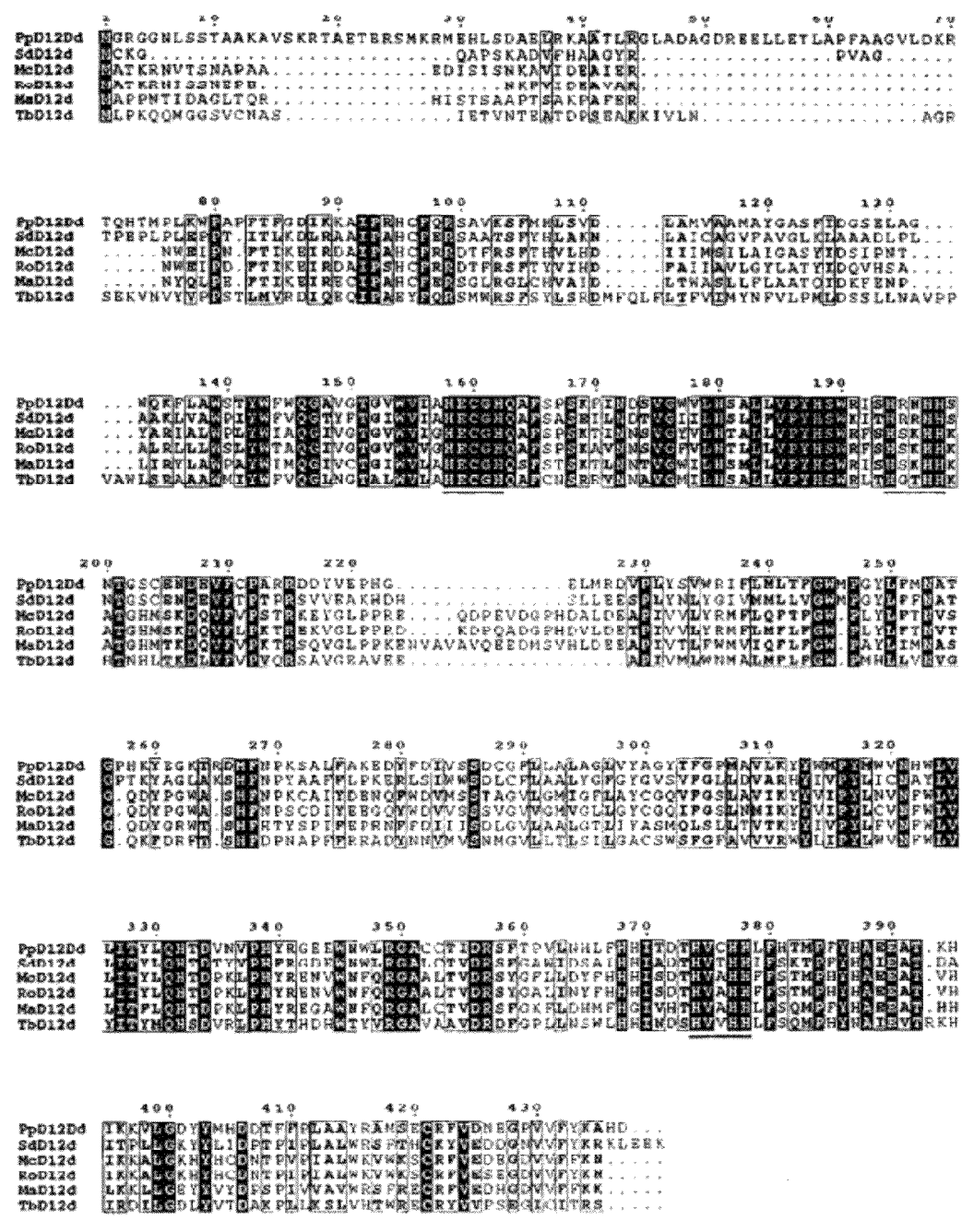

It was found as a result that the amino acid sequence of the acquired gene had high homology with the amino acid sequences of the Δ12 desaturase genes derived from other organisms (FIG. 28). Further, the putative amino acid sequence of the acquired gene conserved three histidine boxes commonly conserved in desaturase (FIG. 28).

iii. Phylogenetic Analysis

A molecular phylogenetic tree of Δ12 desaturases and Δ12/Δ15 desaturases, including the P. pyriformis,-derived Δ12 desaturase, was created by using the maximum-likelihood method with a MOLPHY version 2.3 computer program package (Non-Patent Document 13). First, multiple alignment was performed with ClustalW 1.81 for all amino acid sequences. After removing the uncertain portions, a search for a maximum-likelihood phylogenetic tree was made, using the phylogenetic tree by the neighbor-joining method (2) as the initial phylogenetic tree.

As a result, the acquired putative Δ12 desaturase, and the Δ12 desaturases and Δ12/Δ15 desaturases derived from other organisms were classified into three lineage groups: a fungal & nematode Δ12 desaturase group, a plant Δ12 desaturase group, and a cyanobacterial and chloroplast-localized plant Δ12 desaturase group. The acquired putative Δ12 desaturase was classified into the fungal & nematode Δ12 desaturase group, showing that the *Saprolegnia diclina*-derived Δ12 desaturase was the closest relative (FIG. 29).

iv. Expression of Δ12 Desaturase in Yeast

By using a plasmid containing the full length of the P. pyriformis-derived Δ12 desaturase gene as a template, a PCR was performed with primers Pry-F (SEQ ID NO: 60 in the Sequence Listing) and Pyr-R (SEQ ID NO: 61 in the Sequence Listing), using a PrimeSTAR GC polymerase kit (TakaraBio). The PCR added a HindIII restriction enzyme site and an XbaI restriction enzyme site at the both ends. The amplified fragments were incorporated in a pGEM-T-Easy vector (Promega), and sequence analysis was performed. The Δ12 desaturase gene was cut out by HindIII/XbaI treatment from a plasmid that did not have amplification error, and incorporated into a yeast vector pYES2/CT (Invitrogen) subjected to the same restriction enzyme treatment. As a result, a Δ12 desaturase gene expression vector pYpΔ12Des was constructed. The Δ12 desaturase gene expression vector pYpΔ12Des and the pYES2/CT were introduced into a budding yeast *Saccharomyces cerevisiae* by using the lithium acetate method, according to the methods described in Current Protocols in Molecular Biology, Unit 13 (Ausubel et al., 1994) and in Guide to Yeast Genetics and Molecular Biology (Gutherie and Fink, 1991), and the yeasts were screened for transfectants. The transfectants (pYpΔ12Des introduced strain and mock introduced strain) were cultured according to the method of Qiu et al. (Qiu, X., et al. J. Biol. Chem. (2001) 276, 31561-6), and the extraction and methylesterification of the yeast-derived fatty acids were performed. A gas chromatograph GC-2014 (Shimadzu Corporation) was used for GC analysis, which was performed under the following conditions. Column: HR-SS-10 (30 m×0.25 mm; Shinwa Chemical Industries Ltd.), column temperature: 150° C.→(5° C./min)→220° C. (10 min), carrier gas: He (1.3 mL/min). GC-17A and GCMS-QP-5000 (Shimadzu Corporation) were used for GC-MS analysis, which was performed under the following conditions. DB-1 capillary column (0.25 mmi.d.× 30 m, film thickness 0.25 μm; Agilent), column temperature 160° C.→(4° C./min)→260° C., injector port temperature 250° C. For peaks that caused troubles in the analyses, the fatty acids were analyzed after picolinyl esterification, using the same apparatuses and columns under the temperature condition 240° C.→(2.5° C./min)→260° C. (15 min)→(2.5° C./min)→280° C.

In order to verify that the Δ12 desaturase was encoded by the acquired gene, an expression vector was constructed, and an expression experiment was conducted using a budding yeast *S. cerevisiae* (Invitrogen) as a host. A GC analysis of the fatty acid compositions of the pYpΔ12Des introduced strain and the pYES2/CT introduced strain confirmed a new peak in the pYpΔ12Des introduced strain at a position corresponding to the retention time of linoleic acid, but not in the mock control (FIG. 30). A GC-MS analysis of this new peak revealed that the molecular weight and the fragment pattern coincide with those of the sample linoleic acid methyl ester (FIG. 31). The conversion efficiency from oleic acid to linoleic acid was 23.5±1.23%, as calculated according to the following equation.

Conversion efficiency (%)=product (%)/(product (%)+ substrate (%))×100

No activity for other fatty acids was observed (Table 5).

TABLE 5

All foreign substrates were added to make the final concentration 40 μM. Substrate (%) and product (%) are the percentage with respect to the total fatty acid (GC peak area). Conversion efficiency (%) = 100 × ([product]/[product + substrate]). All values are mean values ± standard deviation. n = 3

| Substrate | Substrate (%) | Product | Product (%) | Conversion efficiency (%) |
|---|---|---|---|---|
| Mock | | | | |
| $18:1^{\Delta 9a}$ | 29.6 ± 1.15 | $18:2^{\Delta 9, 12}$ | $ND^c$ | 0 |
| $16:1^{\Delta 9a}$ | 47.04 ± 0.62 | $16:2^{\Delta 9, 12}$ | $ND^c$ | 0 |
| pYpΔ12des | | | | |
| $14:1^{\Delta 9b}$ | 3.99 ± 0.38 | $14:2^{\Delta 9, 12}$ | $ND^c$ | |
| $16:1^{\Delta 9a}$ | 45.8 ± 0.80 | $16:2^{\Delta 9, 12}$ | $ND^c$ | |
| $18:1^{\Delta 9a}$ | 21.3 ± 0.27 | $18:2^{\Delta 9, 12}$ | 6.56 ± 0.49 | 23.5 ± 1.23 |
| $18:1^{trans\Delta 9b}$ | 7.60 ± 2.23 | $18:2^{trans\Delta 9, 12}$ | $ND^c$ | |
| $18:2^{\Delta 9, 12b}$ | 18.5 ± 0.30 | $18:3^{\Delta 9, 12, 15}$ | $ND^c$ | |
| $18:3^{\Delta 6, 9, 12b}$ | 16.3 ± 1.32 | $18:4^{\Delta 6, 9, 12, 15}$ | $ND^c$ | |
| $20:3^{\Delta 8, 11, 14b}$ | 18.8 ± 0.31 | $20:4^{\Delta 8, 11, 14, 17}$ | $ND^c$ | |
| $20:4^{\Delta 5, 8, 11, 14b}$ | 26.8 ± 0.75 | $20:5^{\Delta 5, 8, 11, 14, 17}$ | $ND^c$ | |
| $22:4^{\Delta 7, 10, 13, 16b}$ | 4.21 ± 0.16 | $22:5^{\Delta 7, 10, 13, 16, 19}$ | $ND^c$ | |

[a] Endogenous fatty acid
[b] Exogenous fatty acid
[c] ND, below detection limit v. Incorporation of Δ12 Desaturase Gene into mh0186 Genomic DNA First, ubiquitin gene-derived promoter and terminator regions, and the Δ12 desaturase gene were amplified by PCR using a PrimeSTAR GC polymerase kit (Takara Bio) (PCR cycles: 94° C. 2 min/94° C. 1 min, 62° C. 30 sec, 72° C. 1.5 min, 30 cycles/4° C.) The promoter region and the Δ12 desaturase gene were then joined by fusion PCR using a PrimeSTAR GC polymerase kit (Takara Bio) (PCR cycles: 94° C. 2 min/94° C. 1 min, 62° C. 30 sec, 72° C. 2.5 min, 30 cycles/4° C.). By using this as a template, the promoter region, the GFP gene, and the terminator region were joined by fusion PCR using a PrimeSTAR GC polymerase kit (Takara Bio) (PCR cycles: 94° C. 2 min/94° C. 1 min, 62° C. 30 sec, 72° C. 3 min, 30 cycles/4° C.). The joined DNA fragment was then incorporated into a pGEM-T Easy vector (Promega). By using this plasmid as a template, a single-base mutation was introduced at the KpnI site in the Δ12 desaturase gene sequence using a PrimeSTAR MAX DNA polymerase (Takara Bio). The joined fragment was cut out by KpnI treatment, and incorporated at the KpnI site of a pUC18 vector (Takara Bio) including an artificially synthesized neomycin-resistant gene cassette (EF1-α gene-derived promoter region and terminator region are joined at the both ends). The vector including the Δ12 desaturase gene/neomycin-resistant gene expression cassette was named pNeoDes12. The sequences of the PCR primers used are presented in Table 6. The Δ12 desaturase gene/neomycin-resistant gene expression cassette was amplified with primers 2F (SEQ ID NO: 62 in the Sequence Listing) and pUC18-R (SEQ ID NO: 51 in the Sequence Listing), using a PrimeSTAR GC polymerase kit, and purified. After purification, the purified DNA fragment (5 μg) was introduced into the mh0186 strain as in (1)-1. Nucleofector Solution L (lonza) was used as a final cell suspension. Genomic DNA was extracted from a main cell culture incubated in a 100-ml GY liquid medium (containing 0.5 or 2 mg/ml G418) for 3 days, and the purity and the concentration of the extracted genomic DNA were measured by measuring A260/280 using an Ultrospec 3000 (Amersham Pharmacia Biotech). By using the extracted genomic DNA as a template, a PCR was performed with primers 3F (SEQ ID NO: 52 in the Sequence Listing), 4R (SEQ ID NO: 53 in the Sequence Listing), ub pro-D12d-F (SEQ ID NO: 63 in the Sequence Listing), and ub term-Δ12d-R (SEQ ID NO: 64 in the Sequence Listing), using an LA Taq HS polymerase Kit (Takara Bio) (PCR cycles: 98° C. 2 min/98° C. 20 sec, 60° C. 30 sec, 72° C. 1.5 min, 30 cycles/4° C.).

Fusion PCR using the chimeric primers presented in Table 6 successfully joined all the Δ12 desaturase gene, ubiquitin gene promoter region, and ubiquitin gene terminator region. The joined fragment was incorporated at the KpnI site of a pUC18 vector including an artificially synthesized neomycin-resistant gene cassette (EF1-α gene-derived promoter and terminator regions) to produce a Δ12 desaturase gene/neomycin-resistant gene expression cassette (FIG. 32). Introducing the Δ12 desaturase gene/neomycin-resistant gene expression cassette into the mh0186 strain successfully produced transfectants. These transfectants were subjected to a PCR using the genomic DNA as a template, and the result confirmed that the Δ12 desaturase gene and the neomycin-resistant gene were successfully incorporated in the genomic DNA of the Δ12 desaturase gene/neomycin-resistant gene expression cassette transfectants (FIG. 33).

Introducing the Δ12 desaturase gene/neomycin-resistant gene expression cassette into *T. aureum* successfully produced transfectants. These transfectants were subjected to

TABLE 6

| Name | Sequence | Direction |
|---|---|---|
| 18S (SEQ ID NO: 105) | 5'-CG<u>AATATT</u>CCTGGTTGATCCTGCCAGTAGT-3' | Forward |
| 1R (SEQ ID NO: 106) | 5'-GTAACGGCTTTTTTTGAATTGCAGGTTCACTACGGAAACCTTGTTA-3' | Reverse |
| 2F (SEQ ID NO: 32) | 5'-GGTTTCCGTAGTGAACCTGCAATTCAAAAAAAGCCGTTACTCACAT-3' | Forward |
| 3R (SEQ ID NO: 107) | 5'-AAGGCCGTCCTGTTCAATCATCTAGCCTTCCTTTGCCGCTGCTTGCT-3' | Reverse |
| 3F (SEQ ID NO: 52) | 5'-CAGCGGCAAAGGAAGGCTAGATGATTGAACAGGACGGCCTTCACGC-3' | Forward |
| 4R (SEQ ID NO: 53) | 5'-GCGCATAGCCGGCGCGGATCTCAAAAGAACTCGTCCAGGAGGCGGT-3' | Reverse |
| 4F (SEQ ID NO: 37) | 5'-TCCTGGACGAGTTCTTTTGAGATCCGCGCCGGCTATGCGCCCGTGC-3' | Forward |
| 5R (SEQ ID NO: 33) | 5'-CA<u>CTGCAG</u>CGAAAGACGGGCCGTAAGGACG-3' | Reverse |
| Ub-pro-F1 (SEQ ID NO: 48) | 5'-TC<u>GGTACC</u>CGTTAGAACGCGTAATACGAC-3' | Forward |
| ub-pro-D12d-R (SEQ ID NO: 108) | 5'-AGGTTTCCTCCACGACCCATGTTGGCTAGTGTTGCTTAGGTCGCT-3' | Reverse |
| ub-pro-D12d-F (SEQ ID NO: 63) | 5'-CCTAAGCAACACTAGCCAACATGGGTCGTGGAGGAAACCTCTCCA-3' | Forward |
| ub term-D12d-R (SEQ ID NO: 64) | 5'-ATACTACAGATAGCTTAGTTTTAGTCGTGCGCCTTGTAGAACACA-3' | Reverse |
| ub D12d-term-F (SEQ ID NO: 109) | 5'-TCTACAAGGCGCACGACTAAAACTAAGCTATCTGTAGTATGTGCT-3' | Forward |
| Ub-term-R2 (SEQ ID NO: 49) | 5'-TC<u>GGTACC</u>ACCGCGTAATACGACTCACTATAGGGAGACTGCAGTT-3' | Reverse |
| pUC18-R (SEQ ID NO: 51) | 5'-AACAGCTATGACCATGATTACGAATTCGAGCTCGG-3' | Reverse |
| D12d-F2 (SEQ ID NO: 110) | 5'-CGCGGTGGG*C*ACCGGTGTCTGGGTCATCGC-3' | Forward |
| D12d-R2 (SEQ ID NO: 111) | 5'-ACACCGGT*G*CCCACCGCGCCCTGCCAGAA-3' | Reverse |

18S and 5R has SspI site or PstI site in the sequence (underlined).
Ub-pro-F1 and Ub-term-R2 has KpnI site in the sequence (underlined).
Bold italicized letters in the D12d-F2 and D12d-R2 sequences indicate mutated bases.

vi. Incorporation of Δ12 Desaturase Gene in *T. aureum* Genomic DNA

The Δ12 desaturase gene/neomycin-resistant gene expression cassette was amplified with primers 2F (SEQ ID NO: 62 in the Sequence Listing) and pUC18-R (SEQ ID NO: 51 in the Sequence Listing), using a PrimeSTAR GC polymerase kit, and purified. After purification, the purified DNA fragment (0.625 μg) was introduced into cells cultured in a 200-ml GY liquid medium for 5 days, using the gene gun technique with a Standard Pressure Kit (Bio-Rad Laboratories) and a PDS-1000/He system (Bio-Rad Laboratories). The DNA was introduced by penetrating the cells appl using the cDNA as a template, a PCR was performed with primers 3F (SEQ ID NO: 52 in the Sequence Listing), 4R (SEQ ID NO: 53 in the Sequence Listing), ubpro-D12d-F (SEQ ID NO: 63 in the Sequence Listing), and ub term-D12d-R (SEQ ID NO: 64 in the Sequence Listing), using an LA Taq HS polymerase kit (Takara Bio) (PCR cycles: 98° C. 2 min/98° C. 20 sec, 60° C. 30 sec, 72° C. 1.5 min, 30 cycles/4° C.).

The result of the PCR using the cDNA as a template indicated that the incorporated Δ12 desaturase gene and neomycin-resistant gene were transcribed into mRNA (FIG. 34).

(3) Expression of *Thraustochytrium aureum*-Derived Δ5 Desaturase i. Cloning of Δ5 Desaturase Primers 3F (SEQ ID NO: 65 in the Sequence Listing) and 1R (SEQ ID NO: 66 in the Sequence Listing) were produced in the conserved region present in the sequence of the Δ5 desaturase of *Thraustochytrium* sp. ATCC 26185, a closely related species of *Thraustochytrium aureum* ATCC 34304. This was followed by a nested PCR with an Advantage 2 PCR Kit (Clontech), using a *T. aureum*-derived RACE cDNA library as a template (PCR cycles: 94° C. 30 sec, 50° C. 30 sec, 72° C. 2 min, 30 cycle). As a result, an amplification product of the target size was obtained with a bracketing primer set (1R NES: SEQ ID NO: 67 in the Sequence Listing).

Analysis of the DNA fragment of the expected size (550 bp) obtained with the bracketing primers revealed that the DNA fragment was of the *T. aureum* Δ5 desaturase. Accordingly, primers with a 100% match (RACEd5F: SEQ ID NO: 68 in the Sequence Listing, and RACEd5FNES: SEQ ID NO: 69 in the Sequence Listing) were produced from the amplified fragment, and RACE PCR was performed using an Advantage 2 PCR Kit (PCR cycles: 94° C. 30 sec, 50° C. 30 sec, 72° C. 2 min, 30 cycle). As a result, a 700-bp 3'-end of the Δ5 desaturase was obtained.

A reverse primer GSP1 (SEQ ID NO: 70 in the Sequence Listing) was produced from this known sequence, and a 5' RACE PCR was performed (PCR cycles: 94° C. 30 sec/72° C. 3 min, 5 cycles, 94° C. 30 sec/70° C. 30 sec/72° C. 3 min, 5 cycles, 94° C. 30 sec/68° C. 30 sec/72° C. 3 min, 20 cycles). The resulting 5' RACE product was shorter than the expected size. Thus, instead of the PCR using the cDNA as a template, a PCR using a genome cassette library (TaKaRa LA PCR in vitro Cloning Kit) as a template was performed as above (primer GSP2; SEQ ID NO: 71 in the Sequence Listing). PCR using a BglII cassette library as a template produced a genome sequence about 2.5 kbp upstream of the primer producing site.

The upstream sequence obtained by using the genome walking technique included the start codon for Δ5 desaturase, and there was no presence of introns in the genome analyzed. From the sequences obtained by 3'-RACE or 5'-RACE, the full-length sequence information of Δ5 desaturase was acquired. The full-length sequence consisted of 439 amino acids with a 1,320-bp ORF, and contained a single cytochrome b5 domain (HPGGSI) and three histidine boxes (HECGH, HSKHH, and QIEHH), highly conserved regions of Δ5 desaturase. Based on this information, a PCR was performed with the primers d5fulllengthF (SEQ ID NO: 72 in the Sequence Listing) and d5fulllengthR (SEQ ID NO: 73 in the Sequence Listing) produced at the ORF ends, using the cDNA as a template (PCR cycles: 94° C. for 30 s, 60° C. for 30 s, and 72° C. for 2 min, 30 cycles). As a result, a full-length *T. aureum*-derived Δ5 desaturase was isolated.

ii. Alignment with Δ5 Desaturases Derived from Other Organisms

Multiple alignment was performed with ClustalX-1.83.1, using the amino acid sequence of *T. aureum*-derived Δ5 desaturase, and the amino acid sequences of Δ5 desaturases derived from *Thraustochytrium* sp. ATCC 26185, *Dictyostelium discoideum*, *Rattus norvegicus*, *Mus musculus*, *Homo sapiens*, *Caenorhabditis elegans*, and *Leishmania major* (FIG. 35).

The result showed that the *T. aureum*-derived Δ5 desaturase at the amino acid level had significant homology with the Δ5 desaturase genes derived from other organisms (*D. discoideum*: 34%, *R. norvegicus*: 28%, *M. musculus*: 28%, *H. sapiens*: 26%). The homology was particularly high (57%) with the *Thraustochytrium* sp. belonging to the same genus.

iii. Phylogenetic Analysis

A molecular phylogenetic tree of all desaturase genes, including the *T. aureum*-derived Δ5 desaturase, was created by using the maximum-likelihood method with molphy. First, the all sequences were prepared into Fasta format, and multiple alignment was performed using clustalW. After removing the uncertain portions, a search was made for a maximum-likelihood phylogenetic tree, using the phylogenetic tree by the neighbor-joining method as the initial phylogenetic tree.

It was found as a result that the acquired gene was close to the protozoa-derived desaturase group, and classified into the same lineage group to which the Δ5 desaturases derived from *Thraustochytrium* sp. ATCC 26185 and *L. major* belong (FIG. 36).

iv. Expression of Δ5 Desaturase in Yeast

In order to verify that the acquired gene was Δ5 desaturase, overexpression experiment was conducted using a budding yeast *S. cerevisiae* as a host. First, the acquired gene was incorporated at the EcoRI/XhoI site of a yeast vector pYES2/CT (Invitrogen) to construct an expression vector pYΔ5des. The constructed expression vector pY5Δdes was then introduced into *S. cerevisiae*, and GC analysis was performed after extracting and methylating the transfectant fatty acids obtained by using the lithium acetate technique. A gas chromatograph GC-2014 (Shimadzu Corporation) was used for the GC analysis, which was performed under the following conditions. Column: HR-SS-10 (30 m×0.25 mm; Shinwa Chemical Industries Ltd.), column temperature: 150° C.→(5° C./min)→220° C. (10 min), carrier gas: He (1.3 mL/min). GC-17A and GCMS-QP-5000 (Shimadzu Corporation) were used for GC-MS analysis, which was performed using a DB-1 capillary column (0.25 mmi.d.×30 m, film thickness 0.25 μm; Agilent) under the following conditions: column temperature 160° C.→(4° C./min)→260° C., injector port temperature 250° C. For peaks that caused troubles in the analyses, the fatty acids were analyzed after picolinyl esterification, using the same apparatuses and columns under the temperature condition 240° C.→(2.5° C./min)→260° C. (15 min)→(2.5° C./min)→280° C.

As a result, eicosatetraenoic acid (ETA; C20:4 Δ8, 11, 14, 17), and dihomo-γ-linoleic acid (DGLA; C20:3 Δ8, 11, 14)—known precursor substances of Δ5 desaturase—were converted into EPA and arachidonic acid (AA; C20:4 n-6), respectively. Conversion efficiencies were 32% and 27%, respectively. No specificity for other substrates was observed. GC-MS confirmed a match in the structures of the conversion products EPA and AA (FIG. 37a to c, Table 7)

TABLE 7

| Fatty acid substrates | Percentage of substrate converted (%) |
|---|---|
| C18:3n – 3 (-Linolenic acid (ALA) | 0.0 |
| C18:2n – 6 Linoleic acid (LA) | 0.0 |
| C20:4n – 3 Eicosatetraenoic acid (ETA) | 32.0 |
| C20:3n – 6 Dihomo-g-linolenic acid (DGLA) | 27.0 |
| C20:3n – 3 Eicosatrienoic acid | 0.0 |
| C20:2n – 6 Eicosadienoic acid | 0.0 |
| C22:5n – 3 Docosapentaenoic acid (DPA) | 0.0 |
| C22:4n – 6 Docosatetraenoic acid (DTA) | 0.0 |

Conversion rate = (product × 100)/(substrate + product)

v. Incorporation of Δ5 Desaturase Gene into mh0186 Genomic DNA

*T. aureum* ATCC 34304-derived ubiquitin gene promoter/terminator were isolated to construct an expression vector. To begin with, the ubiquitin gene was isolated by using the RACE method, as follows. First, a 3' fragment of the ubiquitin gene was amplified by PCR with a degenerate primer 2F (SEQ ID NO: 74 in the Sequence Listing), using the cDNA as a template.

Next, a 5' RACE System for Rapid Amplification of cDNA Ends, version 2.0 (invitrogen) was used to produce a reverse-transcription primer 1R (SEQ ID NO: 17 in the Sequence Listing) and a 5' RACE primer (SEQ ID NO: 75 in the Sequence Listing), and the kit was operated to obtain a 5' RACE product.

Based on the ORF sequence of the ubiquitin gene, primers REVERS-U PR-1 (SEQ ID NO: 22 in the Sequence Listing) and REVERS-U PR-2 (SEQ ID NO: 23 in the Sequence Listing) were produced, and a PCR was performed by using the genome walking technique (PCR cycles: 98° C. 30 sec/60° C. 30 sec/72° C. 2 min, 30 cycles). As a result, a 812-bp promoter region was isolated by PCR using a SalI cassette library as a template.

Next, the terminator was isolated using the same method, and a 612-bp DNA fragment was obtained.

Note that the PCR used the primer ubqterminalf1 (SEQ ID NO: 24 in the Sequence Listing) in the 1st PCR, and the primer ter2F (SEQ ID NO: 25 in the Sequence Listing) in the 2nd PCR, and was performed in a PCR cycle consisting of 94° C. 30 sec/60° C. 30 sec/72° C. 3 min, 30 cycles. The amplified fragments were joined by fusion PCR, and incorporated in pUC18 to produce a cyclic vector as shown in FIG. 38*a*. The introduced gene fragments shown in FIG. 38*b* were then prepared by PCR.

Next, a gene introduction experiment was conducted using *Aurantiochytrium* sp. mh0186. First, single colonies of the *Aurantiochytrium* sp. mh0186 strain were cultured in GY medium at 25° C. until the logarithmic growth phase, and the supernatant was removed by centrifugation at 3,500×g, 4° C. for 15 min. Cells (5×10$^6$) were suspended in a Nucleofector kit L (amaxa), and pulsated twice with the introduced DNA under 0.75 kV, 50 Ω, 50 µF conditions using a Bio Rad Gene Pulser II (Bio-Rad Laboratories). After quickly adding PD liquid medium (1 ml), a shake culture was performed overnight at 25° C. The cells were then inoculated in a PDA agar plate medium containing 0.5 mg/ml G418, and cultured 3 to 4 days to obtain transfectants.

Then, in order to confirm incorporation of the introduced gene in the genomic DNA of transfectant, a PCR was performed using genomic DNA as a template, using Δ5 desaturase amplification primers d5fulllengthF (SEQ ID NO: 72 in the Sequence Listing) d5fulllengthR (SEQ ID NO: 73 in the Sequence Listing), and neomycin-resistant gene amplification primers FU2FA (SEQ ID NO: 76 in the Sequence Listing) and FU2RA (SEQ ID NO: 77 in the Sequence Listing) (PCR program: 98° C. 10 sec/98° C. 10 sec/60° C. 30 sec/72° C. 1.5 min, 30 cycles).

The result confirmed amplification of the introduced gene, and incorporation in the genome (FIG. 39).

vi. Expression of Δ45 Desaturase mRNA

The *Aurantiochytrium* sp. mh0186 transfectants were cultured, and RNA extraction was performed according to the protocol attached to the kit (Sepasol RNA I super; nacalai tesque). First, the total RNA obtained from each clone was reverse transcribed to synthesize cDNA, using a PrimeScript Reverse Transcriptase (TakaraBio). Then, a PCR was performed under the following conditions, using the cDNA as a template (PCR cycles: 98° C. 10 sec/55° C. 30 sec/72° C. 1.5 min, 30 cycles).

As a result, amplification of each target gene was confirmed (FIG. 40). The result thus confirmed expression of the introduced gene in the transfectants through transcription into mRNA.

EXAMPLE 7

Modification of *Aurantiochytrium limacinum* mh0186 Fatty Acid Composition by Transformation (1) Modification of Fatty Acid Composition by Expression of Pinguiochrysis-Derived Δ12 Desaturase The transformed clone obtained in Example 6, (2), v. was cultured for 2 days in a 10-ml GY liquid medium (containing 0.5 mg/ml G418), and for an additional day after adding oleic acid to make the final concentration 50 µM. After culturing, the fatty acid composition was analyzed by GC and GC-MS analyses as in Example 6, (2), iv. A gas chromatograph GC-2014 (Shimadzu Corporation) was used for the GC analysis, which was performed under the following conditions. Column: HR-SS-10 (30 m×0.25 mm; Shinwa Chemical Industries Ltd.), column temperature: 150° C.→(5° C./min)→220° C. (10 min), carrier gas: He (1.3 mL/min). GC-17A and GCMS-QP-5000 (Shimadzu Corporation) were used for the GC-MS analysis, which was performed using a DB-1 capillary column (0.25 mmi.d.×30 m, film thickness 0.25 µm; Agilent) under the following conditions: column temperature 160° C.→(4° C./min)→260° C., injector port temperature 250° C. For peaks that caused troubles in the analyses, the fatty acids were analyzed after picolinyl esterification, using the same apparatuses and columns under the temperature condition 240° C.→(2.5° C./min)→260° C. (15 min)→(2.5° C./min)→280° C. A transfectant produced by introducing only the neomycin-resistant gene cassette was used as a control.

The GC analysis of the fatty acid compositions of the transfectants confirmed a new peak in the Δ12 desaturase gene/neomycin-resistant gene expression cassette-introduced strain, but not in the control strain, at a position corresponding to the retention time of linoleic acid (FIG. 41). The GC-MS analysis of the new peak revealed that the molecular weight and fragment pattern coincide with those of the sample linoleic acid methyl ester (FIG. 42). The conversion efficiency from oleic acid to linoleic acid was 30.1±6.64%, and there was no effect on other fatty acid compositions (FIG. 43).

(2) Changes in Fatty Acids by Expression of *Thraustochytrium aureum*-Derived Δ5 Desaturase The transformed clone obtained in Example 6, (3), v. was cultured for 3 days, and mhneo$^r$ and mhΔ5neo$^r$ were analyzed by GC analysis after extracting the fatty acid methyl ester.

Separately, 0.1 mM ETA or DGLA, exogenous fatty acids used as a substrate by Δ5 desaturase, was added to medium for incorporation into *Labyrinthula*, and GC analysis was performed after extracting the fatty acids as in the overexpression experiment using yeast. A gas chromatograph GC-2014 (Shimadzu Corporation) was used for the GC analysis, which was performed under the following conditions. Column: HR-SS-10 (30 m×0.25 mm; Shinwa Chemical Industries Ltd.), column temperature: 150° C.→(5° C./min)→220° C. (10 min), carrier gas: He (1.3 mL/min).

It was found that the endogenous ETA in the *Aurantiochytrium* sp. mh0186 strain was converted by the action of the introduced Δ5 desaturase, and that the EPA content was higher than in mhneo$^r$ by a factor of about 1.4 (FIG. 44, Table 8). ETA or DGLA used as a substrate by Δ5 desaturase was also added to medium at 0.1 mM for incorporation into *Labyrinthula*. As a result, the precursor substances converted into EPA and AA in *Labyrinthula*, and the content increased, as observed in the Δ5 desaturase expression experiment using yeast (Tables 9 and 10). The conversion efficiencies of the precursor substances in *Labyrinthula* were higher than in yeast, 75.2% and 62.9% for ETA and DGLA, respectively. This experiment was repeated in three or more confirmatory experiments to confirm reproducibility. All experiments produced the same results.

TABLE 8

|  | mhneor (%) | mhΔ5neor (%) |
|---|---|---|
| C14:0 | 2.23 ± 0.05 | 2.32 ± 0.03 |
| C15:0 | 2.43 ± 0.62 | 2.97 ± 0.96 |
| C16:0 | 55.2 ± 1.83 | 52.1 ± 3.15 |
| C17:0 | 0.97 ± 0.22 | 1.19 ± 0.42 |
| C18:0 | 1.54 ± 0.03 | 1.39 ± 0.13 |
| DGLA | ND | ND |
| AA | 0.18 ± 0.04 | 0.21 ± 0.02 |
| ETA | 0.32 ± 0.02 | 0.04 ± 0.04 |
| EPA | 0.65 ± 0.04 | 0.94 ± 0.13 |
| DPA | 5.17 ± 0.05 | 5.61 ± 1 |
| DHA | 31.3 ± 0.93 | 33.2 ± 2.44 |

TABLE 9

|  | mhneor + DGLA (%) | mhΔ5neor + DGLA (%) |
|---|---|---|
| C14:0 | 2.22 ± 0.06 | 2.28 ± 0.16 |
| C15:0 | 2.53 ± 0.63 | 2.96 ± 0.79 |
| C16:0 | 53.5 ± 2.36 | 52 ± 3.41 |
| C17:0 | 0.99 ± 0.21 | 1.19 ± 0.41 |
| C18:0 | 1.56 ± 0.03 | 1.42 ± 0.13 |
| DGLA* | 3.92 ± 0.21 | 1.09 ± 0.7 |
| AA | 0.14 ± 0.01 | 1.85 ± 0.24 |
| ETA | 0.39 ± 0.04 | 0.08 ± 0.05 |
| EPA | 0.6 ± 0.04 | 1.15 ± 0.29 |
| DPA | 4.92 ± 0.11 | 5.44 ± 0.89 |
| DHA | 29.3 ± 1.32 | 30.5 ± 1.94 |

TABLE 10

|  | mhneor + ETA (%) | mhΔ5neor + ETA (%) |
|---|---|---|
| C14:0 | 2.26 ± 0.1 | 2.43 ± 0.07 |
| C15:0 | 2.48 ± 0.64 | 3.04 ± 0.91 |
| C16:0 | 54.6 ± 1.56 | 51.8 ± 3.56 |
| C17:0 | 0.96 ± 0.23 | 1.17 ± 0.41 |
| C18:0 | 1.56 ± 0.02 | 1.4 ± 0.13 |
| DGLA | ND | ND |
| AA | 0.15 ± 0.02 | 0.22 ± 0.02 |
| ETA* | 3.27 ± 0.44 | 0.94 ± 0.5 |
| EPA | 0.62 ± 0.03 | 2.85 ± 0.35 |
| DPA | 4.92 ± 0.06 | 5.35 ± 0.97 |
| DHA | 29.2 ± 0.53 | 30.8 ± 2.52 |

EXAMPLE 8

*Labyrinthula* Gene Introduction Experiment 2

Gene introduction experiments were conducted using *Schizochytrium aggregatum* ATCC 28209, *Ulkenia* sp. ATCC 28207, *Schizochytrium* sp. SEK210 (NBRC 102615), *Schizochytrium* sp. SEK345 (NBRC 102616), *Botryochytrium radiatum* SEK353 (NBRC 104107), and *Parietichytrium sarkarianum* SEK364.

(1) Determination of MIC in Agar Plate Culture

Precultures (5 µl) of the six Labyrinthulomycetes strains were dropped onto PDA agar plate media containing various concentrations of G418. After culturing the cells at 28° C. for 7 days, colony formation was observed. In consideration of the results of the antibiotic sensitivity test and the selection marker genes used for the eukaryotes transformation system, G418 was found to be effective for the selection marker genes usable in the Labyrinthulomycetes transformation system.

(2) Isolation of *T. aureum*-Derived Ubiquitin Gene and Gene Expression Regulatory Region Isolation of the *T. aureum*-derived ubiquitin gene and the gene expression regulatory region was performed in the same manner as in Example 3.

(3) Production of Drug-Resistant Gene Expression Cassette

The drug-resistant gene expression cassette was produced in the same manner as in Example 4.

(4) Gene Introduction Experiment

A gene introduction experiment was conducted using a linear Neo$^r$ expression cassette (ub-Neo$^r$) adopting the ubiquitin promoter and terminator. The cassette was produced by performing a PCR with an oligonucleotide primer set NeoF (SEQ ID NO: 78 in the Sequence Listing)/NeoR (SEQ ID NO: 79 in the Sequence Listing), using an LA taq Hot Start Version (Takara Bio), and the pUBNeomycin r obtained in Example 4-ii. as a template, and the resulting amplification product was gel purified.

The gene introduction experiment was performed by electroporation. Specifically, Labyrinthulomycetes were cultured in a GY liquid medium or H liquid medium to the early to late stage of the logarithmic growth phase at 28° C., 150 rpm, and the supernatant was removed by centrifugation at 3,500×g, 4° C. for 10 min. The resulting cells were suspended in sterilized 1.75% Sea Life (Marine Tech), and washed by recentrifugation. The cells (5×10$^6$) were then suspended with the introduced DNA ub-Neo$^r$ in a reagent NucleofectorR solution L for gene introduction (amaxa). This was followed by application of electrical pulses using a Gene Pulser (Bio-Rad Laboratories; 1-mm gap cuvette; pulse settings: 50 µF/50 Ω/0.75 kV, applied twice). After applying electrical pulses, GY liquid medium (1 ml) was immediately added, and the cells were cultured at 28° C. for 12 hours. The culture fluid was then applied to a PDA agar plate medium containing 2.0 mg/ml G418 (*Ulkenia* sp. ATCC 28207, *Schizochytrium* sp. SEK210, and *Parietichytrium sarkarianum* SEK364), or 1.0 mg/ml G418 (*Botryochytrium radiatum* SEK353, *Schizochytrium aggregatum* ATCC 28209, and Schizochytrium sp. SEK345). After static culturing at 28° C., colony formation of transfectants with the conferred G418 resistance was observed.

As a result, colonies with the conferred G418 resistance were observed for the linear DNA ub-Neo$^r$ at the efficiency as high as $1.6 \times 10^0$ cfu/μg DNA. It was found that the transfectants maintained the G418 resistance even after being subcultured five times in a GY liquid medium containing no G418. The result using G418 resistance as an index thus confirmed that the conferred character was stable.

(5) Evaluation of Transfectant by PCR Using Genomic DNA as Template

The transfectants were cultured in GY liquid media containing 1.0 and 2.0 mg/ml G418. The wild-type strain was cultured in a GY liquid medium containing no G418. Genomic DNA was extracted from the cells of these strains using an ISOPLANT (nacalai tesque). Neo$^r$ was then amplified by PCR using a KOD FX (Toyobo life science), using the genomic DNA as a template. Oligonucleotide primers NeoF (SEQ ID NO: 78 in the Sequence Listing)/NeoR (SEQ ID NO: 79 in the Sequence Listing) were used (PCR cycles: 94° C. 2 min/98° C. 10 sec, 68° C. 30 sec, 72° C. 2 min, 30 cycles/4° C.). As a result, specific Neo$^r$ amplification, not found in the wild-type strain, was observed in the transfectants (FIG. 45). The result thus suggested that the introduced ub-Neo$^r$ was incorporated in the chromosomal DNA.

Example 9

Expression of ω3 Desaturase Gene in *Thraustochytrium aureum*

Example 9-1

Subcloning of SV40 Terminator Sequence

An SV40 terminator sequence was amplified with PrimeSTAR polymerase (Takara Bio), using a pcDNA 3.1 Myc-His vector as a template. The following PCR primers were used. RHO58 was set on the SV40 terminator sequence, and included BglII and BamHI linker sequences. RHO52 was set on the SV40 terminator sequence, and included a BglII sequence. [RHO58: 34 mer: 5'-C<u>AGATCT</u>GGATCCGC GAA ATG ACC GAC CAA GCG A-3' (SEQ ID NO: 80), RHO52: 24 mer: 5'-ACG CAA TTA ATG TG<u>AGATCT</u>A GCT-3' (SEQ ID NO: 81)]. After amplification performed under the conditions below, the product was cloned into a pGEM-T easy vector (Promega). [PCR cycles: 98° C. 2 min/98° C. 30 sec, 60° C. 30 sec, 72° C. 1 min, 30 cycles/72° C. 1 min]. After amplification with *Escherichia coli*, the sequence was confirmed by using a Dye Terminator Cycle Sequencing Kit. This was named pRH27.

The plasmid (pRH27) containing the subcloned SV40 terminator sequence (342 bp, SEQ ID NO: 82) is shown in FIG. 46.

Example 9-2

Production of Blasticidin Resistant Gene Cassette

A ubiquitin promoter sequence (618 bp, SEQ ID NO: 83) was amplified from *Thraustochytrium aureum* ATCC 34304 with a PrimeSTAR GC polymerase, using genomic DNA as a template. The following PCR primers were used. RHO53 was set on the ubiquitin promoter sequence, and included a BglII linker sequence. RHO48 included a ubiquitin promoter sequence and a blasticidin resistant gene sequence. [RHO53: 36 mer: 5'-CCC <u>AGATCT</u> GCC GCA GCG CCT GGT GCA CCC GCC GGG-3' (SEQ ID NO: 84), RHO48: 58 mer: 5'-CTT CTT GAG ACA AAG GCT TGG CCA TGT TGG CTA GTG TTG CTT AGG TCG CTT GCT GCT G-3' (SEQ ID NO: 85)]. [PCR cycles: 98° C. 2 min/98° C. 10 sec, 68° C. 1 min, 30 cycles/68° C. 1 min].

The blasticidin resistant gene (432 bp, SEQ ID NO: 86) was amplified with a PrimeSTAR GC polymerase, using pTracer-CMV/Bsd/lacZ as a template. The following PCR primers were used. RHO47 included a ubiquitin promoter sequence and a blasticidin resistant gene sequence. RHO49 included a blasticidin resistant gene sequence, and had a BglII linker sequence. [RHO47: 54 mer: 5'-AGC GAC CTA AGC AAC ACT AGC CAA CAT GGC CAA GCC TTT GTC TCA AGA AGA ATC-3' (SEQ ID NO: 87), RHO49: 38 mer: 5'-CCC <u>AGATCT</u> TAG CCC TCC CAC ACA TAA CCA GAG GGC AG-3' (SEQ ID NO: 88)]. [PCR cycles: 98° C. 2 min/98° C. 10 sec, 68° C. 1 min, 30 cycles/68° C. 1 min].

Fusion PCR was performed with RHO53 (SEQ ID NO: 85) and RHO49 (SEQ ID NO: 88), using SEQ ID NOS: 83 and 86 as templates. LA taq Hot start version was used as the enzyme, and the amplification was performed under the following conditions. [PCR cycles: 94° C. 2 min/94° C. 20 sec, 55° C. 30 sec, 68° C. 1 min, 30 cycles/68° C. 1 min; 1° C./10 sec from 55° C. to 68° C.] (FIG. 47).

The *Thraustochytrium aureum* ATCC 34304-derived ubiquitin promoter-pTracer-CMV/Bsd/lacZ-derived blasticidin resistant gene (1,000 bp, SEQ ID NO: 89) fused as above was digested with BglII, and ligated at the BamHI site of pRH27 (FIG. 46) described in Example 9-1. The resulting plasmid was amplified with *Escherichia coli*, and the sequence was confirmed by using a Dye Terminator Cycle Sequencing Kit. This was named pRH38.

The product blasticidin resistant gene cassette (pRH38) is shown in FIG. 48.

Example 9-3

Cloning of *Saprolegnia diclina*-Derived ω3 Desaturase Gene, and Production of Gene Expression Plasmid A ubiquitin promoter sequence (longer) (812 bp, SEQ ID NO: 90) was amplified from with an LA taq GC II polymerase, using genomic DNA of *Thraustochytrium aureum* ATCC 34304 as a template. The following PCR primers were used. TMO42 was set on the ubiquitin promoter sequence, upstream of RHO53 (Example 9-2, SEQ ID NO: 84), and included a KpnI linker sequence. TMO43 included a ubiquitin promoter sequence and a *Saprolegnia diclina*-derived ω3 desaturase gene sequence. [TMO42: 29 mer: 5'-TC G<u>GTACCC</u> GTT AGA ACG CGT AAT ACG AC-3' (SEQ ID NO: 91), TMO43: 45 mer: 5'-TTC GTC TTA TCC TCA GTC ATG TTG GCT AGT GTT GCT TAG GTC GCT-3' (SEQ ID NO: 92)]. [PCR cycles: 96° C. 2 min/98° C. 20 sec, 60° C. 30 sec, 72° C. 1 min, 30 cycles/72° C. 1 min].

The *Saprolegnia diclina* was then cultured in a medium containing D-glucose (31.8 g) and a yeast extract (10.6 g) per liter (adjusted with deionized water). Cells in the late stage of the logarithmic growth phase were centrifuged at 4° C., 3,500×g for 5 min to prepare pellets, and freeze disrupted with liquid nitrogen. The disrupted cell solution was extracted with phenol. After ethanol precipitation, the precipitate was dissolved in TE solution. The nucleic acids dissolved in the TE solution were treated with RNase at 37° C. for 30 min to degrade RNA, and extracted again with phenol. After ethanol precipitation, the precipitate was dissolved in TE solution. The DNA purity and concentration were calculated by measuring A260/280. The *Saprolegnia diclina*-derived ω3 desaturase gene sequence (1,116 bp, SEQ ID NO: 93) was amplified with an LA taq GC II polymerase, using the genomic DNA of the *Saprolegnia diclina* as a template. The following PCR primers were used. TMO44 included a ubiquitin promoter sequence and a *Saprolegnia diclina*-derived ω3 desaturase gene sequence. TMO45 included a *Saprolegnia diclina*-derived ω3 desaturase gene sequence and a ubiquitin terminator. [TMO44: 43 mer: 5'-CCT AAG CAA CAC TAG CCA ACA TGA CTG AGG ATA AGA CGA AGG T-3' (SEQ ID NO: 94), TMO45: 40 mer: 5'-ATA CTA CAG ATA GCT TAG TTT TAG TCC GAC TTG GCC TTG G-3' (SEQ ID NO: 95)]. [PCR cycles: 96° C. 2 min/98° C. 20 sec, 60° C. 30 sec, 72° C. 1 min 30 sec, 30 cycles/72° C. 1 min 30 sec].

The ubiquitin terminator sequence (614 bp, SEQ ID NO: 96) was amplified with an LA taq GC II polymerase, using the genomic DNA of *Thraustochytrium aureum* ATCC 34304 as a template. The following PCR primers were used. TMO46 included a *Saprolegnia diclina*-derived ω3 desaturase gene sequence and a ubiquitin terminator. TMO47 was designed on the ubiquitin terminator sequence, and included a KpnI linker sequence. [TMO46: 44 mer: 5'-CCA AGG CCA AGT CGG ACT AAA ACT AAG CTA TCT GTA GTA TGT GC-3' (SEQ ID NO: 97), TMO47: 45 mer: 5'-TCGGTACCA CCG CGT AAT ACG ACT CAC TAT AGG GAG ACT GCA GTT-3' (SEQ ID NO: 98)]. [PCR cycles: 96° C. 2 min/98° C. 20 sec, 60° C. 30 sec, 72° C. 1 min, 30 cycles/72° C. 1 min].

Fusion PCR was performed with TMO42 (SEQ ID NO: 91) and TMO47 (SEQ ID NO: 98), using SEQ ID NOS: 90, 93, and 96 as templates. LA taq GC II polymerase was used as the enzyme, and the amplification was performed under the following conditions. [PCR cycles: 96° C. 2 min/98° C. 20 sec, 55° C. 30 sec, 68° C. 3 min, 30 cycles/68° C. 3 min; 1° C./10 sec from 55° C. to 68° C.] (FIG. 49, 2,463 bp, SEQ ID NO: 99).

A PCR was performed with RHO84 (SEQ ID NO: 100, presented below) and RHO52 (Example 9-1, SEQ ID NO: 101), using the pRH38 (FIG. 48) described in Example 9-2 as a template. RHO84 was set on the ubiquitin promoter, and had a KpnI linker sequence. RHO52 was set on the SV40 terminator sequence, and had a BglII linker. LA taq Hot start version was used as the enzyme, and the amplification was performed under the following conditions, and cloned into a pGEM-T easy vector. [RHO84: 36 mer: 5'-CCC GGTACC GCC GCA GCG CCT GGT GCA CCC GCC GGG-3' (SEQ ID NO: 100)]. [PCR cycles: 98° C. 2 min/98° C. 10 sec, 68° C. 1 min 30 sec, 30 cycles/68° C. 3 min]. After amplification with *Escherichia coli*, the sequence was confirmed by using a Dye Terminator Cycle Sequencing Kit. This was named pRH45 (FIG. 50).

The fused *Thraustochytrium aureum* ATCC 34304-derived ubiquitin promoter-*Saprolegnia diclina*-derived ω3 desaturase gene-*Thraustochytrium aureum* ATCC 34304-derived ubiquitin terminator (SEQ ID NO: 99; FIG. 49) was digested with KpnI, and ligated at the KpnI site of the pRH45 (FIG. 50). The resulting plasmid was amplified with *Escherichia coli*, and the sequence was confirmed by using a Dye Terminator Cycle Sequencing Kit. This was named pRH48.

The product *Saprolegnia diclina*-derived ω3 desaturase gene expression plasmid (pRH48) is shown in FIG. 51.

Example 9-4

Introduction of *Saprolegnia diclina*-Derived ω3 Desaturase Expression Plasmid into *Thraustochytrium aureum*

DNA was amplified using a Prime STAR Max polymerase with primers TMO42 (Example 9-3, SEQ ID NO: 91) and RHO52 (Example 9-1, SEQ ID NO: 81), using the targeting vector produced in Example 9-3 as a template. [PCR cycles: 94° C. 30 sec, 72° C. 1 min, 5 cycles/94° C. 30 sec, 70° C. 30 sec, 72° C. 1 min, 5 cycles/94° C. 30 sec, 68° C. 30 sec, 72° C. 1 min, 25 cycles/72° C. 2 min]. The amplification product was collected from 1.0% agarose gel, and, after ethanol precipitation, the precipitate was dissolved in 0.1×TE. The DNA concentration was calculated by measuring A260/280. The fragment amplified by PCR was 3,777 bp, and contained the ubiquitin promoter-ω3 desaturase gene-ubiquitin terminator-ubiquitin promoter-blasticidin resistant gene sequence- and SV40 terminator sequence in this order (SEQ ID NO: 101).

*Thraustochytrium aureum* was cultured in a GY medium for 4 days, and cells in the logarithmic growth phase were used for gene introduction. A DNA fragment (0.625 µg) was introduced into cells corresponding to $OD_{600}=1$ to 1.5, using the gene gun technique (microcarrier: 0.6-micron gold particles, target distance: 6 cm, chamber vacuum: 26 mmHg, rupture disk: 1,100 PSI). After a 4- to 6-hour recovery time, the gene introduced cells were applied onto a 0.2 mg/ml blasticidin-containing PDA agar plate medium.

Twenty to thirty drug-resistant strains were obtained per penetration.

Example 9-5

Acquisition of *Saprolegnia diclina*-Derived ω3 Desaturase Gene Expressing Strain Genomic DNA was extracted from the ω3 desaturase gene expressing strain obtained in Example 9-4, and the DNA concentration was calculated by measuring A260/280. By using this as a template, a PCR was performed to confirm the genome structure, using an LA taq Hot start version. The positions of the primers, combinations used for the amplification, and the expected size of the amplification product are shown in FIG. 52. TMO42 (Example 9-3, SEQ ID NO: 91) was set on the ubiquitin promoter, and RHO49 (Example 9-2, SEQ ID NO: 88) on the blasticidin resistant gene. [PCR cycles: 98° C. 2 min/98° C. 10 sec, 68° C. 4 min, 30 cycles/68° C. 7 min].

The result of amplification confirmed a band of an expected size (FIG. 53). That is, a strain was isolated that contained the introduced expression fragment stably introduced into its genome.

Example 9-6

Changes in Fatty Acid Composition by Expression of ω3 Desaturase in *Thraustochytrium aureum*

The *Thraustochytrium aureum*, and the ω3 desaturase expressing strain obtained in Example 9-5 were cultured. After freeze drying, the fatty acids were subjected to methylesterification, and analyzed by GC analysis. A gas chromatograph GC-2014 (Shimadzu Corporation) was used for the GC analysis, which was performed under the following conditions. Column: HR-SS-10 (30 m×0.25 mm; Shinwa Chemical Industries Ltd.), column temperature: 150° C.→(5° C./min)→220° C. (10 min), carrier gas: He (1.3 mL/min).

The ω3 desaturase expressing strain had reduced levels of the n-6 series fatty acids, and there was a tendency for the n-3 series fatty acids to increase (FIG. 54). FIG. 55 represents the percentage relative to the wild-type strain taken as 100%.

As a result, the arachidonic acid was reduced by about 1/10, and the DPA by about 1/7. EPA increased by a factor of about 1.8, and DHA by a factor of about 1.2.

Industrial Applicability

The present invention provides modification of the fatty acid composition produced by stramenopiles, and a method for highly accumulating fatty acids in stramenopiles. The invention thus enables more efficient production of polyunsaturated fatty acids.

The invention claimed is:

1. A method for modifying the fatty acid composition of stramenopiles, comprising:
   introducing a heterologous fatty acid desaturase gene into Parietichytrium sarkarianum SEK364 (FERM ABP-11298), wherein said heterologous fatty acid desaturase gene is cloned in an expression vector; and
   expressing the fatty acid desaturase.

2. The method according to claim 1, wherein the fatty acid desaturase is a desaturase.

3. The method according to claim 2, wherein the desaturase is a Δ5 desaturase, a Δ12 desaturase, or an ω3 desaturase.

4. A method for highly accumulating an unsaturated fatty acid in stramenopiles by using the method of any one of claims 1 to 3.

5. The method according to claim 4, wherein the unsaturated fatty acid is an unsaturated fatty acid of 18 to 22 carbon atoms.

* * * * *